United States Patent
Claiborne et al.

(10) Patent No.: US 7,217,716 B2
(45) Date of Patent: May 15, 2007

(54) N-SUBSTITUTED NONARYL-HETEROCYCLIC NMDA/NR2B ANTAGONISTS

(75) Inventors: Christopher F. Claiborne, Cambridge, MA (US); David A. Claremon, Maple Glen, PA (US); Brian E. Libby, Noblesville, IN (US); John W. Butcher, Telford, PA (US); John A. McCauley, Maple Glen, PA (US); Nigel J. Liverton, Harleysville, PA (US); Peter M. Munson, Harleysville, PA (US); Kevin T. Nguyen, Philadelphia, PA (US); Brian Phillips, Telford, PA (US); Wayne Thompson, Landsdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 27 days.

(21) Appl. No.: 10/470,561

(22) PCT Filed: Feb. 20, 2002

(86) PCT No.: PCT/US02/05226

§ 371 (c)(1),
(2), (4) Date: Jul. 29, 2003

(87) PCT Pub. No.: WO02/068409

PCT Pub. Date: Sep. 6, 2002

(65) Prior Publication Data

US 2004/0209889 A1    Oct. 21, 2004

Related U.S. Application Data

(60) Provisional application No. 60/271,100, filed on Feb. 23, 2001.

(51) Int. Cl.
C07D 401/12    (2006.01)
A61K 31/444    (2006.01)

(52) U.S. Cl. .................. 514/263.2; 514/263.4; 514/275; 514/304; 544/277; 544/330; 546/124; 546/125; 546/126

(58) Field of Classification Search ............... 544/277, 544/330; 546/124, 125, 126; 514/263.2, 514/275, 263.4, 304
See application file for complete search history.

(56) References Cited

U.S. PATENT DOCUMENTS

| 3,184,462 A | 5/1965 | Scarborough et al. |
| 5,807,855 A * | 9/1998 | Bøgesø, et al. ........ 514/252.13 |
| 6,124,323 A | 9/2000 | Bigge et al. |

FOREIGN PATENT DOCUMENTS

WO    WO 84/01151    *    3/1984

OTHER PUBLICATIONS

XP-002201030—L. Zhou, et al., *J. Med. Chem.*, 42, pp. 2993-3000 (1999).

* cited by examiner

*Primary Examiner*—Deepak Rao
(74) *Attorney, Agent, or Firm*—Mollie M. Yang; Valerie J. Camara

(57) ABSTRACT

Compounds represented by Formula (I): (I) or pharmaceutically acceptable salts thereof, are effective as NMDA NR2B antagonists useful for relieving pain (I)

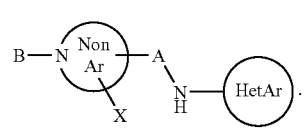

9 Claims, No Drawings

N-SUBSTITUTED NONARYL-HETEROCYCLIC NMDA/NR2B ANTAGONISTS

RELATED APPLICATION DATA

This is a National filing under 35 USC 371 of PCT/US 02/05226, filed Feb. 20, 2002, which claims priority from U.S. Ser. No. 60/271,100, filed Feb. 23, 2001.

BACKGROUND OF THE INVENTION

Field of the Invention

This invention relates to N-substituted nonarylheterocyclic compounds. In particular, this invention relates to N-substituted nonarylheterocyclic compounds that are effective as NMDA NR2B antagonists useful for relieving pain.

Ions such as glutamate play a key role in processes related to chronic pain and pain-associated neurotoxicity—primarily by acting through N-methyl-D-aspartate ("NMDA") receptors. Thus, inhibition of such action—by employing ion channel antagonists, particularly NMDA antagonists—can be beneficial in the treatment and control of pain.

Known NMDA antagonists include ketamine, dextromophan, and 3-(2-carboxypiperazin-4-yl)-propyl-1-phosphonic acid ("CPP"). Although these compounds have been reported (J. D. Kristensen, et al., *Pain*, 51:249–253 (1992); P. K. Eide, et al., *Pain*, 61:221–228 (1995); D. J. Knox, et al., *Anaesth. Intensive Care* 23:620–622 (1995); and M. B. Max, et al., *Clin.Neuropharmacol.* 18:360–368 (1995)) to produce symptomatic relief in a number of neuropathies including postherpetic neuralgia, central pain from spinal cord injury, and phantom limb pain, widespread use of these compounds is precluded by their undesirable side effects. Such side effects at analgesic doses include psychotomimetic effects such as dizziness, headache, hallucinations, dysphoria, and disturbances of cognitive and motor function. Additionally, more severe hallucinations, sedation, and ataxia are produced at doses only marginally higher than analgesic doses. Thus, it would be desirable to provide novel NMDA antagonists that are absent of undesirable side effects or that produce fewer and/or milder side effects.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided into four individual subunit types: NR2A, NR2B, NR2C, and NR2D. T. Ishii, et al., *J. Biol. Chem.*, 268:2836–2843 (1993), and D. J. Laurie et al., *Mol. Brain Res.*, 51:23–32 (1997) describe how the various resulting combinations produce a variety of NMDA receptors differing in physiological and pharmacological properties such as ion gating properties, magnesium sensitivity, pharmacological profile, as well as in anatomical distribution.

For example, while NR1 is found throughout the brain, NR2 subunits are differentially distributed. In particular, it is believed that the distribution map for NR2B lowers the probability of side effects while producing pain relief. For example, S. Boyce, et al., *Neurophamacology*, 38:611–623 (1999) describes the effect of selective NMDA NR2B antagonists on pain with reduced side effects. Thus, it would be desirable to provide novel NMDA antagonists that target the NR2B receptor.

U.S. Pat. No. 6,020,347 and International Patent Publication WO99/25685 describes 4-substituted-4-piperidine carboxamide derivatives that are antagonists of VLA-4 ("Very Late Antigen-4"). International Patent Publication WO01/00207 describes substituted pyrimidine compounds that are inhibitors of tyrosine kinases. International Patent Publication WO 00/61551 describes oxopyrimidinealkanoate compounds that are integrin receptor ligands. International Patent Publication EP 604800 describes Carboxyalkyl-phenyl aminocarbonyl-phenyl-piperidine compounds that are blood platelet aggregation inhibitors. International Patent Publication EP 611660 describes benzimidazoles, xanthines, and analogs as tissue aggregation inhibitors. International Patent Publication EP 771799 and U.S. Pat. No 5,861,396 describe purin-6-one derivatives for the treatment of cardiovascular and urogenital diseases. International Patent Publication WO94/21615 describes benzimidazole-piperidine compounds utilized as dopamine D4 antagonists. German Patent No. DE4241632 describes substituted phenyl or cyclohexyl-carboxylic acid derivatives that inhibit cell aggregation.

Phenol compounds described as NMDA antagonists are described in U.S. Pat. Nos. 5,306,723 and 5,436,255, and in International Patent Publications WO91/17156, WO92/19502, WO93/02052, WO96/37226, and EP 441506. Benzyl piperidine substituted with phenols or imidazoles are described in Z.-L. Zhou, et al., *J. Medicinal Chemistry*, 42:2993–3000(1999); T. F. Gregory, et al., Poster #94, 218th National Meeting American Chemical Society, New Orleans, La., Aug. 22–26, 1999. Other NMDA NR2B selective compounds are described in European Patent Publication EP 787493 and J. N. C. Kew et al., *British J.Pharmacol.*, 123:463(1998). However, there continues to be a need for novel NMDA antagonists that target the NR2B receptor.

SUMMARY OF THE INVENTION

The present invention relates to N-substituted nonarylheterocyclic compounds represented by Formula (I):

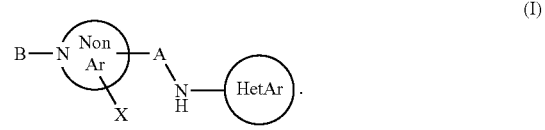

or pharmaceutically acceptable salts thereof. The present invention also forms pharmaceutical compositions utilizing the compounds. Further, this invention includes novel methods to treat pain by utilizing the compounds.

DETAILED DESCRIPTION OF THE INVENTION

The compounds of this invention are represented by Formula (I):

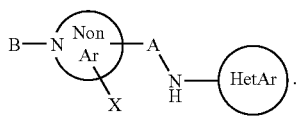 (I)

or pharmaceutically acceptable salts thereof, wherein

NonAr is a nonaromatic 5–7 membered ring containing 1 or 2 nitrogen ring atoms or an aza bicyclo octane ring;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, heteroaryl(CH$_2$)$_{1-3}$—O—C(O)—, indanyl(CH$_2$)$_{0-3}$—O—C(O)—, aryl(CH$_2$)$_{1-3}$—C(O)—, aryl-cyclopropyl-C(O)—, heteroaryl-cyclopropyl-C(O)—, heteroaryl(CH$_2$)$_{1-3}$—C(O)—, aryl(CH$_2$)$_{1-3}$—, heteroaryl(CH$_2$)$_{1-3}$—, aryl(CH$_2$)$_{1-3}$—NH—C(O)—, aryl(CH$_2$)$_{1-3}$—NH—C(NCN)—, aryl(CH$_2$)$_{1-3}$—SO$_2$—, heteroaryl(CH$_2$)$_{1-3}$—SO$_2$—, wherein any of the aryl or heteroaryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, P, $C_{1-4}$alkyl, $C_{1-4}$alkoxy, NH$_2$, or X taken with an adjacent bond is =O.

In one aspect, the compounds of this invention are represented by Formula (I) or pharmaceutically acceptable salts thereof, wherein NonAr is a nonaromatic 6 membered ring containing 1 nitrogen ring atom;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{1-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is a 6 membered heteroaromatic ring containing 1 nitrogen ring atom;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is an isoxazolyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In still another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is a thiadiazolyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In yet another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is a 5 membered heteroaromatic ring containing 2 nitrogen ring atoms;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is a quinolinyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In still another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is a purinyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In yet still another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is 6 membered heteroaromatic ring containing 2 nitrogen ring atoms;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In yet another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is a thiazolyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is a pteridinyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In still another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is a pyrrolopyrimidinyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In still yet another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is a imidazopyridinyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In yet still another embodiment of this first aspect, the compounds of this invention are represented by Formula (I) or pharmaceutically acceptable salts thereof, wherein NonAr is a nonaromatic 6 membered ring containing 1 nitrogen ring atom;

HetAr is a benzimidazolyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In a second aspect, the compounds of this invention are represented by Formula (I) or pharmaceutically acceptable salts thereof, wherein NonAr is a nonaromatic 6 membered ring containing 1 nitrogen ring atom;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{1-3}$—SO$_2$—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an embodiment of this second aspect, the compounds of this invention are represented by Formula (I) or pharmaceutically acceptable salts thereof, wherein NonAr is a nonaromatic 6 membered ring containing 1 nitrogen ring atom;

HetAr is a 6 membered heteroaromatic ring containing 2 nitrogen ring atoms;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{1-3}$—SO$_2$—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In another embodiment of the second aspect, the compounds of this invention are represented by Formula (I) or pharmaceutically acceptable salts thereof, wherein NonAr is a nonaromatic 6 membered ring containing 1 nitrogen ring atom;

HetAr is a quinazolinyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{1-3}$—SO$_2$—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In yet another embodiment of the second aspect, the compounds of this invention are represented by Formula (I) or pharmaceutically acceptable salts thereof, wherein NonAr is a nonaromatic 6 membered ring containing 1 nitrogen ring atom;

HetAr is purinyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{1-3}$—SO$_2$—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In still another embodiment of the second aspect, the compounds of this invention are represented by Formula (I) or pharmaceutically acceptable salts thereof, wherein NonAr is a nonaromatic 6 membered ring containing 1 nitrogen ring atom;

HetAr is imidazopyridinyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxyC$_{1-4}$alkyl, fluoro, chloro, bromo, iodo, cyano, methylsulfanyl, cyclopropylethynyl-, phenylethynyl-, heteroarylethynyl-, —N(C$_{0-4}$alkyl)(C$_{0-4}$alkyl), nitro, (C$_{1-2}$alkyl)(C$_{1-2}$alkyl)NCH$_2$—, (C$_{1-2}$alkyl)HNCH$_2$—, Si(CH$_3$)$_3$—C—, or NH$_2$C(O)—;

A is —C$_{0-4}$alkyl-;

B is aryl(CH$_2$)$_{1-3}$—SO$_2$—, wherein the aryl is optionally substituted by 1–5 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, NH$_2$, or X taken with an adjacent bond is =O.

In yet still another embodiment of the second aspect, the compounds of this invention are represented by Formula (I) or pharmaceutically acceptable salts thereof, wherein NonAr is a nonaromatic 6 membered ring containing 1 nitrogen ring atom;

HetAr is a 6 membered heteroaromatic ring containing 1 nitrogen ring atom;

HetAr is optionally substituted with 1 or 2 substituents, each substituent independently is C$_{1-4}$alkyl, C$_{1-4}$alkoxy, C$_{2-4}$alkynyl, trifluoromethyl, hydroxy, hydroxyC$_{1-4}$alkyl, fluoro, chloro, bromo, iodo, cyano, methylsulfanyl, cyclopropylethynyl-, phenylethynyl-, heteroarylethynyl-, —N(C$_{0-4}$alkyl)(C$_{0-4}$alkyl), nitro, (C$_{1-2}$alkyl)(C$_{1-2}$alkyl)NCH$_2$—, (C$_{1-2}$alkyl)HNCH$_2$—, Si(CH$_3$)$_3$—C—, or NH$_2$C(O)—;

A is —C$_{0-4}$alkyl-;

B is aryl(CH$_2$)$_3$—SO$_2$—, wherein the aryl is optionally substituted by 1–5 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, NH$_2$, or X taken with an adjacent bond is =O.

In a third aspect, the compounds of this invention are represented by Formula (I) or pharmaceutically acceptable salts thereof, wherein NonAr is a nonaromatic 5 membered ring containing 1 nitrogen ring atom;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is C$_{1-4}$alkyl, trifluoromethyl, hydroxy, hydroxyC$_{1-4}$alkyl, fluoro, chloro, bromo, iodo, cyano, methylsulfanyl, amino, nitro, (C$_{1-2}$alkyl)(C$_{1-2}$alkyl)NCH$_2$—, (C$_{1-2}$alkyl)HNCH$_2$—, or NH$_2$C(O)—;

A is —C$_{0-4}$alkyl-;

B is aryl(CH$_2$)$_3$—O—C(O)—, wherein the aryl is optionally substituted by 1–5 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, NH$_2$, or X taken with an adjacent bond is =O.

In an embodiment of the third aspect, the compounds of this invention are represented by Formula (I) or pharmaceutically acceptable salts thereof, wherein NonAr is a nonaromatic 5 membered ring containing 1 nitrogen ring atom;

HetAr is a 6 membered heteroaromatic ring containing 2 nitrogen ring atoms;

HetAr is optionally substituted with 1 or 2 substituents, each substituent independently is C$_{1-4}$alkyl, trifluoromethyl, hydroxy, hydroxyC$_{1-4}$alkyl, fluoro, chloro, bromo, iodo, cyano, methylsulfanyl, amino, nitro, (C$_{1-2}$alkyl)(C$_{1-2}$alkyl)NCH$_2$—, (C$_{1-2}$alkyl)HNCH$_2$—, or NH$_2$C(O)—;

A is —C$_{0-4}$alkyl-;

B is aryl(CH$_2$)$_{0-3}$—O—C(O)—, wherein the aryl is optionally substituted by 1–5 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, NH$_2$, or X taken with an adjacent bond is =O.

In another embodiment of the third aspect, the compounds of this invention are represented by Formula (I) or pharmaceutically acceptable salts thereof, wherein NonAr is a nonaromatic 5 membered ring containing 1 nitrogen ring atom;

HetAr is pteridinyl optionally substituted with 1 or 2 substituents, each substituent independently is C$_{1-4}$alkyl, C$_{1-4}$alkoxy, C$_{2-4}$alkynyl, trifluoromethyl, hydroxy, hydroxyC$_{1-4}$alkyl, fluoro, chloro, bromo, iodo, cyano, methylsulfanyl, cyclopropylethynyl-, phenylethynyl-, heteroarylethynyl-, —N(C$_{0-4}$alkyl)(C$_{0-4}$alkyl), nitro, (C$_{1-2}$alkyl)(C$_{1-2}$alkyl)NCH$_2$—, (C$_{1-2}$alkyl)HNCH$_2$—, Si(CH$_3$)$_3$—C—, or NH$_2$C(O)—;

A is —C$_{0-4}$alkyl-;

B is aryl(CH$_2$)$_{0-3}$—O—C(O)—, wherein the aryl is optionally substituted by 1–5 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, NH$_2$, or X taken with an adjacent bond is =O.

In still another embodiment of the third aspect, the compounds of this invention are represented by Formula (I) or pharmaceutically acceptable salts thereof, wherein NonAr is a nonaromatic 5 membered ring containing 1 nitrogen ring atom;

HetAr is purinyl optionally substituted with 1 or 2 substituents, each substituent independently is C$_{1-4}$alkyl, C$_{1-4}$alkoxy, C$_{2-4}$alkynyl, trifluoromethyl, hydroxy, hydroxyC$_{1-4}$alkyl, fluoro, chloro, bromo, iodo, cyano, methylsulfanyl, cyclopropylethynyl-, phenylethynyl-, heteroarylethynyl-, —N(C$_{0-4}$alkyl)(C$_{0-4}$alkyl), nitro, (C$_{1-2}$alkyl)(C$_{1-2}$alkyl)NCH$_2$—, (C$_{1-2}$alkyl)HNCH$_2$—, Si(CH$_3$)$_3$—C—, or NH$_2$C(O)—;

A is —C$_{0-4}$alkyl-;

B is aryl(CH$_2$)$_{0-3}$—O—C(O)—, wherein the aryl is optionally substituted by 1–5 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, NH$_2$, or X taken with an adjacent bond is =O.

In still another embodiment of the third aspect, the compounds of this invention are represented by Formula (I) or pharmaceutically acceptable salts thereof, wherein NonAr is a nonaromatic 5 membered ring containing 1 nitrogen ring atom;

HetAr is benzimidazolyl optionally substituted with 1 or 2 substituents, each substituent independently is C$_{1-4}$alkyl, C$_{1-4}$alkoxy, C$_{2-4}$alkynyl, trifluoromethyl, hydroxy, hydroxyC$_{1-4}$alkyl, fluoro, chloro, bromo, iodo, cyano, methylsulfanyl, cyclopropylethynyl-, phenylethynyl-, heteroarylethynyl-, —N(C$_{0-4}$alkyl)(C$_{0-4}$alkyl), nitro, (C$_{1-2}$alkyl)(C$_{1-2}$alkyl)NCH$_2$—, (C$_{1-2}$alkyl)HNCH$_2$—, Si(CH$_3$)$_3$—C—, or NH$_2$C(O)—;

A is —C$_{0-4}$alkyl-;

B is aryl(CH$_2$)$_{0-3}$—C(O)—, wherein the aryl is optionally substituted by 1–5 substituents, each substituent independently is C$_{1-4}$alkyl, C$_{3-6}$cycloalkyl, C$_{1-4}$alkoxy, trifluoromethyl, bromo, fluoro, or chloro; and X is H, OH, F, C$_{1-4}$alkyl, C$_{1-4}$alkoxy, NH$_2$, or X taken with an adjacent bond is =O.

In a fourth aspect, the compounds of this invention are represented by Formula (I) or pharmaceutically acceptable salts thereof, wherein NonAr is an aza bicyclo octane ring;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an embodiment of the fourth aspect, the compounds of this invention are represented by Formula (I) or pharmaceutically acceptable salts thereof, wherein NonAr is an aza bicyclo octane ring;

HetAr is a 6 membered heteroaromatic ring containing 1 nitrogen ring atom;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In another embodiment of the fourth aspect, the compounds of this invention are represented by Formula (I) or pharmaceutically acceptable salts thereof, wherein NonAr is an aza bicyclo octane ring;

HetAr is purinyl optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In still another embodiment of the fourth aspect, the compounds of this invention are represented by Formula (I) or pharmaceutically acceptable salts thereof, wherein NonAr is an aza bicyclo octane ring;

HetAr is a 6 membered heteroaromatic ring containing 2 nitrogen ring atom;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{0-3}$—O—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F; $C_{1-4}$alkyl, $C_{1-4}$alkoxy, NH$_2$, or X taken with an adjacent bond is =O.

In a fifth aspect, the compounds of this invention are represented by Formula (I) or pharmaceutically acceptable salts thereof, wherein NonAr is an aza bicyclo octane ring;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{1-3}$—SO$_2$—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an embodiment of the fifth aspect, the compounds of this invention are represented by Formula (I) or pharmaceutically acceptable salts thereof, wherein NonAr is an aza bicyclo octane ring;

HetAr is a 6 membered heteroaromatic ring containing 2 nitrogen ring atom;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{1-3}$—SO$_2$—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In a sixth aspect, the compounds of this invention are represented by Formula (I) or pharmaceutically acceptable salts thereof, wherein NonAr is a nonaromatic 6 membered ring containing 1 nitrogen ring atom;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is heteroaryl(CH$_2$)$_{1-3}$—C(O)—, wherein the heteroaryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an embodiment of the sixth aspect, the compounds of this invention are represented by Formula (I) or pharmaceutically acceptable salts thereof, wherein NonAr is a nonaromatic 6 membered ring containing 1 nitrogen ring atom;

HetAr is a 6 membered heteroaromatic ring containing 2 nitrogen ring atom;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is heteroaryl(CH$_2$)$_{1-3}$—C(O)—, wherein the heteroaryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In a seventh aspect, the compounds of this invention are represented by Formula (I) or pharmaceutically acceptable salts thereof, wherein NonAr is a nonaromatic 6 membered ring containing 1 nitrogen ring atom;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C, or NH$_2$C(O)—;

A is —$C_{0-4}$alkyl-;

B is aryl(CH$_2$)$_{1-3}$—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an embodiment of the seventh aspect, the compounds of this invention are represented by Formula (I) or pharmaceutically acceptable salts thereof, wherein NonAr is a nonaromatic 6 membered ring containing 1 nitrogen ring atom;

HetAr is 6 membered heteroaromatic ring containing 2 nitrogen ring atom;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{1-3}$—C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an eighth aspect, the compounds of this invention are represented by Formula (I) or pharmaceutically acceptable salts thereof, wherein NonAr is a nonaromatic 6 membered ring containing 1 nitrogen ring atom;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl-cyclopropyl-C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an embodiment of the eighth aspect, the compounds of this invention are represented by Formula (I) or pharmaceutically acceptable salts thereof, wherein NonAr is a nonaromatic 6 membered ring containing 1 nitrogen ring atom;

HetAr is a 6 membered heteroaromatic ring containing 2 nitrogen ring atoms;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl-cyclopropyl-C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an embodiment of the eighth aspect, the compounds of this invention are represented by Formula (I) or pharmaceutically acceptable salts thereof, wherein NonAr is a nonaromatic 6 membered ring containing 1 nitrogen ring atom;

HetAr is a pyrimidinyl ring optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl-cyclopropyl-C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In another embodiment of the eighth aspect, the compounds of this invention are represented by Formula (I) or pharmaceutically acceptable salts thereof, wherein NonAr is a nonaromatic 6 membered ring containing 1 nitrogen ring atom;

HetAr is a pyrazinyl ring optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl-cyclopropyl-C(O)—, wherein the aryl is optionally substituted by 1-5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In still another embodiment of the eighth aspect, the compounds of this invention are represented by Formula (I) or pharmaceutically acceptable salts thereof, wherein NonAr is a nonaromatic 6 membered ring containing 1 nitrogen ring atom;

HetAr is pyridazinyl ring optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl-cyclopropyl-C(O)—, wherein the aryl is optionally substituted by 1-5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In another embodiment of the eighth aspect, the compounds of this invention are represented by Formula (I) or pharmaceutically acceptable salts thereof, wherein NonAr is a nonaromatic 6 membered ring containing 1 nitrogen ring atom;

HetAr is a pyridyl ring optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl-cyclopropyl-C(O)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In a ninth aspect, the compounds of this invention are represented by Formula (I) or pharmaceutically acceptable salts thereof, wherein NonAr is a nonaromatic 6 membered ring containing 1 nitrogen ring atom;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is heteroaryl(CH$_2$)$_{1-3}$—O—C(O)—, wherein the heteroaryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an embodiment of the ninth aspect, the compounds of this invention are represented by Formula (I) or pharmaceutically acceptable salts thereof, wherein NonAr is a nonaromatic 6 membered ring containing 1 nitrogen ring atom;

HetAr is a 6 membered heteroaromatic ring containing 1 nitrogen ring atom;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is heteroaryl(CH$_2$)$_{1-3}$—O—C(O)—, wherein the heteroaryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In a tenth aspect, the compounds of this invention are represented by Formula (I) or pharmaceutically acceptable salts thereof, wherein NonAr is a nonaromatic 6 membered ring containing 1 nitrogen ring atom;

HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{1-3}$—NH—C(NCN)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

In an embodiment of the tenth aspect, the compounds of this invention are represented by Formula (I) or pharmaceutically acceptable salts thereof, wherein NonAr is a nonaromatic 6 membered ring containing 1 nitrogen ring atom;

HetAr is a 6 membered heteroaromatic ring containing 1 nitrogen ring atom;

HetAr is optionally substituted with 1 or 2 substituents, each substituent independently is $C_{1-4}$alkyl, $C_{1-4}$alkoxy, $C_{2-4}$alkynyl, trifluoromethyl, hydroxy, hydroxy$C_{1-4}$alkyl, fluoro, chloro, bromo, iodo, cyano, methylsulfanyl, cyclopropylethynyl-, phenylethynyl-, heteroarylethynyl-, —N($C_{0-4}$alkyl)($C_{0-4}$alkyl), nitro, ($C_{1-2}$alkyl)($C_{1-2}$alkyl)NCH$_2$—, ($C_{1-2}$alkyl)HNCH$_2$—, Si(CH$_3$)$_3$—C—, or NH$_2$C(O)—;

A is —$C_{0-4}$alkyl-;

B is aryl(CH$_2$)$_{1-3}$—NH—C(NCN)—, wherein the aryl is optionally substituted by 1–5 substituents, each substituent independently is $C_{1-4}$alkyl, $C_{3-6}$cycloalkyl, $C_{1-4}$alkoxy, trifluoromethyl, bromo, fluoro, or chloro; and X is H, OH, F, $C_{1-4}$alkyl, $C_{1-4}$alkoxy, NH$_2$, or X taken with an adjacent bond is =O.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl.

The term "aryloxy" unless specifically stated otherwise includes multiple ring systems as well as single ring systems such as, for example, phenyl or naphthyl, connected through the oxy connecting atom to the connecting site.

The term "$C_0$" means that the carbon is not present. Thus, "$C_0$–$C_5$" means that there are from none to five carbons present—that is, five, four, three, two, one, or no carbons present. When no carbons are present in a linking alkyl group, the link is a direct bond. When no carbons are present in a terminal alkyl group, the terminus is hydrogen.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Examples of heterocyclo$C_{3-7}$alkyl include, for example, azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

Examples of aryl($C_{1-6}$)alkyl include, for example, phenyl($C_{1-6}$)alkyl, and naphthyl($C_{1-6}$)alkyl.

Examples of heterocyclo$C_{3-7}$alkylcarbonyl($C_{1-6}$)alkyl include, for example, azetidinyl carbonyl($C_{1-6}$)alkyl, pyrolidinyl carbonyl($C_{1-6}$)alkyl, piperidinyl carbonyl($C_{1-6}$)alkyl, piperazinyl carbonyl($C_{1-6}$)alkyl, morpholinyl carbonyl($C_{1-6}$)alkyl, and thiomorpholinyl carbonyl($C_{1-6}$)alkyl.

The term "amine" unless specifically stated otherwise includes primary, secondary and tertiary amines.

Unless otherwise stated, the term "carbamoyl" is used to include —NHC(O)OC$_1$–C$_4$alkyl, and —OC(O)NHC$_1$–C$_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$)

alkyl includes substitution on the aryl group as well as substitution on the alkyl group.

Compounds described herein contain one or more double bonds and may thus give rise to cis/trans isomers as well as other conformational isomers. The present invention includes all such possible isomers as well as mixtures of such isomers.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 1 mg to about 500 mg of the active ingredient and each cachet or capsule preferably containing from about 1 to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Experimental Protocols

Assessing the Activity of Selected Compounds to Inhibit NR1A/2B NMDA Receptor Activation (FLIPR Assay)

The activity of selected compounds to inhibit NR1A/2B NMDA receptor activation measured as NR1A/2B receptor-mediated $Ca^{2+}$ influx is assessed by the following procedure:

NR1A/2B receptor transfected L(tk) cells are plated in 96-well format at $3\times10^6$ cells per plate and grown for one–two days in normal growth media (Dulbeccos MEM with Na pyruvate, 4500 mg glucose, pen/strep, glutamine, 10% FCS and 0.5 mg/mL geneticin). NR1A/2B-expression in these cells is induced by the addition of 4 nM dexamethasone in the presence of 500 µM ketamine for 16–24 hours. After receptor induction cells are washed using a Labsystem Cellwasher two times with assay buffer (Hanks balanced salt solution (HBSS-$Mg^{++}$ free) containing 20 mM HEPES, 0.1% BSA, 2 mM $CaCl_2$ and 250 µM probenecid). The cells of each 96 well cell plate are loaded with the $Ca^{++}$ sensitive dye Fluo-3 (Molecular Probes, Inc.) at 4 µM in assay buffer containing 0.5% FBS, and 0.04% pluronic F-127 (Molecular Probes, Inc.) for 1 h at 37° C. avoiding light. The cells are then washed with the Cellwasher four times with assay buffer leaving them in 100 µL buffer. Test compounds in solution are pipetted by FLIPR (Fluorometric Imaging Plate Reader) into each test well for a 2 min pretreatment. During this time the fluorescence intensity is recorded (excitation at 488 nm and emission at 530 nm). The glutamate/glycine 50 µL agonist solution (final concentration 1 µM/1 µM) is then added by FLIPR into each well already containing 150 µL of buffer (containing the test compound or vehicle) and the fluorescence is continuously monitored for 10 min. The endpoint fluorescence values are used to determine an $IC_{50}$ value comparing the agonist-stimulated signal for the vehicle alone sample and that for the cells incubated with each concentration of test compound.

Determining the Apparent Dissociation Constant (Ki) of Compounds for Human NR1A/NR2B Receptors (Binding Assay)

The radioligand binding assay is performed at room temperature in 96-well microtiter plates with a final assay volume of 1.0 mL in 20 mM Hepes buffer (pH 7.4) containing 150 mM NaCl. Solutions of test compounds were prepared in DMSO and serially diluted with DMSO to yield 20 µL of each of 10 solutions differing by 3-fold in concentration. Non-specific binding (NSB) using hot AMD-1 (10 µM final concentration) and total binding (TB) by using DMSO (2% final concentration). A solution of NR1A/NR2B receptors (40 pM final concentration) and tritiated AMD-2 (1 nM final concentration) were added to the test compounds. After 3 h of incubation at room temperature, samples are filtered through Packard GF/B filters (presoaked in 0.05% PEI, polyethyleninine Sigma P-3143) and washed 10 times with 1 mL of cold 20 mM Hepes buffer per wash. After vacuum drying of the filter plates, 40 µL of Packard Microscint-20 was added and bound radioactivity determined in a Packard TopCount. The apparent dissociation constant (Ki), the maximum percentage inhibition (% $I_{max}$), the minimum percentage inhibition (% $I_{min}$) and the hill slope (nH) were determined by a non-linear least squares fitting the bound CPM data to Equation #1 below.

Equation #1:

$$CPM\ Bound = \frac{(SB)(\%\ I_{max} - \%\ I_{min})}{(1 + ([Drug]/(Ki[AMD-2]/K_D))^{nH})} + NSB + (SB)(1 - \%\ I_{max})$$

where, $K_D$ is the apparent dissociation constant for the radioligand for the receptor as determined by hot saturation and SB is the specifically bound CPM determined from the difference of TB and NSB.

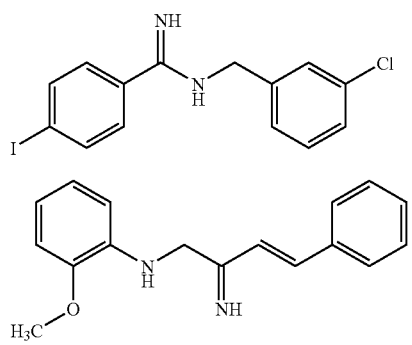

AMD-1

AMD-2

Compounds AMD-1 and AMD-2 can be synthesized in accordance with the following general reaction schemes.

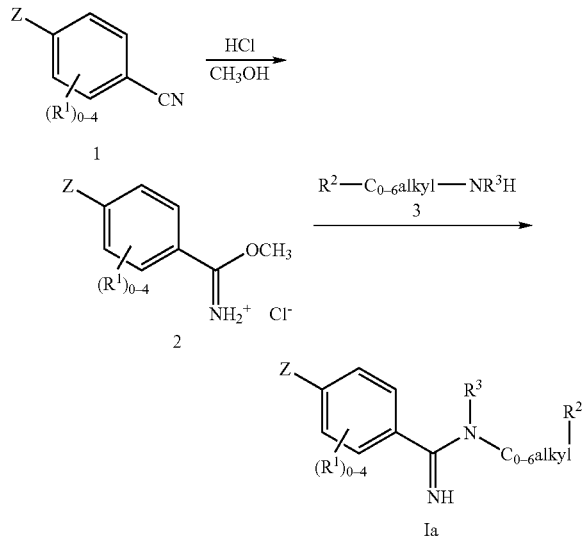

SCHEME 1

In accordance with scheme 1, hydrogen chloride is bubbled through a solution of the appropriately substituted benzonitrile 1 in methanol at room temperature. The volatiles are removed under reduced pressure and the resulting residue is triturated with ether and filtered to yield the desired imidate 2. Imidate 2 is dissolved in methanol at ambient temperature, treated with amine 3 at ambient temperature and stirred under argon. The volatiles are removed under reduced pressure and the residue purified by preparative HPLC or trituration with ether to afford amidine Ia.

SCHEME 2

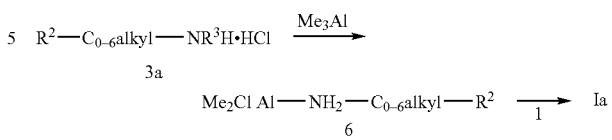

In accordance with scheme 2, at room temperature under argon, amine 3a is dissolved in ether and was treated with 1-M hydrogen chloride in ether (1 equiv.) in a single portion. The resulting precipitate is stirred vigorously for 10 minutes. The volatiles are removed under reduced pressure. The residue is suspended in toluene, cooled to 0° C. under argon, treated with 2.0-M trimethylaluminum (1.05 equiv.) in a dropwise manner, and stirred for 45 minutes at room temperature to afford intermediate 6 (not isolated). Compound 6 is added to a solution of nitrile 1 in toluene. The reaction is heated to 80° C. without stirring in a sealed tube for 18 h, cooled to ambient temperature, poured onto a silica gel column and eluted with methanol/dichloromethane to give amidine 4.

Preparation of [$^{125}$I]AMD-1

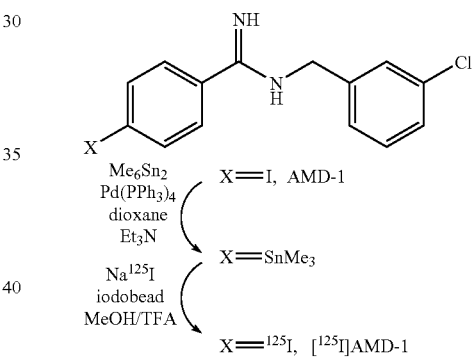

Tritiated AMD-1 was prepared by the following procedure: A mixture of AMD-1, hydrochloride salt, (5 mg, 0.012 mmol) in dioxane (0.2 mL) containing triethylamine (4 µL) was treated with hexamethylditin (5 µL), a catalytic amount of palladium catalyst and heated at 100° C. for 45 minutes. The reaction was cooled to room temperature, filtered through a glass wool plug, rinsed with methanol and concentrated in vacuo to give 10.7 mg of a brown oil. The oil was dissolved in methylene chloride and passed through a small silica column eluting with methylene chloride followed by 5% methanol/methylene chloride. Fractions containing the trimethylstannane (Rf 0.26 in 10% methanol/methylene chloride) were pooled and concentrated in vacuo to give 4.5 mg of the trimethylstannane as a clear colorless oil. This material was further purified by HPLC (C18 Econosil, 10×250 mm, 20 minute linear gradient, 30% MeCN:70% H$_2$O (0.1% TFA) to 90% MeCN, 3 mL/min, 254 nm, retention time 15 minutes) to give 3 mg of the trimethylstannane.

A Na$^{125}$I shipping vial (10 mCi, Amersham) was charged with a stir bar, an iodobead, 50 µL of methanol and stirred five minutes at room temperature. A solution of the trimethylstannane (0.1 mg) in 50 µL of methanol containing 5 µL of trifluoroacetic acid was added and the reaction was stirred for five minutes. The reaction was quenched with 50 µL of ammonium hydroxide and purified by HPLC (C18 Vydac protein and peptide column, 4.6×250 mm, 20 minute linear gradient, 30% MeCN:70% H$_2$O (0.1% TFA) to 90% MeCN, 1 mL/min, retention time 11 minutes). Fractions containing the radioactive product were pooled and concentrated in vacuo to give 989 µCi of [$^{125}$I]AMD-1 with a specific activity of 898 Ci/mmol as measured by UV absorbance at 272 nm.

Synthesis of Tritiated AMD-2

Tritiated AMD-2 was prepared by the following procedure: The phenol of AMD-2 (2 mg, 0.008 mmol) dissolved in dimethylformamide (0.6 mL) and potassium carbonate (1.2 mg) for 1 h. High specific activity tritiated methyl iodide (50 mCi, 0.0006 mmol, in toluene 1 mL, American Radiolabeled Chemicals) was added at room temperature and stirred for 2 hours. The reaction mixture was filtered using a Whatman PTFE 0.451 µm syringeless filter device to remove any insoluble potassium carbonate, washed with Abs. ethanol (2 mL, Pharmco), and the combined filtrates were concentrated to dryness at room temperature using a rotary evaporator; this also removed any unreacted tritiated methyl iodide. The residue was purified by HPLC chromatography on a Phenomenx Luna C8 semi-prep column (Luna 5 micro C8(2), 250×10.0 mm) using a-gradient system of 20/80 acetonitrile/water with 0.1% trifluoroacetic acid to 100% acetonitrile with 0.1% trifluoroacetic acid in 20 min. Total activity of the product was 8 mCi. Further purification was effected by absorption onto a Waters C-18 Sep-pak column (Waters Sep-Pak PLUS C18) and elution with water followed by absolute ethanol. The product was diluted with absolute ethanol (10 mL) before submission for final analysis.

The compounds of this invention exhibit IC$_{50}$'s of less than 50 µM in the FLIPR and binding assays. It is advantageous that the IC$_{50}$'s be less than 5 µM in the FLIPR and binding assays. It is more advantageous that the IC$_{50}$'s be less than 1 µM in the FLIPR and binding assays. It is still more advantageous that the IC$_{50}$'s be less than 0.1 µM in the FLIPR and binding assays. Thus, the compounds and pharmaceutical compositions of this invention have been found to exhibit biological activity as NMDA NR2B antagonists. Accordingly, another aspect of the invention is the treatment of pain, migraine, depression, anxiety, schizophrenia, Parkinson's disease, or stroke—maladies that are amenable to amelioration through inhibition of NMDA NR2B receptors—by the administration of an effective amount of the compounds of this invention.

Thus, pain can be treated by administering once or twice a day, a compound of this invention at 0.1 mg, 1 mg, 5 mg, 10 mg, or 25 mg per kg of body weight.

Migraine can be treated by administering once or twice a day, a compound of this invention at 0.1 mg, 1 mg, 5 mg, 10 mg, or 25 mg per kg of body weight.

Depression can be treated by administering once or twice a day, a compound of this invention at 0.1 mg, 1 mg, 5 mg, 10 mg, or 25 mg per kg of body weight.

Anxiety can be treated by administering once or twice a day, a compound of this invention at 0.1 mg, 1 mg, 5 mg, 10 mg, or 25 mg per kg of body weight.

Schizophrenia can be treated by administering once or twice a day, a compound of this invention at 0.1 mg, 1 mg, 5 mg, 10 mg, or 25 mg per kg of body weight.

Parkinson's disease can be treated by administering once or twice a day, a compound of this invention at 0.1 mg, 1 mg, 5 mg, 10 mg, or 25 mg per kg of body weight.

Stroke can be treated by administering once or twice a day, a compound of this invention at 0.1 mg, 1 mg, 5 mg, 10 mg, or 25 mg per kg of body weight.

The abbreviations used herein are as follows unless specified otherwise:

| | |
|---|---|
| BH$_3$*THF | Tetrahydrofuran/borane complex |
| BINAP | 2,2'-Bis(diphenylphosphino)-1,1'-binaphthyl |
| BOC | t-Butoxycarbonyl |
| BOC$_2$O | t-Butoxycarbonyl anhydride |
| CBZ | Carbobenyloxy |
| CBZ-Cl | Carbobenzyl chloride |
| DCM | Dichloromethane |
| DIPEA | Diisopropylethylamine |
| DMAP | 4-Dimethylaminopyridine |
| DMF | N,N-Dimethylformamide |
| DMF-DMA | Dimethylformamide-Dimethylacetal |
| DMSO | Dimethylsulfoxide |
| EDC | 3-Ethyl-3-(3-dimethylaminopropyl)carbodiimide hydrochloride |
| h | hours |
| HOAt | 1-Hydroxy-7-azabenzotriazole |
| HOBt | Hydroxybenzoxazole |
| IPA | Isopropanol |
| mCPBA | meta Chloroperbenzoic acid |
| min | minutes |
| MeCN | Acetonitrile |
| NMR | nuclear magnetic resonance |
| r.t., RT, or rt | room temperature |
| sat. | saturated |
| TEA | Triethylamine |
| TFA | Trifluoroacetic acid |
| THF | Tetrahydrofuran |

The following examples are provided to more fully illustrate the present invention, and are not to be construed as limiting the scope of the claims in any manner.

EXAMPLES

The compounds of this invention can be prepared by procedures shown below.

Intermediates:

Intermediate 1a:

Carbonic acid 2,5-dioxo-pyrrolidin-1-yl ester 4-methylbenzyl ester

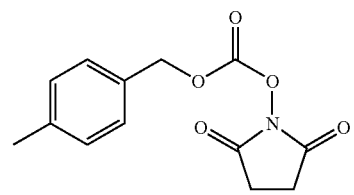

Disuccinimidyl carbonate (5.03 g, 19.65 mmol) in 30 mL MeCN and 30 mL DCM was treated with 4-methylbenzyl alcohol (2.4 g, 19.6 mmol) followed by DMAP (1.20 g, 9.82 mmol). The resulting cloudy reaction mixture cleared over 2 min, stirred overnight at rt, then poured into 100 mL water and partitioned. The organic layer was dried over anhydrous sodium sulfate and the solvent evaporated. The solid thus obtained was stirred with approx. 25 mL ether, filtered, washed with a small volume of ether and dried to yield carbonic acid 2,5-dioxo-pyrrolidin-1-yl ester 4-methyl-benzyl ester as a white solid. Ref: *Chem. Pharm. Bull.*, 38(1): 110–115 (1990).

The following compounds were prepared in the manner similar to that described above for INTERMEDIATE 1a:

Intermediate 1b:

Carbonic acid 2,5-dioxo-pyrrolidin-1-yl ester 4-chloro-benzyl ester

Intermediate 1c:

Carbonic acid 2,5-dioxo-pyrrolidin-1-yl ester 4-fluoro-benzyl ester

Intermediate 1d:

Carbonic acid 2,5-dioxo-pyrrolidin-1-yl ester 4-ethyl-benzyl ester

Intermediate 1e:

Carbonic acid 2,5-dioxo-pyrrolidin-1-yl ester 4-isopropyl-benzyl ester

Utilizing the carbonic acid derivatives described above for INTERMEDIATES 1a–1e, and following the procedure described below in EXAMPLE 13, step 1, the following INTERMEDIATES 2a–2e were obtained

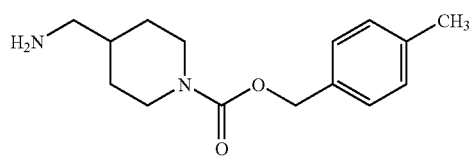

Intermediate 2a:

4-Methylbenzyl 4-(aminomethyl)piperidine-1-carboxylate

Intermediate 2b:

4-Chlorobenzyl 4-(aminomethyl)piperidine-1-carboxylate

Intermediate 2c:

4-Fluorobenzyl 4-(aminomethyl)piperidine-1-carboxylate

Intermediate 2d:

4-Ethylbenzyl 4-(aminomethyl)piperidine-1-carboxylate

Intermediate 2e:

4-Isopropylbenzyl 4-(aminomethyl)piperidine-1-carboxylate

Example 1

Benzyl 4-[(4-pyridinylamino)methyl]-1-piperidinecarboxylate

Step 1:

Benzyl 4-[(4-pyridinylamino)carbonyl]-1-piperidinecarboxylate

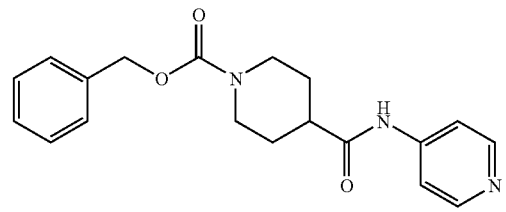

In DMF (5 mL), 1-[(benzyloxy)carbonyl]-4-piperidinecarboxylic acid (P. E. Maligres et al., *Tetrahedron*, 53:10983 (1997)) (1.00 g, 3.80 mmol), 4-aminopyridine (572 mg, 6.08 mmol), EDC (801 mg, 4.18 mmol), and HOAt (569 mg, 4.18 mmol) were combined and aged under $N_2$ for 4 h. The reaction was partitioned between sat. $NaHCO_3$ and ethyl acetate. The layers were separated and the aqueous layer was extracted with ethyl acetate (2×). The combined organics were washed with water and brine then dried over $Na_2SO_4$, filtered and concentrated under reduced pressure, affording 1.16 g of benzyl 4-[(4-pyridinylamino)carbonyl]-1-piperidinecarboxylate as a yellow oil which was used without further purification.

Step 2:

Benzyl 4-[(4-pyridinylamino)methyl]-1-piperidinecarboxylate

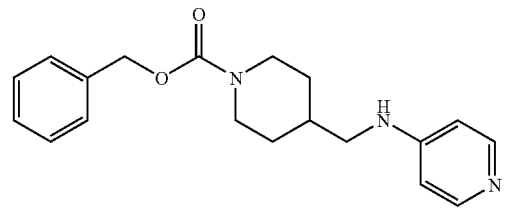

The amide prepared as described in Step 1 above (17.82 g, 52.50 mmol) was dissolved in THF (50 mL) and was treated with $BH_3$-THF (200 mmol, 200 mL, 1M in THF) over 10 min. and was aged at r.t. 3 h. The reaction was quenched by slowly adding 2N HCl and stirring vigorously 15 h. The reaction was basified with 1M NaOH and extracted with ethyl acetate (3×). The combined organics were washed with brine, dried over $Na_2SO_4$, filtered and concentrated in vacuo, yielding a white foam which was purified by silica gel chromatography (99:1:0.1 to 90:10:1 $CH_2Cl_2$:$CH_3OH$:$NH_4OH$) to give 11.53 g of benzyl 4-[(4-pyridinylamino)methyl]-1-piperidinecarboxylate as a viscous pale yellow oil.

$^1$H NMR (HCl salt 400 MHz, $CD_3OD$): δ 8.09 (brs, 1H, Pyr-H), 7.97 (brs, 1H, Pyr-H), 7.35–7.28 (m, 5H, Ar—H), 6.88 (brs, 2H, Pyr-H), 5.11 (s, 2H, CH$_2$—Ar), 4.18 (brd, J=11.70 Hz, 2H, CHH), 3.25 (d, J=6.77 Hz, 2H, CH$_2$—N), 2.86 (brs, 2H, CHH), 1.90–1.77 (m, 3H, CHH, CH), 1.29–1.16 (dq, J=12.36 Hz, 4.16 Hz, 2H, CHH).

M.S. (M+1): 326.47.

Example 2

4-[(3-Methylpyridin-4-ylamino)methyl]piperidine-1-carboxylic acid benzyl ester

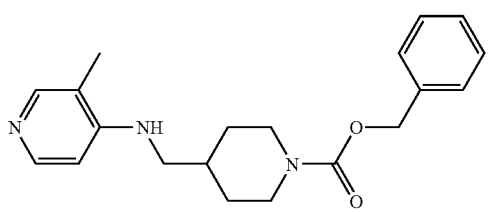

The title compound was prepared as described in EXAMPLE 1, but replacing 4-aminopyridine with 4-amino-3-methylpyridine (Malinowski et al., *J. Prakt. Chem.*, 330: 154–158 (1988)).

$^1$H NMR (400 MHz, CD$_3$OD): δ 7.74 (d, J=5.85 Hz, 1H, Pyr-H), 7.66 (brs, 1H, Pyr-H), 7.36–7.29 (m, 5H, Ar—H), 6.77 (brs, 1H, Pyr-H), 5.11 (s, 2H, CH$_2$—Ar), 4.19 (brd, J=13.81 Hz, 3H), 3.31–3.20 (m, 2H, CH$_2$—N+CH3OH), 2.84 (brs, 2H, CHH), 2.22 (brs, 2H, CHH), 1.98–1.85 (m, 1H, CH), 1.82 (brd, J=12.89 Hz, 2H, CHH), 1.22–1.14 (m, 2H, CHH).

M.S. (M+1): 340.27.

Example 3

Benzyl 4-{[(2-pyridinyl)amino]methyl}-1-piperidinecarboxylate

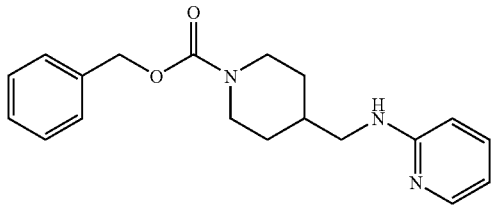

The title compound was prepared as described in EXAMPLE 1, but replacing 4-aminopyridine with 2-aminopyridine.

$^1$H NMR (400 MHz, CD$_3$OD): δ 10.00 (brs, 1H, NH), 7.82–7.75 (m, 2H, Pyr-H, Pyr-H), 7.38–7.30 (m, 5H, Ar—H), 6.76–6.70 (m, 2H, Pyr-H, Pyr-H), 5.12 (s, 2H, CH$_2$—Ar), 4.24 (brs, 2H, CHH), 3.16 (brs, 2H, CH$_2$—N), 2.84 (brs, 2H, CHH), 2.01–1.80 (m, 3H, CH, CHH+H2O), 1.26–1.18 (m, 2H, CHH).

M.S. (M+1): 326.28.

Example 4

Benzyl 4-{[(3-pyridinyl)amino]methyl}-1-piperidinecarboxylate

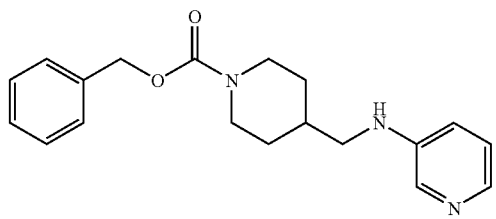

The title compound was prepared as described in EXAMPLE 1, but replacing 4-aminopyridine with 3-aminopyridine.

$^1$H NMR (500 MHz, CD$_3$OD): δ 8.01 (d, J=2.93 Hz, 1H, Pyr-H), 7.95 (dd, J=4.63 Hz, 1.46 Hz, 1H, Pyr-H), 7.37–7.30 (m, 5H, Ar—H), 7.08 (dd, J=8.30 Hz, 4.59 Hz, 1H, Pyr-H), 6.86–6.84 (m, 1H, Pyr-H), 5.13 (s, 2H, CH$_2$—Ar), 4.25 (brs, 2H, CHH), 3.80 (brt, J=5.86 Hz, 1H, NH), 3.04 (t, J=6.33 Hz, 2H, CH$_2$—N), 2.78 (brs, 2H, CHH), 1.78 (brs, 3H, CH, CHH+H2O), 1.27–1.13 (m, 2H, CHH).

M.S. (M+1): 326.31.

Example 5

Benzyl 4-{[(4-methyl-2-pyridinyl)amino]methyl}-1-piperidinecarboxylate

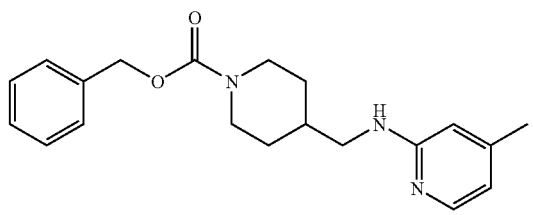

The title compound was prepared as described in EXAMPLE 1, but replacing 4-aminopyridine with 2-amino-4-methylpyridine (Fluka Co.). M.S. (M+1): 340.40.

Example 6

Benzyl 4-{[(4-ethyl-2-pyridinyl)amino]methyl}-1-piperidinecarboxylate

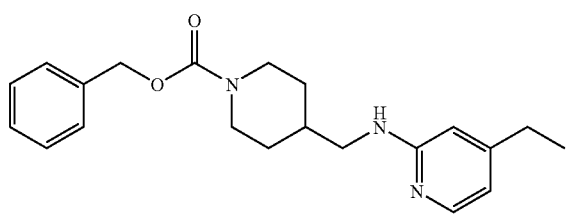

The title compound was prepared as described in EXAMPLE 1, but replacing 4-aminopyridine with 2-amino-4-ethylpyridine (Maybridge Chemicals). M.S. (M+1): 354.41.

Example 7

Benzyl 4-[(3-isoxazolylamino)methyl]-1-piperidinecarboxylate

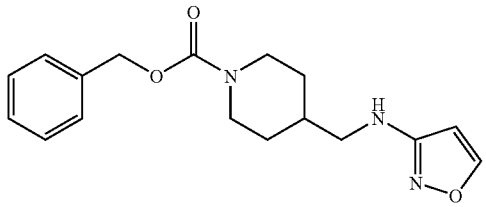

The title compound was prepared as described in EXAMPLE 1, but replacing 4-aminopyridine with 3-aminoisoxazole (Sigma-Aldrich Co.). M.S. (M+1): 316.29.

Example 8

Benzyl 4-[(1,3,4-thiadiazol-2-ylamino)methyl]-1-piperidinecarboxylate

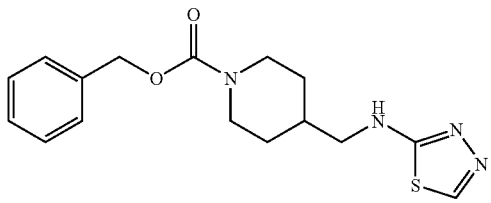

The title compound was prepared as described in EXAMPLE 1, but replacing 4-aminopyridine with 2amino-1,3,4-thiadiazole. M.S. (M+1): 333.35.

Example 9

Benzyl 4-{[(5-methyl-2-pyridinyl)amino]methyl}-1-piperidinecarboxylate

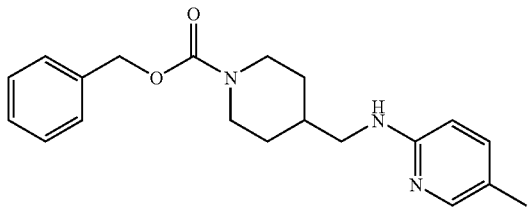

The title compound was prepared as described in EXAMPLE 1, but replacing 4-aminopyridine with 2-amino-5-methylpyridine. M.S. (M+1): 340.40.

Example 10

Benzyl 4-{[(1-methyl-1H-imidazole-2-yl)amino]methyl}-1-piperidinecarboxylate

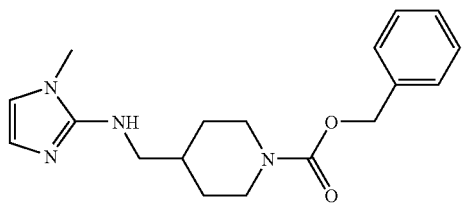

The title compound was prepared as described in EXAMPLE 1, step 1, but replacing 4-aminopyridine with 2-amino-imidazole hemisulfate and gave the EDC coupling product. This product was refluxed in DMF-DMA for 90 min., diluted with ethyl acetate, washed with sat. NaHCO$_3$, dried over Na$_2$SO$_4$, filtered and then concentrated under reduced pressure. The resulting red oil was purified by silica gel chromatography. 50 mg (mmol) of the purified product was reacted with borane as described in EXAMPLE 1, step 2, to give 26 mg of benzyl 4-{[(1-methyl-1H-imidazol-2-yl)amino]methyl}-1-piperidinecarboxylate.

$^1$H NMR (400 MHz, CDCl$_3$): δ 7.36–7.27 (m, 5H, Ar—H), 6.65 (d, J=1.55 Hz, 1H, imidazole-H), 6.49 (d, J=1.56 Hz, 1H, imidazole-H), 5.12 (s, 2H, CH$_2$—Ar), 4.19 (brs, 2H, CHH), 3.58 (brs, 1H, NH), 3.34 (s, 3H, CH$_3$), 3.23 (m, 2H, CH$_2$—N), 2.79 (brs, 2H, CHH), 1.85–1.70 (m, 3H, CHH, CH), 1.23–1.13 (m, 2H, CHH).

M.S. (M+1): 329.27.

Example 11

4-(Quinolin-4-ylaminomethyl)-piperidine-1-carboxylic acid benzyl ester

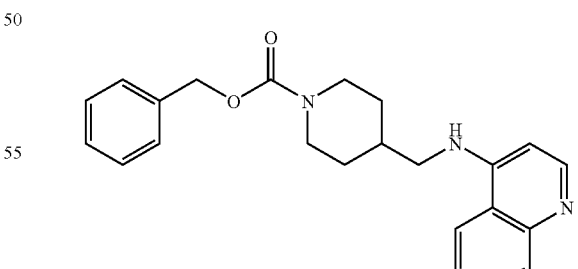

The title compound was prepared as described in EXAMPLE 1, replacing 4-aminopyridine with 4-aminoquinoline. M.S. (M+1): 376.39.

Example 12

Benzyl 4-{[(1-oxido-4-pyridinyl)amino]methyl}-1-piperidinecarboxylate

Step 1:

Benzyl 4-{[(1-oxido-4-pyridinyl)amino]carbonyl}-1-piperidinecarboxylate

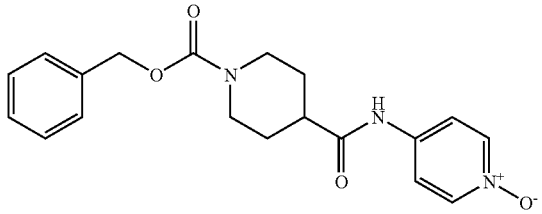

Benzyl 4-[(4-pyridinylamino)carbonyl]-1-piperidinecarboxylate (EXAMPLE 1, Step 1) (615 mg, 1.81 mmol) was dissolved in CH$_2$Cl$_2$ and treated with mCPBA (3.12 g, 18.10 mmol) and aged 18 h. The reaction was diluted with ethyl acetate and washed with sat. NaHCO$_3$. The organics were separated, dried over Na$_2$SO$_4$, filtered and concentrated under reduced pressure. The resulting oil was purified by silica gel chromatography to afford benzyl 4-{[(1-oxido-4-pyridinyl)amino]carbonyl}-1-piperidinecarboxylate as a clear oil.

$^1$H NMR (400 MHz, CDCl$_3$): δ 10.72 (s, 1H, NH), 8.03 (d, J=7.50 Hz, 2H, Pyr-H), 7.80 (d, J=7.50 Hz, 2H, Pyr-H), 7.38–7.28 (m, 5H, Ar—H), 5.12 (s, 2H, CH$_2$—Ar), 4.18 (brd, J=13.25 Hz, 2H, CHH), 2.81 (brs, 2H, CHH), 2.57–2.45 (m, 1H, CH), 1.86–1.68 (m, 4H, CHH, CHH).

M.S. (M+1): 356.28.

Step 2:

Benzyl 4-{[(1-oxido-4-pyridinyl)amino]methyl}-1-piperidinecarboxylate

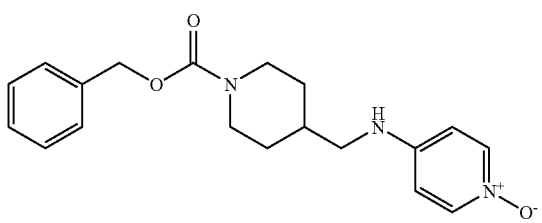

Benzyl 4-{[(1-oxido-4-pyridinyl)amino]carbonyl}-1-piperidinecarboxylate (62 mg, 0.17 mmol) was reduced with borane as described in EXAMPLE 1, step 2, to afford benzyl 4-{[(1-oxido-4-pyridinyl)amino]methyl}-1-piperidinecarboxylate as a clear oil.

$^1$H NMR (400 MHz, CDCl$_3$): δ 7.99 (d, J=7.31 Hz, 2H, Pyr-H), 7.88 (brs, 1H, NH), 7.38–7.30 (m, 5H, Ar—H), 6.66 (brs, 2H, Pyr-H), 5.12 (s, 2H, CH$_2$—Ar), 4.22 (brs, 2H, CHH), 3.09 (brs, 2H, CH$_2$—N), 2.77 (brs, 2H, CHH), 1.87–1.71 (m, 3H, CHH, CH), 1.26–1.11 (m, 2H, CHH).

M.S. (M+1): 342.33.

Example 13

Benzyl 4-[(9H-purin-6-ylamino)methyl]-1-piperidinecarboxylate

Step 1:

Benzyl 4-(aminomethyl)piperidine-1-carboxylate

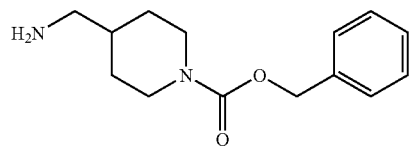

4-Aminomethylpiperidine (40 g, 350 mmol) and benzaldehyde (37.3 mL, 368 mmol) in toluene (600 mL) were heated to reflux under Dean Stark conditions for 2 h. The resulting reaction mixture was cooled to room temperature and 500 mL dichloromethane was added. The resulting solution was cooled to 5° C. and treated with N-(benzyloxycarbonyloxy)succinimide (91.7 g, 368 mmol). After 10 min, the cooling bath was removed and the resulting reaction mixture stirred for 1 h. The solvents were evaporated and the residue stirred with 400 mL THF and 400 mL 2M HCl for 1 h. The mixture was concentrated to remove organics and extracted with ether (3×300 mL). The aqueous phase was adjusted to pH14 with 50% NaOH and extracted with ethyl acetate. The organic layer was washed with water and brine, dried over anhydrous sodium sulfate, and the solvent evaporated to give benzyl 4(aminomethyl)piperidine-1-carboxylate as an oil.

$^1$H NMR (500 MHz CDCl$_3$) δ: 7.4–7.2 (m, 5H); 5.12 (s, 2H); 4.20 (brs, 2H); 2.77 (brs, 2H); 2.58 (d, J=6.6 Hz, 2H) 1.9–1.7 (m, 2H); 1.0–1.5 (m, 5H).

Step 2:

Benzyl 4-[(9H-purin-6-ylamino)methyl]-1-piperidinecarboxylate

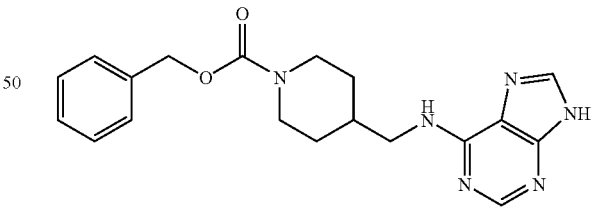

In DMF (5 mL), benzyl 4-(aminomethyl)-1-piperidinecarboxylate (1.20 g, 4.83 mmol) and 6-chloropurine (448 mg, 2.49 mmol) were combined and treated with TEA in a single portion and aged under N$_2$ at 100° C. for 18 h. The resulting reaction was diluted with sat. NaHCO$_3$ and extracted with ethyl acetate (3×). The combined organics were washed with brine, dried over Na$_2$SO$_4$, filtered and concentrated in vacuo to give a brown oil which was purified by silica gel chromatography (20 g, 32–60 μm silica, 99:1:0.1 to 90:10:1 CH$_2$Cl$_2$:CH$_3$OH:NH$_4$OH) to give benzyl 4-[(9H-purin-6-ylamino)methyl]-1-piperidinecarboxylate as a brown oil.

¹H NMR (400 MHz, CDCl₃): δ 8.42 (s, 1H, purine-H), 7.97 (s, 1H, purine-H), 7.36–7.29 (m, 5H, Ar—H), 6.21 (brs, 1H), 5.13 (s, 2H, CH₂—Ar), 4.22 (brs, 2H, CHH), 3.43 (brs, 2H, CH₂—N), 2.80 (brs, 2H, CHH), 1.95–1.79 (m, 3H, CHH, CH), 1.34–1.21 (m, 2H, CHH).

M.S. (M+1): 367.31.

Example 14

4-Methylbenzyl 4-[(4-pyrimidinylamino)methyl]-1-piperidinecarboxylate

Step 1:

4-[(2-Methylsulfanyl-pyrimidin-4-ylamino)-methyl]-piperidine-1-carboxylic acid 4-methyl-benzyl ester

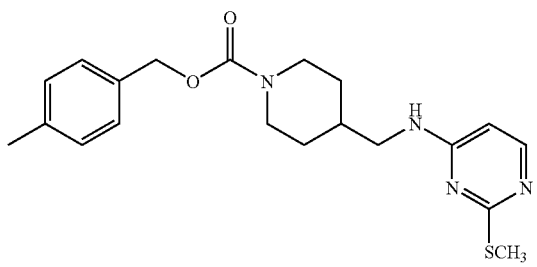

The 4-[(2-methylsulfanyl-pyrimidin-4-ylamino)-methyl]-piperidine-1-carboxylic acid 4-methyl-benzyl ester was prepared as described in EXAMPLE 13, Step 2, but replacing 6-chloropurine with 4-chloro-2-methylthiopyrimidine and replacing benzyl 4-(aminomethyl)-1-piperidinecarboxylate with 4-methylbenzyl 4-(aminomethyl)-1-piperidinecarboxylate. M.S. (M+1): 387

Step 2:

4-Methylbenzyl 4-[(4-pyrimidinylamino)methyl]-1-piperidinecarboxylate

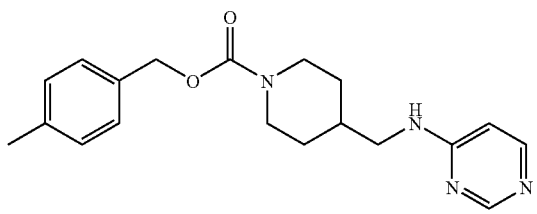

4-[(2-Methylsulfanyl-pyrimidin-4-ylamino)-methyl]-piperidine-1-carboxylic acid 4-methyl-benzyl ester (550 mg, 1.42 mmol)was dissolved in EtOH (15 mL) and treated with Raney Nickel (834 mg, 14.20 mmol) at room temperature for 3 h, filtered, concentrated and purified by silica gel chromatography to give EXAMPLE 14 as a yellow oil.

¹H NMR (400 MHz, CDCl₃): δ 8.53 (s, 1H, Pyr-H), 8.13 (brd, J=4.48 Hz, 1H, Pyr-H), 7.24 (d, J=7.86 Hz, 2H, Ar—H), 7.16 (d, J=7.68 Hz, 2H, Ar—H), 6.31 (dd, J=6.00 Hz, 1.20 Hz, 1H, Pyr-H), 5.57 (s, 1H, NH), 5.08 (s, 2H, CH₂—Ar), 4.20 (brs, 2H, CHH), 3.23 (brs, 2H, CH₂—N), 2.75 (brs, 2H, CHH), 2.34 (s, 3H, CH₃), 1.82–1.65 (m, 3H, CHH, CH), 1.23–1.09 (m, 2H, CHH).

M.S. (M+1): 341.35.

Example 15

Benzyl 4-[(4-pyrimidinylamino)methyl]-1-piperidinecarboxylate

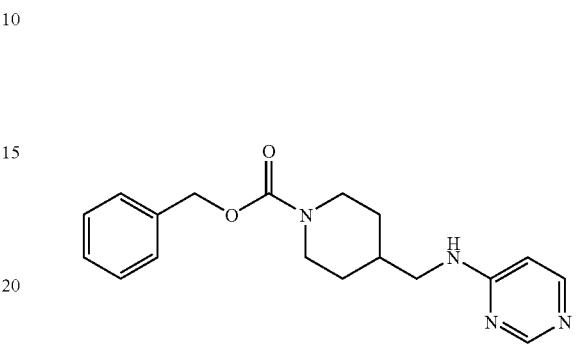

The title compound was prepared as described in EXAMPLE 14, but replacing 4-methylbenzyl 4-(aminomethyl)-1-piperidinecarboxylate with benzyl 4-(aminomethyl)-1-piperidinecarboxylate.

¹H NMR (400 MHz, CDCl₃): δ 8.53 (s, 1H, Pyr-H), 8.13 (brd, J=4.85 Hz, 1H, Pyr-H), 7.38–7.28 (m, 5H, Ar—H), 6.32 (d, J=6.03 Hz, 1H, Pyr-H), 5.51 (brs, 1H, NH), 5.12 (s, 2H, CH₂—Ar), 4.21 (brs, 2H, CHH), 3.24 (brs, 2H, CH₂—N), 2.77 (brs, 2H, CHH), 1.85–1.70 (m, 3H, CHH, CH), 1.27–1.10 (m, 2H, CHH).

M.S. (M+1): 327.29.

Example 16

Benzyl 4-[(2-pyrimidinylamino)methyl]-1-piperidinecarboxylate

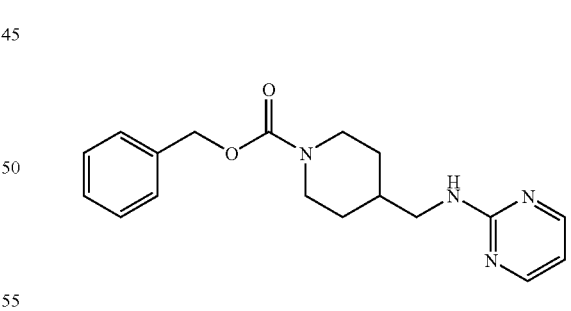

The title compound was prepared as described in EXAMPLE 13, except using benzyl 4-(aminomethyl)-1-piperidinecarboxylate (6.50 g, 26.19 mmol) and 2-chloropyrimidine (990 mg, 8.64 mmol) as starting materials without a solvent to give the title compound as a yellow oil.

¹H NMR (400 MHz, CDCl₃): δ 8.26 (d, J=4.85 Hz, 1H, Pyr-H), 7.36–7.29 (m, 5H, Ar—H), 6.52 (t, J=4.85 Hz, 1H, Pyr-h), 5.12 (s, 2H, CH₂—Ar), 4.21 (brs, 2H, CHH), 3.30 (t, J=6.26 Hz, 2H, CH₂—N), 2.78 (brs, 2H, CHH), 1.76–1.62 (m, 3H, CHH, CH), 1.28–1.12 (m, 2H, CHH).

M.S. (M+1): 327.33.

Example 17

4-Methylbenzyl 4-[(2-pyrimidinylamino)methyl]-1-piperidinecarboxylate

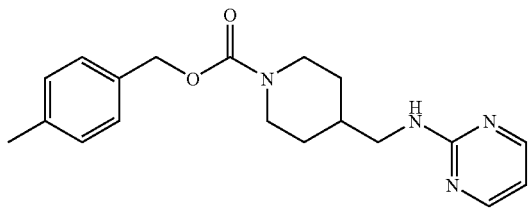

The title compound was prepared as described in EXAMPLE 13, except using 4-methylbenzyl 4-(aminomethyl)-1-piperidinecarboxylate (300 mg, 1.14 mmol), 2-chloropyrimidine (131 mg, 1.14 mmol) as starting materials gave the title compound as a yellow oil.

$^1$H NMR (400 MHz, CDCl$_3$): δ 8.26 (d, J=4.76, 2H, Pyr-H), 7.26 (d, J=8.96 Hz, 2H, Ar—H), 7.17 (d, J=8.96 Hz, 2H, Ar—H), 6.31 (dd, J=4.85 Hz, 1H, Pyr-H), 5.28 (s, 1H, NH), 5.08 (s, 2H, CH$_2$—Ar), 4.19 (brs, 2H, CHH), 3.32 (d, J=6.36 Hz, 2H CH$_2$—N), 2.76 (brs, 2H, CHH), 2.35 (s, 3H, CH$_3$), 1.82–1.60 (m, 3H, CHH, CH), 1.25–1.13 (m, 2H, CHH).

M.S. (M+1): 341.37.

Example 18

Benzyl 4-{[(5-methyl-2-pyrimidinyl)amino]methyl}-1-piperidinecarboxylate

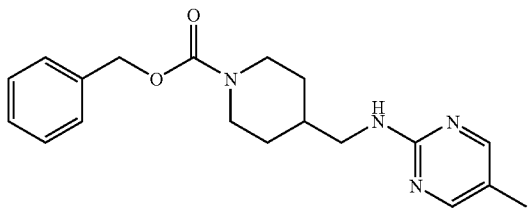

The title compound was prepared as described in EXAMPLE 13, except using benzyl 4-(aminomethyl)-1-piperidinecarboxylate (298 mg, 1.20 mmol), 2-chloro-5-methylpyrimidine (EXAMPLE 144, Step 1) (51 mg, 0.40 mmol) as starting materials and using no solvent and gave the title compound as a yellow oil.

$^1$H NMR (400 MHz, CDCl$_3$): δ 8.10 (s, 2H, Pyr-H), 7.36–7.28 (m, 5H, Ar—H), 5.47 (bt, J=4.98 Hz, 1H, NH), 5.12 (s, 2H, CH$_2$—Ar), 4.19 (brs, 2H, CHH), 3.32 (d, J=6.22 Hz, 2H, CH$_2$—N), 2.76 (brs, 2H, CHH), 2.10 (s, 3H, CH$_3$), 1.82–1.63 (m, 3H, CHH, CH), 1.25–1.12 (m, 2H, CHH).

M.S. (M+1): 341.40.

Example 19

4-Methylbenzyl 4-({[2-(methylsulfanyl)-4-pyrimidinyl]amino}methyl)-1-piperidinecarboxylate

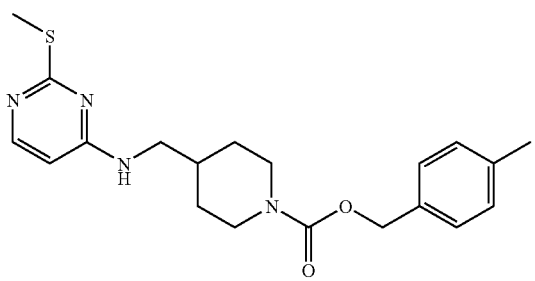

The title compound was prepared as described in EXAMPLE 13, except using 4-methylbenzyl 4-(aminomethyl)-1-piperidinecarboxylate (600 mg, 2.29 mmol), and 4-chloro-2-methylthiopyrimidine (386 mg, 2.40 mmol) as starting materials and gave the title compound as a yellow oil.

$^1$H NMR (400 MHz, CDCl$_3$): δ 7.99 (bs, 1H, Pyr-H), 7.25 (d, J=8.69 Hz, 2H, Ar—H), 7.17 (d, J=8.95 Hz, 2H, Ar—H), 6.00 (d, J=5.94 Hz, 1H, Pyr-H), 5.08 (s, 2H, CH$_2$—Ar), 4.97 (bs, 1H, NH), 4.21 (brs, 2H, CHH), 3.24 (brs, 2H, CH$_2$—N), 2.75 (brs, 2H, CHH), 2.48 (s, 3H, CH$_3$), 2.35 (s, 3H, CH$_3$), 1.82–1.65 (m, 3H, CHH, CH), 1.27–1.12 (m, 2H, CHH).

M.S. (M+1): 387.34.

Example 20

Benzyl 4-{[(6-chloro-4-pyrimidinyl)amino]methyl}-1-piperidinecarboxylate

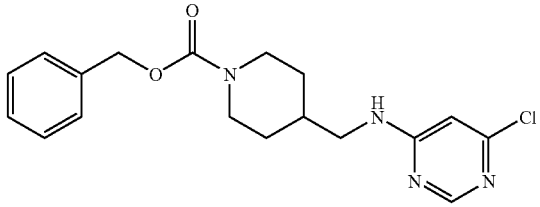

The title compound was prepared as described in EXAMPLE 13, except using 4,6-dichloropyrimidine (1.26 g, 8.45 mmol) in place of 6-chloropurine as starting materials and adding TEA (2.80 mL, 20.13 mmol) in 10 mL DMF. The procedure gave the title compound as a yellow oil.

$^1$H NMR (400 MHz, CDCl$_3$): δ 8.32 (s, 1H, Pyr-H), 7.37–7.28 (m, 5H, Ar—H), 6.35 (s, 1H, Pyr-H), 5.72 (s, 1H, NH), 5.13 (s, 2H, CH$_2$—Ar), 4.22 (brs, 2H, CHH), 3.23 (brs, 2H, CH$_2$—N), 2.78 (brs, 2H, CHH),1.85–1.66 (m, 3H, CHH, CH), 1.27–1.10 (m, 2H, CHH).

M.S. (M+1): 361.32.

Example 21

Benzyl 4-{[(2-amino-9H-purin-6-yl)amino]methyl}-1-piperidinecarboxylate

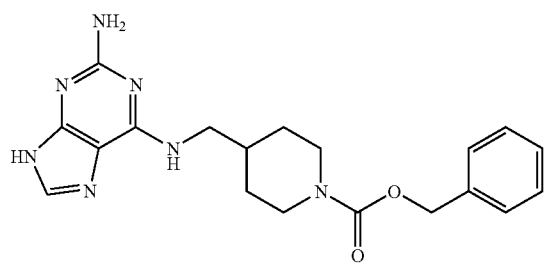

The title compound was prepared as described in EXAMPLE 13, except using benzyl 4-(aminomethyl)-1-piperidinecarboxylate (300 mg, 1.21 mmol) and 4-amino-6-chloropurine (68 mg, 0.40 mmol) as starting material. The procedure gave the title compound as a yellow oil.

$^1$H NMR (400 MHz, CDCl$_3$): δ 7.60 (s, 1H, purine-H), 7.38–7.28 (m, 5H, Ar—H), 6.01 (vbs, 1H, NH), 5.12 (s, 2H, CH$_2$—Ar), 4.86 (vbs, 2H, NH$_2$), 4.19 (brs, 2H, CHH), 3.48 (brs, 2H, CH$_2$—N), 2.77 (brs, 2H, CHH),1.88–1.70 (m, 3H, CHH, CH), 1.30–1.13 (m, 2H, CHH).

M.S. (M+1): 382.31.

Example 22

Benzyl 4-{[(6-chloro-3-pyridazinyl)amino]methyl}-1-piperidinecarboxylate

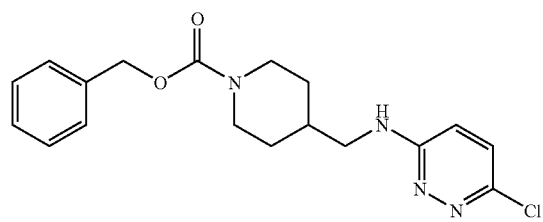

The title compound was prepared as described in EXAMPLE 13, except using benzyl 4-(aminomethyl)-1-piperidinecarboxylate (1.08 g, 4.34 mmol), 3,6-dichloropyridiazine (636 mg, 4.34 mmol) as starting materials which gave the title compound as a yellow oil.

$^1$H NMR (400 MHz, CDCl$_3$): δ 7.38–7.28 (m, 6H, Pyr-H, Ar—H), 7.15 (d, J=9.24 Hz, 1H, Pyr-H), 5.12 (s, 2H, CH$_2$—Ar), 4.89 (bs, 1H, NH), 4.22 (brs, 2H, CHH), 3.32 (brs, 2H, CH$_2$—N), 2.78 (brs, 2H, CHH), 1.96–1.82 (m, 1H, CH), 1.77 (brd, J=12.34 Hz, 2H,CHH), 1.27–1.12 (m, 2H, CHH).

M.S. (M+1): 361.27.

Example 23

Benzyl 4-[(3-pyridazinylamino)methyl]-1-piperidinecarboxylate

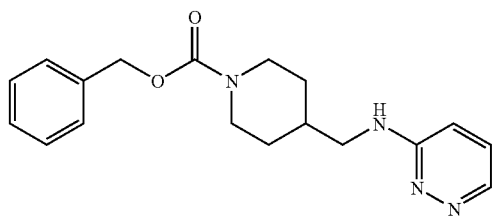

Benzyl 4-{[(6-chloro-3-pyridazinyl)amino]methyl}-1piperidinecarboxylate (EXAMPLE 22) (400 mg, 1.11 mmol) was dissolved in absolute ethanol. Raney nickel (65 mg, 1.11 mmol) was then added and the resulting reaction was stirred under 1 atm hydrogen for 18 h. The catalyst was filtered and the filtrate was concentrated under reduced pressure. The resulting clear oil was purified by silica gel chromatography to give the title compound as a clear oil.

$^1$H NMR (400 MHz, CDCl$_3$): δ 8.54 (dd, J=4.48 Hz, 1.28 Hz, 1H, Pyr-H), 7.38–7.29 (m, 5H, Ar—H), 7.14 (dd, J=9.05 Hz, 4.48 Hz, 1H, Pyr-H), 6.61 (dd, J=8.96 Hz, 1.28 Hz, 1H, Pyr-H), 5.12 (s, 2H, CH$_2$—Ar), 4.83 (bs, 1H, NH), 4.22 (brs, 2H, CHH), 3.33 (brs, 2H, CH$_2$—N), 2.78 (brs, 2H, CHH), 1.96–1.71 (m, 3H, CHH,CH), 1.27–1.12 (m, 2H, CHH).

M.S. (M+1): 327.25.

Example 24

Benzyl 4-{[(6-hydroxy-3-pyridazinyl)amino]methyl}-1-piperidinecarboxylate

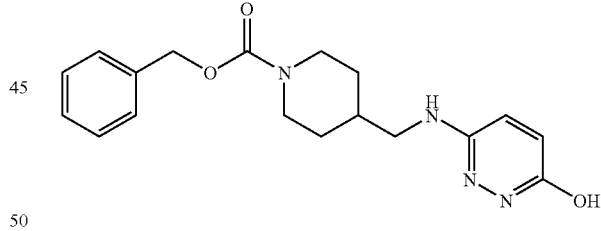

Benzyl 4-{[(6-chloro-3-pyridazinyl)amino]methyl}-1-piperidinecarboxylate (EXAMPLE 22) (37 mg, 0.10 mmol) was dissolved in acetic acid (5 mL) with sodium acetate (82 mg, 1.00 mmol) and was heated to 100° C. for 18 h. The volatiles were removed under reduced pressure and the residue partitioned between sat. NaHCO3 and ethyl acetate. The organics were dried over Na$_2$SO$_4$, filtered and concentrated under reduced pressure, affording the title compound as a clear oil.

$^1$H NMR (400 MHz, CDCl$_3$): δ 10.78 (brs, 1H, OH), 7.38–7.29 (m, 5H, Ar—H), 6.83 (d, J=10.01 Hz, 1H, Pyr-H), 6.78 (d, J=9.77 Hz, 1H, Pyr-H), 5.12 (s, 2H, CH$_2$—Ar), 4.20 (brs, 3H, CHH, NH), 3.11 (brs, 2H, CH$_2$—N), 2.78 (brs, 2H, CHH), 1.87–1.65 (m, 3H, CHH,CH), 1.23–1.13 (m, 2H, CHH).

M.S. (M+1): 343.34.

Example 25

4-(Pyrazin-2-ylaminomethyl)-piperidine-1-carboxylic acid benzyl ester

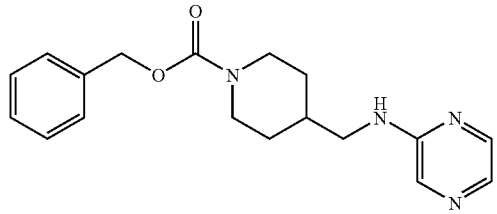

Benzyl 4-formyl-1-piperidinecarboxylate (P. E. Maligres, *Tetrahedron*, 53(32):10983–10992(1997)) (100 mg, 0.40 mmol) and aminopyrazine (46 mg, 0.48 mmol) were dissolved in toluene under $N_2$ and was heated to reflux under Dean Stark conditions for 18 h. The volatiles were removed in vacuo and the residue taken up in ethanol and treated with solid $NaBH_4$ (76 mg, 2.00 mmol) in small portions. The reaction aged at 20° C. for 1 h then was quenched with 2N HCl. The reaction was basified with 1M NaOH and was extracted with ethyl acetate (2×). The combined organics were dried over $Na_2SO_4$, filtered and concentrated in vacuo. The resulting residue was purified by reverse phase HPLC to give the title compound as a yellow oil.

$^1$H NMR (400 MHz, $CD_3OD$): δ 8.08 (d, J=1.01 Hz, 1H, Pyr-H), 7.95 (dd, J=3.29 Hz, 1.37 Hz, 1H, Pyr-H), 7.71 (d, J=3.29 Hz, 1H, Pyr-H), 7.35–7.28 (m, 5H, Ar—H), 5.10 (s, 2H, $CH_2$—Ar), 4.18–4.14 (m, 2H, CHH), 3.27 (d, J=2.14 Hz, 2H, $CH_2$—N), 2.83 (brs, 2H, CHH), 1.88–1.65 (m, 3H, CHH, CH), 1.23–1.09 (m, 2H, CHH).

M.S. (M+1): 327.26.

Example 26

Benzyl 4-[(1,3-thiazol-2-ylamino)methyl]-1-piperidinecarboxylate

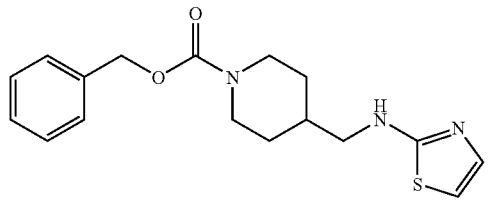

The title compound was prepared as described in EXAMPLE 25, except using benzyl 4-formyl-1-piperidinecarboxylate (300 mg, 1.21 mmol) and 2-amino-1,3-thiazole (133 mg, 1.33 mmol) as starting materials to give the title compound as a yellow oil.

$^1$H NMR (400 MHz, $CDCl_3$): δ 7.38–7.28 (m, 5H, Ar—H), 7.07 (d, J=3.66 Hz, 1H, thiazole-H), 6.45 (d, J=3.66 Hz, 1H, thiazole-H), 6.39 (brs, 1H, NH), 5.12 (s, 2H, $CH_2$—Ar), 4.20 (brs, 2H, CHH), 3.15 (d, J=6.58 Hz, 2H, $CH_2$—N), 2.77 (brs, 2H, CHH),1.89–1.71 (m, 3H, CHH, CH), 1.26–1.10 (m, 2H, CHH).

M.S. (M+1): 332.34.

Example 27

4-Methylbenzyl 4-{[(3-methyl-2-pyridinyl)amino]methyl}-1-piperidinecarboxylate

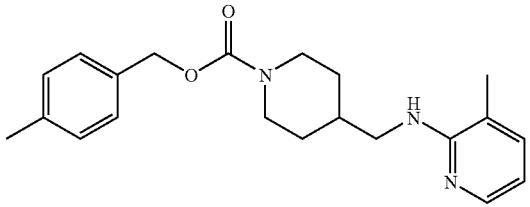

Step 1:

Benzyl 4-{[(3-methyl-2-pyridinyl)amino]carbonyl}-1-piperidinecarboxylate

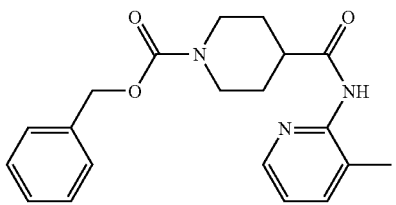

The benzyl 4-{[(3-methyl-2-pyridinyl)amino]carbonyl}-1-piperidinecarboxylate was prepared as described in EXAMPLE 1, except that 1-[(benzyloxy)carbonyl]-4-piperidinecarboxylic acid (5.00 g, 18.99 mmol), 2-amino-3-methylpyridine (2.16 g, 19.94 mmol), EDC (4.37 g, 22.79 mmol), and HOAt (2.71 g, 19.94 mmol) and DMF (3 mL) were used as starting materials. Benzyl 4-{[(3-methyl-2-pyridinyl)amino]carbonyl}-1-piperidine was isolated as an off-white solid and used without further purification.

Step 2:

Piperidine-4-carboxylic acid (3-methyl-pyridin-2-yl)-amide

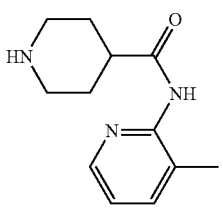

Benzyl 4-{[(3-methyl-2-pyridinyl)amino]carbonyl}-1-piperidinecarboxylate from Step 1 above (5.45 g, 15.42 mmol) was suspended in absolute ethanol (250 mL) and was treated with 10% palladium on carbon (1.50 g) and stirred vigorously for 18 h under 1 atm of hydrogen. The catalyst was filtered off and the filtrate was concentrated under reduced pressure giving the piperidine-4-carboxylic acid (3-methyl-pyridin-2-yl)-amide as yellow oil.

Step 3:

4-(3-Methyl-pyridin-2-ylcarbamoyl)-piperidine-1-carboxylic acid 4-methyl-benzyl ester

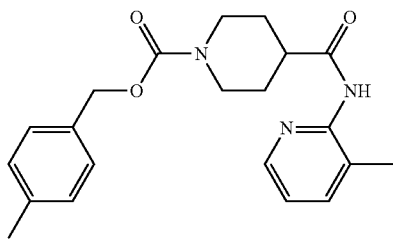

Piperidine-4-carboxylic acid (3-methyl-pyridin-2-yl)-amide from Step 2 above (100 mg, 0.46 mmol) and N-[4-(methylbenzyloxy)-carbonyloxy]succinimide (127 mg, 0.48 mmol) were combined in DMF at r.t. and were stirred vigorously for 15 min. The resulting reaction mixture was then purified by reverse phase preparatory HPLC to give 4-(3-methyl-pyridin-2-ylcarbamoyl)-piperidine-1-carboxylic acid 4-methyl-benzyl ester as a clear oil.

Step 4:

4-[(3-Methyl-pyridin-2-ylamino)-methyl]-piperidine-1-carboxylic acid 4-methyl-benzyl ester

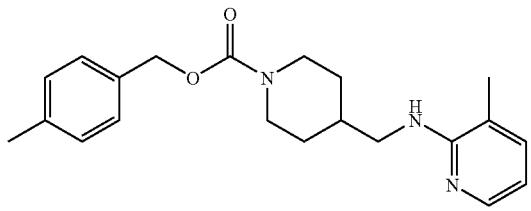

4-(3-Methyl-pyridin-2-ylcarbamoyl)-piperidine-1-carboxylic acid 4-methyl-benzyl ester from Step 3 above (65 mg, 0.18 mmol) was treated with 1M BH$_3$-THF (1.80 mmol, 1.80 mL, 1M in THF) over 10 min. and was aged at r.t. 4 h. The reaction was quenched by slowly adding 2N HCl and stirring vigorously for 30 min. The reaction was basified with sat. NaHCO$_3$ and extracted with ethyl acetate (2×). The combined organics were washed with brine, dried over Na$_2$SO$_4$, filtered and concentrated in vacuo, yielding a white foam which was purified by silica gel chromatography (99:10.1 to 95:5:0.5 CH$_2$Cl$_2$:CH$_3$OH:NH$_4$OH) to give EXAMPLE 27 as a yellow oil.

$^1$H NMR (400 MHz, CD$_3$OD): δ 8.00 (d, J=2.47 Hz, 1H, Pyr-H), 7.26–7.15 (m, 6H, Pyr-H ,Ar—H), 6.88 (dd, J=7.03 Hz, 5.12 Hz, 1H, Pyr-H), 5.08 (s, 2H, CH$_2$—Ar), 4.18 (brs, 2H, CHH), 3.39 (brs, 2H, CH$_2$—N), 2.78 (brs, 2H, CHH), 2.35 (s, 3H, CH$_3$), 2.07 (s, 3H, CH$_3$), 1.90–1.60 (m, 3H, CHH, CH), 1.30–1.10 (m, 4.16 Hz, 2H, CHH)

M.S. (M+1): 354.41. .

Example 28

4-Fluorobenzyl 4-{[(3-methyl-2-pyridinyl)amino]methyl}-1-piperidinecarboxylate

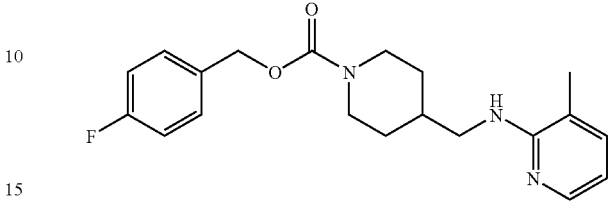

The piperidine compound (600 mg, 2.74 mmol) from EXAMPLE 27, Step 2, was treated in accordance with Steps 3 and 4 of that EXAMPLE 27, except that N-[4-(fluorobenzyloxy)-carbonyloxy]succinimide (805 mg, 3.01 mmol) was used instead of N-[4-(methylbenzyloxy)-carbonyloxy]succinimide in Step 3 to give 4-fluorobenzyl 4-{[(3-methyl-2-pyridinyl)amino]methyl}-1-piperidinecarboxylate as a clear oil.

$^1$H NMR (400 MHz, CDCl$_3$): δ 7.99 (d, J=4.29 Hz, 1H, Pyr-H), 7.34–7.31 (m, 2H, Ar—H), 7.20–7.18 (m, 1H, Pyr-H), 7.05–7.00 (m, 1H, Pyr-H), 6.50 (dd, J=7.13 Hz, 5.12 Hz, 2H, Ar—H), 5.08 (s, 2H, CH$_2$—Ar), 4.22 (brs, 3H, CHH, NH), 3.38 (brs, 2H, CH$_2$—N), 2.77 (brs, 2H, CHH), 2.06 (s, 3H, CH$_3$), 1.84–1.77 (m, 3H, CHH, CH), 1.26–1.12 (m, 2H CHH).

M.S. (M+1): 358.35.

Example 29

4-Chlorobenzyl 4-{[(3-methyl-2-pyridinyl)amino]methyl}-1-piperidinecarboxylate

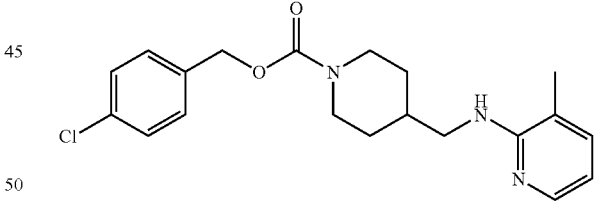

The piperidine compound (600 mg, 2.74 mmol) from EXAMPLE 27, Step 2, was treated in accordance with Steps 3 and 4, except that N-[4-(chlorobenzyloxy)carbonyloxy]succinimide (855 mg, 3.01 mmol) was used instead of N-[4-(methylbenzyloxy)-carbonyloxy]succinimide in Step 3 to give 4-chlorobenzyl 4-{[(3-methyl-2-pyridinyl)amino]methyl}-1-piperidinecarboxylate as a clear oil.

$^1$H NMR (400 MHz, CDCl$_3$): δ 7.99 (dd, J=4.90 Hz, 1.23 Hz, 1H, Pyr-H), 7.32–7.27 (m, 4H, Ar—H), 7.20–7.18 (m, 1H, Pyr-H), 6.50 (dd, J=7.18 Hz, 5.08 Hz, 1H, Pyr-H), 5.08 (s, 2H, CH$_2$—Ar), 4.20 (brs, 3H, CHH, NH), 3.38 (brs, 2H, CH$_2$—N), 2.78 (brs, 2H, CHH), 2.06 (s, 3H, CH$_3$), 1.90–1.72 (m, 3H, CHH, CH), 1.26–1.12 (m, 2H CHH).

M.S. (M+1): 374.31.

Example 30

3-Fluorobenzyl 4-[(4-pyridinylamino)methyl]-1-piperidinecarboxylate

Step 1:

N-(4-piperidinylmethyl)-4-pyridinamine

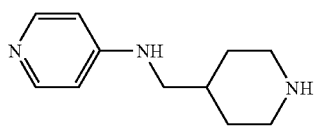

Benzyl 4-[(4-pyridinylamino)methyl]-1-piperidinecarboxylate (EXAMPLE 1) (7 g, 21 mmol) was dissolved in abs. Ethanol (150 mL) with 10% palladium on carbon (700 mg) and stirred under 1 atm of hydrogen for 2 h. The catalyst was filtered off and the filtrate was concentrated under reduced pressure to afford the N-(4-piperidinylmethyl)-4-pyridinamine as a clear oil which was used without further purification.

Step 2:

3-Fluorobenzyl 4-[(4-pyridinylamino)methyl]-1-piperidinecarboxylate

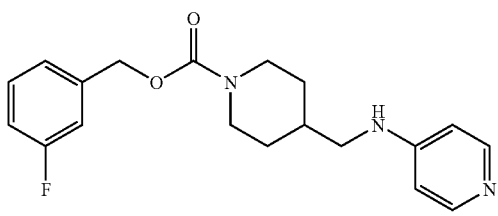

3-Fluorobenzyl alcohol (30 mg, 0.24 mmol) was treated with triphosgene (24 mg, 0.08 mmol) and N-(4-piperidinylmethyl)-4-pyridinamine (50 mg, 0.26mmol), and aged at 40° C. for 45 min. The resulting reaction solution was partitioned between 0.5M NaOH and ethyl acetate. The organics were separated, dried over $Na_2SO_4$, filtered and concentrated under reduced pressure. The resulting oil was purified by preparatory HPLC to give the TFA salt of EXAMPLE 30 as a yellow oil. M.S. (M+1): 344.36.

The following EXAMPLES 32–36 were prepared as described above in EXAMPLE 30, but replacing 3-fluorobenzyl alcohol with the appropriate alcohol:

Example 31

2-Methylbenzyl 4-[(4-pyridinylamino)methyl]-1-piperidinecarboxylate

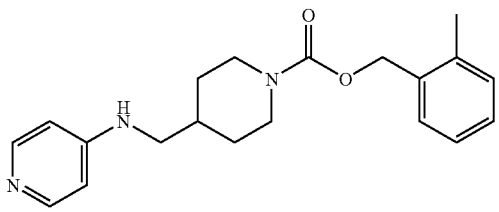

M.S. (M+1): 340.38.

Example 32

3-Methylbenzyl 4-[(4-pyridinylamino)methyl]-1-piperidinecarboxylate

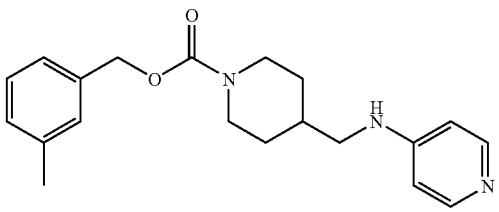

M.S. (M+1): 340.39.

Example 33

4-Methylbenzyl 4-[(4-pyridinylamino)methyl]-1-piperidinecarboxylate

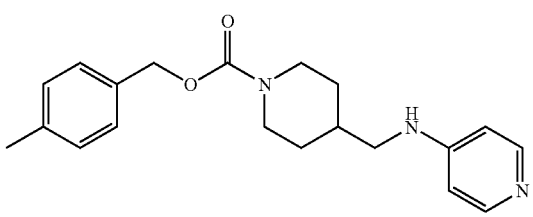

M.S. (M+1): 340.29.

Example 34

2-Methoxybenzyl 4-[(4-pyridinylamino)methyl]-1-piperidinecarboxylate

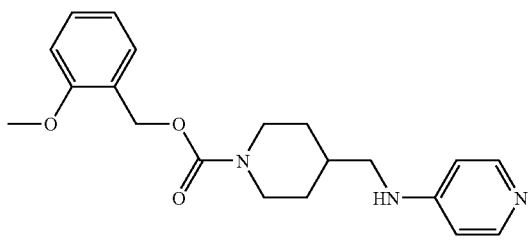

M.S. (M+1): 356.37.

Example 35

3-Methoxybenzyl 4-[(4-pyridinylamino)methyl]-1-piperidinecarboxylate

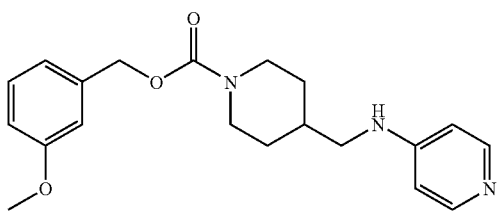

M.S. (M+1): 356.37.

Example 36

4-Methoxybenzyl 4-[(4-pyridinylamino)methyl]-1-piperidinecarboxylate

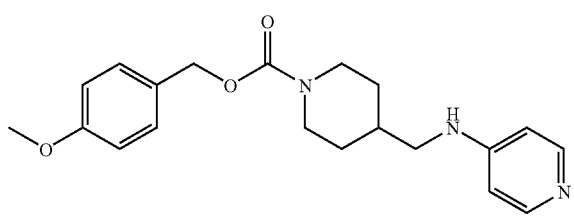

M.S. (M+1): 356.36.

Example 37

4-Fluorobenzyl 4-[(2-pyrimidinylamino)methyl]-1-piperidinecarboxylate

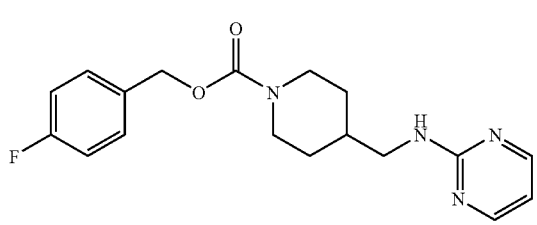

Benzyl 4-[(2-pyrimidinylamino)methyl]-1-piperidinecarboxylate (EXAMPLE 16) was hydrogenated as described in EXAMPLE 30, Step 1. Treatment with N-[4-(fluorobenzyloxy)-carbonyloxy]succinimide as described in EXAMPLE 27, Step 3, afforded the 4-fluorobenzyl 4-[(2-pyrimidinylamino)methyl]-1-piperidinecarboxylate.

$^1$H NMR (400 MHz, CDCl$_3$): δ 8.26 (d, J=4.89 Hz, 2H, Pyr-H), 7.35–7.27 (m, 2H, Ar—H), 7.05–7.01 (m, 2H, Ar—H), 6.53 (t, J=4.76 Hz, 1H, Pyr-H), 5.45 (brt, J=5.73 Hz, 1H, NH), 5.08 (s, 2H, CH$_2$—Ar), 4.20 (brd, J=27.6 Hz, 2H, CHH), 3.32 (t, J=6.22 Hz, 2H, CH$_2$—N), 2.77 (brs, 2H, CHH), 1.83–1.75 (m, 3H, CHH, CH), 1.26–1.15 (m, 2H CHH).

M.S. (M+1): 345.35.

Example 38

4-Chlorobenzyl 4-[(2-pyrimidinylamino)methyl]-1-piperidinecarboxylate

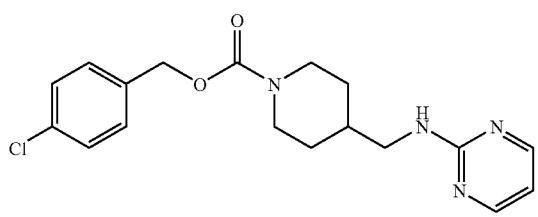

The title compound was prepared as described in EXAMPLE 37, except replacing N-[4-(fluorobenzyloxy)-carbonyloxy]succinimide with N-[4-(chlorobenzyloxy)carbonyloxy]succinimide.

$^1$H NMR (400 MHz, CDCl$_3$): δ 8.25 (d, J=4.75 Hz, 2H, Pyr-H), 7.33–7.27 (m, 4H, Ar—H), 6.51 (t, J=4.84 Hz, 1H, Pyr-H), 5.77 (bs, 1H, NH), 5.08 (s, 2H, CH$_2$—Ar), 4.18 (brs, 2H, CHH), 3.32 (brt, J=6.12 Hz, 2H, CH$_2$—N), 2.77 (brs, 2H, CHH), 1.84–1.75 (m, 3H, CHH, CH), 1.26–1.12 (m, 2H CHH).

M.S. (M+1): 361.32.

Example 39

(Cis)-3-hydroxy-4-(pyridin-4-ylaminomethyl)-piperidine-1-carboxylic acid benzyl ester Step 1:

1-Benzyl-4-hydroxymethyl-piperidin-3-ol

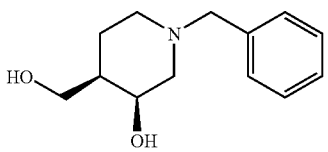

Sodium borohydride (40 g) was added in portions to a stirred solution of ethyl N-benzyl-3-oxopiperidine-4-carboxylate hydrochloride (23.6 g, 90 mmol) in methanol (500 mL), over 2 h. Water (300 mL) was added slowly, the mixture stirred for 15 min and then the organics were evaporated. The residue was partitioned between DCM and water (×3), the combined organic layers dried over anhydrous sodium sulfate, and the solvent evaporated to give 1-benzyl-4-hydroxymethyl-piperidin-3-ol product as a cis/trans mixture, which was used in the next step without further purification. M.S (M+1): 222.

Step 2:

3-Hydroxy-4-hydroxymethyl-piperidine-1-carboxylic acid benzyl ester

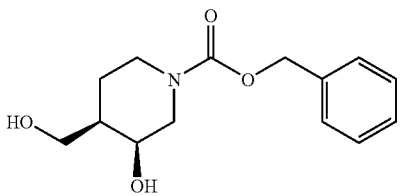

A solution of the 1-benzyl-4-hydroxymethyl-piperidin-3-ol from Step 1 above (13.5 g) in methanol (450 mL) was hydrogenated at 50 psi over 20% palladium hydroxide on charcoal (10 g) for 48 h in three batches. The combined reaction mixtures were filtered and the filtrate evaporated to give an oil. This was dissolved in water (100 mL) and dioxane (100 mL), cooled to 5° C., and benzyl chloroformate (7.8 mL) was added slowly, with addition of 1M NaOH to maintain a pH of 10–11. After 30 min, the cooling bath was removed and reaction mixture stirred for 30 min. The reaction mixture was concentrated to remove dioxane and the residue extracted with EtOAc (×3). The combined extracts were washed with brine, dried over anhydrous sodium sulfate and solvent evaporated to give a mixture of cis and trans 3-hydroxy-4-hydroxymethyl-piperidine-1-carboxylic acid benzyl ester products. Purification by flash column chromatography (80% EtOAc hexane to 5% MeOH EtOAc) gave the upper Rf cis isomer (major) and the lower Rf trans isomer (minor)

M.S (M+1): 266. .

Step 3:

(Cis)-3-hydroxy-4-(toluene-4-sulfonyloxymethyl)-piperidine-1-carboxylic acid benzyl ester

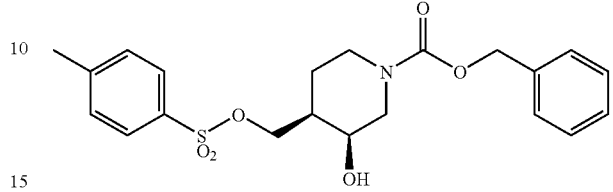

A solution of the (cis)-3-hydroxy-4-hydroxymethyl-piperidine-1-carboxylic acid benzyl ester from Step 2 above (7.65 g) in chloroform (200 mL) was treated with pyridine (2.6 mL) and 4-toluenesulfonyl chloride (6.05 g) and the reaction mixture heated to 60° C. for 18 h. Additional pyridine (0.85 mL) and 4-toluenesulfonyl chloride (2.0 g) were added to the cooled reaction and heating continued for a further 24 h. The resulting reaction mixture was cooled to room temperature and washed with 10% aqueous citric acid solution and water, dried over anhydrous sodium sulfate and the solvent evaporated to give, after flash column chromatography, the (cis)-3hydroxy-4-(toluene-4-sulfonyloxymethyl)-piperidine-1-carboxylic acid benzyl ester.

Step 4:

(Cis)-4-aminomethyl-3-hydroxy-piperidine-1-carboxylic acid benzyl ester

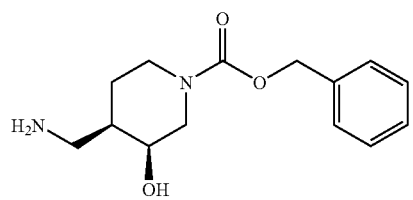

A solution of the tosylate compound (6.80 g) from Step 3 above was dissolved in DMF (50 mL) and treated with sodium azide (3.16 g). The reaction mixture was then heated to 50° C. for 48 h, cooled to room temperature and partitioned between dilute aqueous sodium bicarbonate and EtOAc. The organic layer was washed with brine, dried over anhydrous sodium sulfate and solvent evaporated to give the azide (5.23 g) which was dissolved in THF (50 mL) and treated with triphenylphosphine (14.07 g) and water (3.25 mL). The reaction mixture was stirred for 18 h at room temperature, the volatiles evaporated and the residue purified by flash column chromatography (DCM to 80/20/2 DCM MeOH NH4OH) to give (cis)-4-aminomethyl-3-hydroxy-piperidine-1-carboxylic acid benzyl ester as an oil.

M.S (M+1): 265. Step 5:

(Cis)-3-hydroxy-4-(pyridin-4-ylaminomethyl)-piperidine-1-carboxylic acid benzyl ester

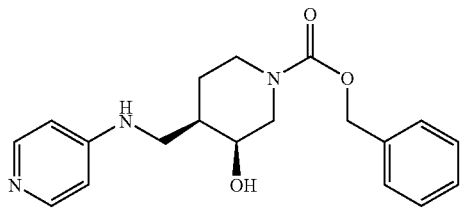

A mixture of the cis 4-aminomethyl-3-hydroxy-piperidine-1-carboxylic acid benzyl ester (245 mg) from Step 4 above, 4-chloropyridine (105 mg) and isopropanol (0.4 mL) was heated to 120° C. in a sealed vial for 24 h, cooled to room temperature and the solvents evaporated. The resulting crude mixture was purified by flash column chromatography (DCM to 80/20/2 DCM MeOH NH4OH) to give impure cis 3-hydroxy-4-(pyridin-4-ylaminomethyl)-piperidine-1-carboxylic acid benzyl ester. This was purified by preparative reverse phase HPLC (95% H₂O 5% MeCN to 100% MeCN both containing 0.1% TFA). Evaporation gave an oil which was partitioned between DCM and aqueous sodium bicarbonate solution. The organic layer was dried over anhydrous sodium sulfate and solvent evaporated to give a white solid. M.S (M+1): 342.

Example 40

(−)-(Cis)-3-hydroxy-4-(pyridin-4-ylaminomethyl)-piperidine-1-carboxylic acid benzyl ester and (+)-(cis)-3-hydroxy-4-(pyridin-4-ylaminomethyl)-piperidine-1-carboxylic acid benzyl ester The enantiomers of (cis)-3-hydroxy-4-(pyridin-4-ylaminomethyl)-piperidine-1-carboxylic acid benzyl ester were separated by preparative HPLC on a Chiralpak® AD column, eluting with 70% (0.1% diethylamine in hexane) 30% isopropanol to give the earlier eluting (−) enantiomer followed by the (+)-enantiomer.

Example 41

(cis)-3-hydroxy-4-(pyridin-4-ylaminomethyl)-piperidine-1-carboxylic acid 4-methyl-benzyl ester Step 1:

3-Hydroxy-4-[(2,3,5,6-tetrachloro-pyridin-4-ylamino)-methyl]-piperidine-1-carboxylic acid benzyl ester

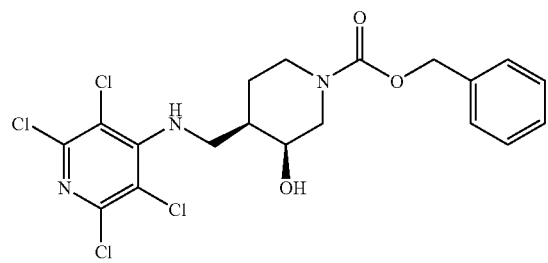

2,3,5,6-tetrachloro-4-nitropyridine (S. M. Roberts et al., J. Chem. Soc. C, 2844–2848(1968)) (1.7 g, 6.5mmol) was added to a solution of (cis)-4-aminomethyl-3-hydroxy-piperidine-1-carboxylic acid benzyl ester (1.71 g, 6.49 mmol) and N-methylmorpholine (0.785 mL, 7.15 mmol) in THF (50 mL) at room temperature. The resulting reaction mixture was stirred for 18 h at room temperature then partitioned between EtOAc and water, The organic layer was washed with saturated sodium bicarbonate solution, dried over anhydrous sodium sulfate and the solvent evaporated to give crude product purified by flash column chromatography (20–80% EtOAc hexane) to give 3-hydroxy-4-[(2,3,5,6-tetrachloro-pyridin-4-ylamino)-methyl]-piperidine-1-carboxylic acid benzyl ester compound. M.S (M+1): 478.

Step 2:

4-(Pyridin-4-ylaminomethyl)-piperidin-3-ol

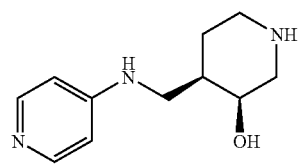

A suspension of 3-hydroxy-4-[(2,3,5,6-tetrachloro-pyridin-4-ylamino)-methyl]-piperidine-1-carboxylic acid benzyl ester compound from Step 1 above (1.64 g) and potassium carbonate (6 g) in ethanol (200 mL) was hydrogenated at 60 psi over 1 g of 10% palladium on charcoal for 5 h. The reaction mixture was filtered and the solids washed well with ethanol. The filtrate was evaporated, taken up in 40% MeOH DCM and refiltered. The filtrate was evaporated to give crude 4-(pyridin-4-ylaminomethyl)-piperidin-3-ol product used without further purification in the next step.

Step 3:

(Cis)-3-hydroxy-4-(pyridin-4-ylaminomethyl)-piperidine-1-carboxylic acid 4-methyl-benzyl ester

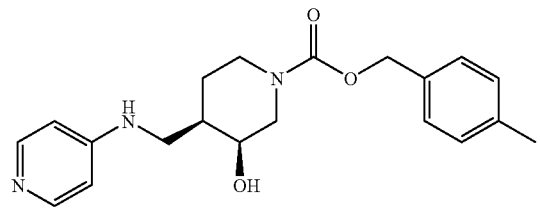

A suspension of the 4-(pyridin-4-ylaminomethyl)-piperidin-3-ol from Step 2 above (0.076 g, 0.367 mmol) in DMF (1.5 mL) was treated with carbonic acid 2,5-dioxo-pyrrolidin-1-yl ester 4-methyl-benzyl ester (0.097 g, 0.37 mmol) (INTERMEDIATE 1A) and the resulting reaction mixture stirred at rt for 5 min. The mixture was then partitioned between dilute sodium carbonate solution and EtOAc. The organic layer was washed with saturated sodium bicarbonate solution and brine, dried over anhydrous sodium sulfate, and the solvent evaporated to give a crude product. Purification by flash column chromatography (DCM to 80/20/2 DCM MeOH NH4OH) afforded the cis 3-hydroxy-4-(pyridin-4-ylaminomethyl)-piperidine-1-carboxylic acid 4-methyl-benzyl ester compound. M.S (M+1): 356.

Example 42

(Cis)-3-hydroxy-4-(pyridin-4-ylaminomethyl)-piperidine-1-carboxylic acid 4-ethyl-benzyl ester

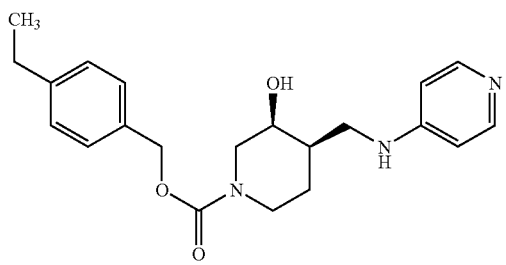

The title compound was prepared as described in EXAMPLE 41, Step 3, but replacing carbonic acid 2,5-dioxo-pyrrolidin-1-yl ester 4-methyl-benzyl ester with carbonic acid 2,5-dioxo-pyrrolidin-1-yl ester 4-ethyl-benzyl ester (INTERMEDIATE 1D). M.S (M+1): 370

Example 43

(Cis)-3-hydroxy-4-(pyridin-2-ylaminomethyl)-piperidine-1-carboxylic acid benzyl ester

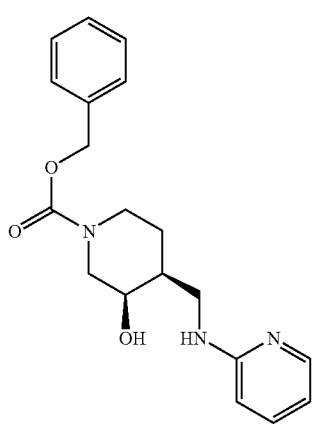

A mixture of (cis)-4-aminomethyl-3-hydroxy-piperidine-1-carboxylic acid benzyl ester (0.1 g, 378 mmol) and 2-fluoropyridine (0.25 mL) was heated to 120° C. for 24 h. The reaction mixture was partitioned between EtOAc and water. The organic layer was washed with brine, dried over anhydrous sodium sulfate, and the solvent evaporated to give a (cis)-3-hydroxy-4-(pyridin-2-ylaminomethyl)-piperidine-1-carboxylic acid benzyl ester crude product, which was purified by flash column chromatography (50% EtOAc hexane to 5% MeOH EtOAc). M.S (M+1): 342

Example 44

4-[(3-Cyano-pyridin-2-ylamino)-methyl]-piperidine-1-carboxylic acid benzyl ester

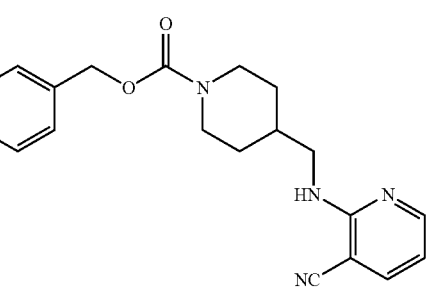

A mixture of benzyl 4-(aminomethyl)piperidine-1-carboxylate (EXAMPLE 13, Step 1) (1 g, 4.03 mmol) and 3-cyanopyridine (0.25 g) was heated to 100° C. for 30 min. The reaction mixture was partitioned between EtOAc and pH5.2 citrate buffer. The organic layer was washed with brine, dried over anhydrous sodium sulfate, and the solvent evaporated to give a solid which was stirred with 5 mL ether and 0.5 mL EtOAc for 1 h and filtered to give the title compound as a solid. M.S (M+1): 351

Example 45

4-[(3-Chloro-pyridin-2-ylamino)-methyl]-piperidine-1-carboxylic acid benzyl ester

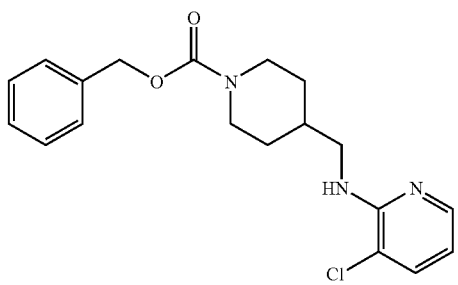

A mixture of benzyl 4-(aminomethyl)piperidine-1-carboxylate (EXAMPLE 13, Step 1) (1 g, 4.03 mmol) and 2,3-dichloropyridine (0.25 g) was heated to 100° C. for 12 h. The reaction mixture was cooled and partitioned between EtOAc and pH5.2 citrate buffer. The organic layer was washed with brine, dried over anhydrous sodium sulfate and the solvent evaporated to give a crude product. Purification by flash column chromatography (5–50% EtOAc hexane) afforded the title compound. M.S (M+1): 360.

Example 46

4-[(3-Trifluoromethyl-pyridin-2-ylamino)-methyl]-piperidine-1-carboxylic acid benzyl ester

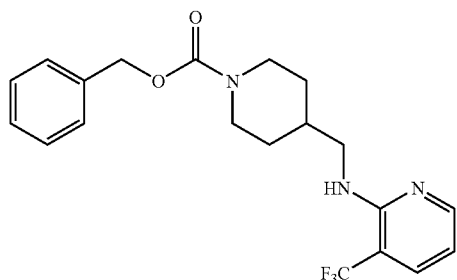

A mixture of benzyl 4-(aminomethyl)piperidine-1-carboxylate (EXAMPLE 13, Step 1) (1 g, 4.03 mmol) and 2-chloro-3-trifluoromethylpyridine (0.25 g) was heated to 100° C. for 12 h. The reaction mixture was cooled and partitioned between EtOAc and pH5.2 citrate buffer. The organic layer was washed with brine, dried over anhydrous sodium sulfate, and the solvent evaporated to give a crude product. Purification by flash column chromatography (5–50% EtOAc hexane) afforded the title compound. M.S (M+1): 394.

Example 47

4-[(3-Chloro-pyrazin-2-ylamino)-methyl]-piperidine-1-carboxylic acid benzyl ester

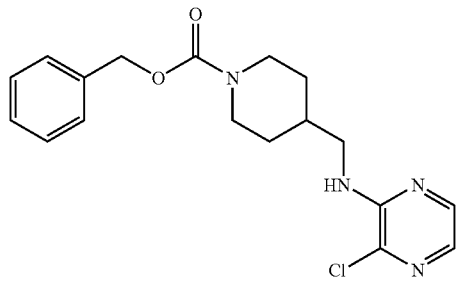

A mixture of benzyl 4-(aminomethyl)piperidine-1-carboxylate (EXAMPLE 13, Step 1) (1.25 g, 5.04 mmol) and 2,3-dichloropyrazine (0.25 g) was heated to 100° C. for 1 h. The reaction mixture was cooled and partitioned between EtOAc and pH5.2 citrate buffer. The organic layer was washed with brine, dried over anhydrous sodium sulfate, and the solvent evaporated to give a crude product. Purification by flash column chromatography (5–50% EtOAc hexane) afforded the title compound. M.S (M+1): 361.

Example 48

4-[(3-Hydroxy-pyrazin-2-ylamino)-methyl]-piperidine-1-carboxylic acid benzyl ester Step 1:

3-[(Piperidin-4-ylmethyl)-amino]-pyrazin-2-ol

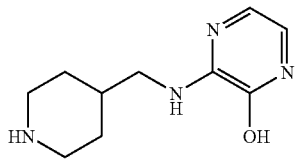

4-[(3-Chloro-pyrazin-2-ylamino)-methyl]-piperidine-1-carboxylic acid benzyl ester (EXAMPLE 47) (2.21 g, 6.12 mmol) and 3M HCl (200 mL) was heated to reflux for 18 h, cooled to rt and the volatiles evaporated. The residue was azeotroped with ethanol (3×100 mL) and then stirred with 50 mL ether for 1 h, filtered and the solid dried to yield a cream solid.

Step 2:

4-[(3-Hydroxy-pyrazin-2-ylamino)-methyl]-piperidine-1-carboxylic acid benzyl ester

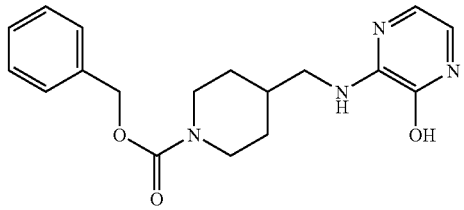

To a solution of 3-[(piperidin-4-ylmethyl)-amino]-pyrazin-2-ol from Step 1 above (0.287 g, 1.021 mmol) in DMF (5 mL) was added triethylamine (0.356 mL, 2.55 mmol), followed by N-(benzyloxycarbonyloxy)succinimide (0.305 g, 1.23 mmol). The resulting reaction mixture was stirred at rt for 15 min, then partitioned between EtOAc and water. The organic layer was washed with water and brine, dried over anhydrous sodium sulfate and the crude product purified by flash column chromatography (50% EtOAc hexane to 5% MeOH EtOAc) to give an oil which solidified on standing. M.S (M+1): 343.24.

Example 49

4-[(5-Chloro-pyrimidin-4-ylamino)-methyl]-piperidine-1-carboxylic acid benzyl ester Step 1:

4-[(2,5,6-Trichloro-pyrimidin-4-ylamino)-methyl]-piperidine-1-carboxylic acid benzyl ester

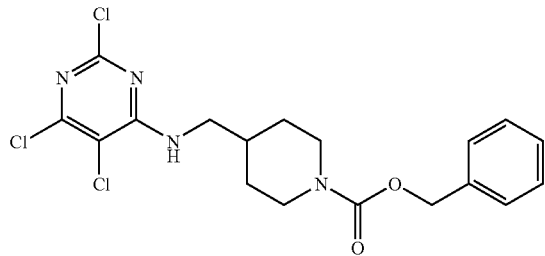

To a solution of benzyl 4-(aminomethyl)piperidine-1-carboxylate (EXAMPLE 13, Step 1) and N,N-diisopropylethylamine (2.6 g, 20 mmol) in THF (40 mL) at −78° C. was added a solution of tetrachloropyrimidine (4.4 g, 20 mmol). The cooling bath was removed and the solution was stirred for 45 min. The solution was concentrated and purified by filtering through a pad of silica gel using ether.

Step 2:

4-[(5-Chloro-2,6-bis-methylsulfanyl-pyrimidin-4-ylamino)-methyl]-piperidine-1-carboxylic acid benzyl ester

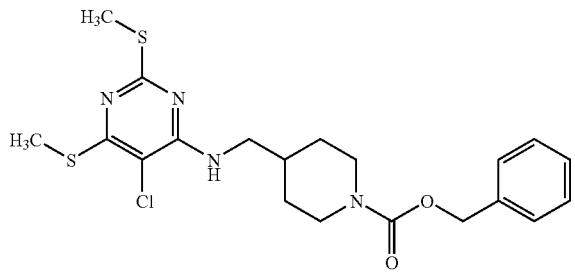

To 4-[(2,5,6-trichloro-pyrimidin-4-ylamino)-methyl]-piperidine-1-carboxylic acid benzyl ester (1 g, 2.33 mmol) in DMF was added sodium thiomethoxide (0.4 g, 5.8 mmol). The, resulting reaction mixture was stirred for 2 h and quenched with aqueous ammonium chloride. The product was extracted with ethyl acetate, dried (Na₂SO₄), concentrated, and purified by silica gel chromatography (ether/hexanes).

Step 3:

4-[(5-Chloro-pyrimidin-4-ylamino)-methyl]-piperidine-1-carboxylic acid benzyl ester

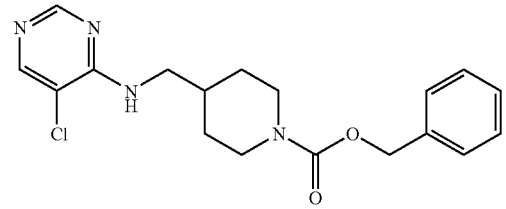

4-[(5-Chloro-2,6-bis-methylsulfanyl-pyrimidin-4-ylamino)-methyl]-piperidine-1-carboxylic acid benzyl ester (1.0 g, 2.2 mmol) was suspended in ethanol (15 mL) and ethyl acetate added to give a homogeneoussolhution, and excess Raney nickel was added. The resulting reaction mixture was stirred overnight. More Raney Nickel was added and the reaction mixture was heated to 80° C. for 3 h. The mixture was filtered and the solids were washed with hot ethanol/ethyl acetate several times. The organics were concentrated and the resulting residue was purified by silica gel chromatography (isopropanol/methylene chloride). The product was dissolved in ether and treated with ethereal HCl (2.2 mmol) to form the HCl salt which was collected by filtration. The resulting 4-[(5-chloro-pyrimidin-4-ylamino)-methyl]-piperidine-1-carboxylic acid benzyl ester hydrochloride salt was collected by filtration as a colorless solid.

$^1$H NMR (400 MHz, CD₃OD): δ 8.67 (s, 1 h, pyrimidine), 8.45 (s, 1 h, pyrimidine), 7.32 (m, 5 h, Ar), 5.10 (s, 2 h, CHH), 4.15 (d, J=13.0 Hz, 2 h, CHH), 3.58 (d, J=7.2 Hz, 2 h, CHH), 2.83 (m, 2 h, CHH), 1.97 (m, 1 h, CH), 1.74 (d, J=12.0 Hz, 2 h, CHH).

M.S (M+1): 361.3

Example 50

4-[(2-Hydroxymethyl-pyridin-4-ylamino)-methyl]-piperidine-1-carboxylic acid benzyl ester Step 1:

Benzyl 4-(aminomethyl)piperidine-1-carboxylate

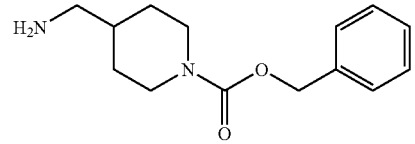

4-Aminomethylpiperidine (40 g, 350 mmol) and benzaldehyde (37.3 mL, 368 mmol) in toluene (600 mL) were heated to reflux under dean stark conditions for 2 h. The reaction mixture was cooled to room temperature and 500 mL dichloromethane added. The solution was cooled to 5° C. and treated with N-(benzyloxycarbonyloxy)succinimide (91.7 g, 368 mmol). After 10 min., the cooling bath was removed and the reaction mixture stirred for 1 h. The solvents were evaporated and the residue stirred with 400 mL THF and 400 mL 2M HCl for 1 h. The mixture was concentrated to remove organics and extracted with ether (3×300 mL). The aqueous phase was adjusted to pH 14 with 50% NaOH and extracted with ethyl acetate. The organic layer was washed with water and brine, dried over anhydrous sodium sulfate, and the solvent evaporated to give benzyl 4-(aminomethyl)piperidine-1-carboxylate compound.

Step 2:

4-[(1-Benzyloxycarbonyl-piperidin-4-ylmethyl)-amino]-pyridine-2-carboxylic acid

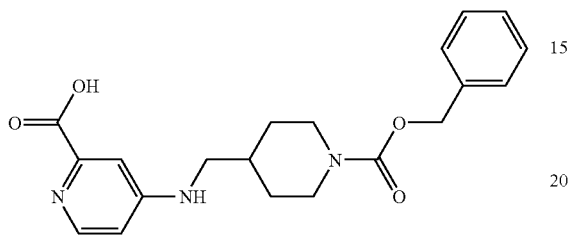

To a solution of 4-chloropicolinic acid (0.8 gm, 0.0051 mol) in DMSO (4 mL) was added benzyl 4-(aminomethyl) piperidine-1-carboxylate (2.5 gm, 0.010 mol) and the mixture warmed to 140° C. for 18 h. The reaction was cooled and diluted with 10% sodium bicarbonate (100 mL) and washed with ether (2×25 mL). The aqueous extract was washed with dichloromethane (3×50 mL), and the dichloromethane extract dried over sodium sulfate and concentrated to an oil (2.4 gm). The oil was chromatographed on silica using dichloromethane/methanol/acetic acid/water-90/10/1/1 to give 4-[(1-benzyloxycarbonyl-piperidin-4-ylmethyl)-amino]-pyridine-2-carboxylic acid.

$^1$H NMR 400 MHz (δ, DMSO) δ: 8.98 (s, 1H); 8.2–8.0 (m, 1H); 7.6–7.2 (m, 5H); 7.01 (brs, 1H); 5.08 (s, 2H); 4.02 (brd, 2H); 2.80 (brs, 2H); 1.8–1.6 (m, 3H); 1.3–1.1 (m, 2H).
M.S. (M+1): 370.

Step 3:

4-[(2-Hydroxymethyl-pyridin-4-ylamino)-methyl]-piperidine-1-carboxylic acid benzyl ester

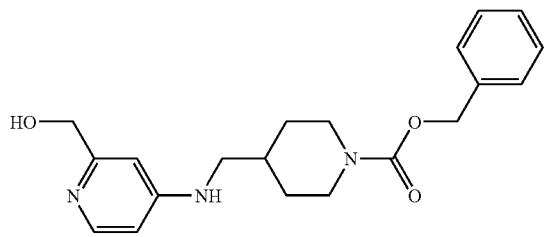

To a 0° C. solution of 4-[(1-benzyloxycarbonyl-piperidin-4-ylmethyl)-amino]-pyridine-2-carboxylic acid (0.59 gm, 0.0016 mol) in THF (2 mL) under nitrogen was added a solution of 1.0M borane-tetrahydrofuran (6 mL) and the mixture allowed to stir at room temperature for 1 h. The reaction was cooled to 0° C., quenched with 1N HCl (10 mL), concentrated and diluted with 10% aqueous sodium bicarbonate. Extraction with dichloromethane (2×50 mL) and concentration of the organic layer gave 540 mg of crude material. Column chromatography using dichloromethane/methanol/ammonium hydroxide-90/10/2 and crystallization from diethyl ether gave 4-[(2-hydroxymethyl-pyridin-4-ylamino)-methyl]-piperidine-1-carboxylic acid benzyl ester.

$^1$H NMR (400 MHz CDCL3) δ: 8.13 (d, 1H, J=6.8 Hz), 7.5–7.1 (m, 5H); 6.35 (m, 2H); 5.12 (s, 2H); 4.61 (s, 2H); 4.20 (brm, 3H); 3.08 (m, 2H); 2.78 (m, 2H) 1.8–1.6 (m, 3H); 1.3–1.1 (m, 2H).
M.S.(M+1): 356.

Example 51

4-[(2-Dimethylaminomethyl-pyridin-4-ylamino)-methyl]-piperidine-1-carboxylic acid benzyl ester Step 1:

4-[(2-Dimethylcarbamoyl-pyridin-4-ylamino)-methyl]-piperidine-1-carboxylic acid benzyl ester

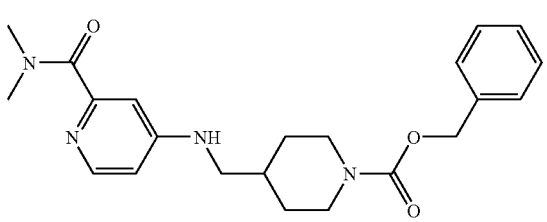

To a mixture of 4-[(1-benzyloxycarbonyl-piperidin-4-ylmethyl)-amino]-pyridine-2-carboxylic acid (EXAMPLE 50, Step 2) (50 mg, 0.000135 mol), 1-hydroxybenzotriazole hydrate (31 mg, 0.0002 mol), 2.0M dimethylamine/THF (0.100 mL, 0.0002 mol) and triethylamine (0.048 mL, 0.0002 mol) in DMF (2 mL) was added 1-ethyl-3-(3-dimethylaminopropyl)carbodiimide hydrochloride (39 mg, 0.0002 mol) and the mixture allowed to stir at room temperature for 7 days. The mixture was quenched into water (10 mL) and extracted with ethyl acetate (20 mL). The ethyl acetate extract was washed with 10% aqueous sodium bicarbonate (10 mL), brine (5 mL), dried over sodium sulfate and filtered. The filtrate was concentrated in vacuo and the residue chromatographed (reverse phase C-18 using acetonitrile/0.1% trifluoroacetic acid in water) to give 4-[(2-dimethylcarbamoyl-pyridin-4-ylamino)-methyl]-piperidine-1-carboxylic acid benzyl ester as its trifluoroacetate salt.
M.S. (M+1): 397.

Step 2:

4-[(2-dimethylaminomethyl-pyridin-4-ylamino)-methyl]-piperidine-1-carboxylic acid benzyl ester

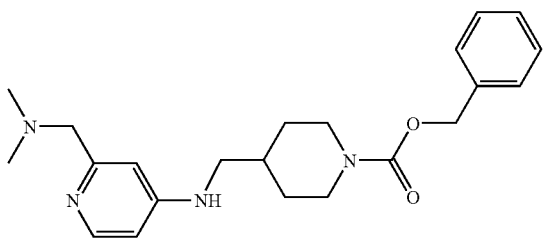

To 4-[(2-Dimethylcarbamoyl-pyridin-4-ylamino)-methyl]-piperidine-1-carboxylic acid benzyl ester (28 mg, 0.05 mmol) was added a solution of 1.0M borane-tetrahydrofuran (2 mL). The reaction was stirred at room temperature for 24 h. The reaction was quenched with 1N HCl (2 mL) and concentrated in vacuo to an oil. Reverse phase chromatography (C-18 using acetonitrile/0.1% trifluoroacetic acid in water) gave upon concentration in vacuo EXAMPLE 51.

$^1$H NMR (400 MHz CD$_3$OD) δ: 8.10 (m, 1H); 7.4–7.2 (m, 5H); 7.2–6.8 (m, 2H); 5.12 (s, 2H); 4.41 (s, 2H); 4.18 (m, 2H; 3.30 (m, 2H); 2.78 (m, 2H) 1.8–1.6 (m, 3H); 1.3–1.1 (m, 2H).

M.S. (M+1): 383.

Example 52

4-[(2-Methylaminomethyl-pyridin-4-ylamino)-methyl]-piperidine-1-carboxylic acid benzyl ester

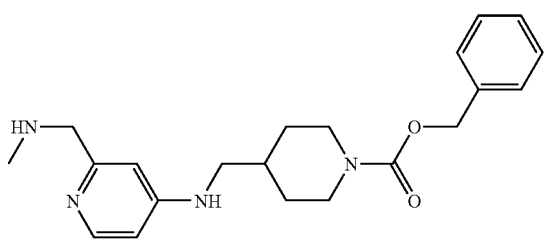

The title compound was prepared in a similar manner to EXAMPLE 51, except replacing dimethylamine with methylamine in Step 1. M.S. (M+1): 369.

Example 53

4-[(3-Chloro-pyrazin-2-ylamino)-methyl]-piperidine-1-carboxylic acid 4-fluoro-benzyl ester

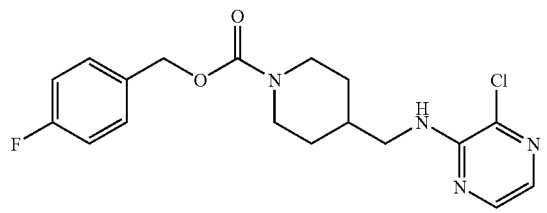

To 2,3-dichloropyrazine (0.160 gm, 0.00107 mol) was added 4-fluorobenzyl 4-(aminomethyl)piperidine-1-carboxylate (INTERMEDIATE 2C) (0.86 gm, 0.00322 mol) and the resulting mixture heated under nitrogen at 110° C. for 30 min. The reaction was cooled, diluted with ethyl acetate (50 mL), and washed with 10% aqueous sodium/citric acid pH=5.2 (3×30 mL), and 10% aqueous sodium bicarbonate (30 mL). The ethyl acetate extract was dried over sodium sulfate, filtered through a pad of silica and concentrated to an oil. Crystallization from ether/hexane gave 4-[(3-chloro-pyrazin-2-ylamino)-methyl]-piperidine-1-carboxylic acid 4-fluoro-benzyl ester.

$^1$H NMR (400 MHz DMSO d$_6$) δ: 7.99 (d, 1H, J=2.7 Hz); 7.52 (d, 1H, J=2.7 Hz); 7.41 (d, 1H, J=5.7 Hz); 7.39 (d, 1H, J=5.7 Hz); 7.19 (m, 2H); 7.16 (m, 1H); 5.03 (s, 2H); 3.97 (m, 2H); 3.25 (m, 2H); 2.75 (m, 2H); 1.9 (m, 1H); 1.7 (m, 2H); 1.1–0.9 (m, 2H).

M.S. (M+1): 379.

Example 54

4-Hydroxy-4-(pyridin-4-ylaminomethyl)-piperidine-1-carboxylic acid benzyl ester*TFA salt Step 1:

4-Aminomethyl-1-benzyl-piperidin-4-ol

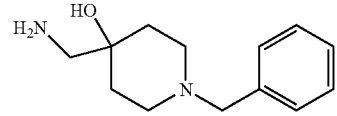

A mixture of 1-benzyl-4-hydroxy-piperidine-4-carbonitrile (5.00 g, 19.78 mmol) and BH$_3$.THF (59.35 mmol, 59.35 mL, 1M in THF) was heated at 80° C. for 1 h. Cooled to 0° C. and quenched with conc. HCl (20 mL), the reaction solution was then stirred at rt in 1 h. The reaction solution was basified with 10N NaOH to pH 8, and extracted with ethyl acetate (3×100 mL). The combined extracts were washed with water (50 mL), brine (30 mL), dried over Na$_2$SO$_4$, filtered and concentrated in vacuo to give 4-aminomethyl-1-benzyl-piperidin-4-ol.

M.S. (M+1): 221.31

Step 2:

4-BOC-aminomethyl-1-benzyl-piperidin-4-ol

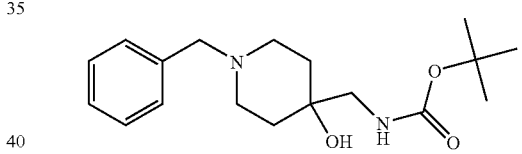

To a cooled (0° C.), stirred solution of 4-aminomethyl-1-benzyl-piperidin-4-ol (4.00 g, 18.16 mmol) in dry CH$_2$Cl$_2$ (40 mL), under N$_2$ was slowly added BOC$_2$O (4.36 g, 19.97 mmol) dissolved in dry CH$_2$Cl$_2$ (5 mL). The ice bath was removed and the reaction solution allowed to warm to rt over 1 h, then concentrated in vacuo. The residue was purified by silica gel chromatography, 1–10 (10% NH$_4$OH in MeOH)/99–90 CH$_2$Cl$_2$) to give 4-BOC-aminomethyl-1-benzyl-piperidin-4-ol.

M.S. (M+1): 321.41

Step 3:

4-BOC-aminomethyl-piperidin-4-ol

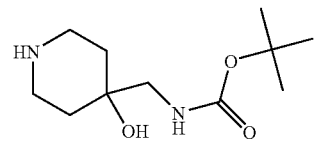

A mixture of 4-BOC-aminomethyl-1-benzyl-piperidin-4-ol (0.50 g, 1.56 mmol), Pd(OH)$_2$ (20% on carbon, 0.05 g) in absolute ethanol (15 mL) was shaken under 60 psi H₂ atmosphere for 3 h. Filtered and concentrated, the reaction gave 4-BOC-aminomethyl-piperidin-4-ol. M.S. (M+1): 231.28

Step 4:

4-BOC-aminomethyl-1-CBZ-piperidin-4-ol

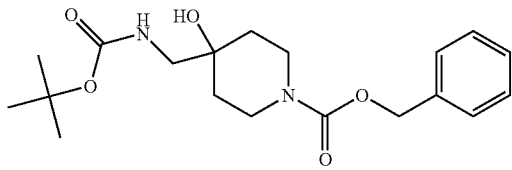

To a cooled (0° C.), stirred solution of 4-BOC-aminomethyl-piperidin-4-ol (0.35 g, 1.52 mmol) in dried CH₂Cl₂ (5 mL), under N₂ was slowly added CBZ-Cl (0.24 mL, 1.67 mmol), followed by triethylamine (0.42 mL, 3.04 mmol). The ice bath was removed and the reaction solution was stirred to rt in 1 h, then concentrated in vacuo. The residue was purified by silica gel chromatography (10 CH₂Cl₂: 1–20 IPA: 89–10 hexane)) to give 4-BOC-aminomethyl-1-CBZ-piperidin-4-ol.

M.S. (M+1): 365.39

Step 5:

4-aminomethyl-1-CBZ-piperidin-4-ol

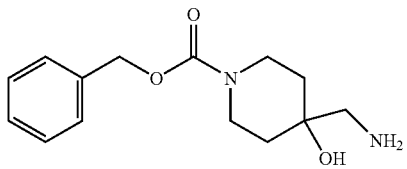

To a stirred solution of 4-BOC-aminomethyl-1-CBZ-piperidin-4-ol (0.50 g, 1.37 mmol) in dried CH₂Cl₂ (3 mL) was slowly added trifluoroacetic acid (3 mL). The resulting reaction solution was stirred at rt for 20 min., then concentrated in vacuo. The residue was dissolved in ethyl acetate (100 mL), washed with sat. aq. NaHCO₃ (20 mL), water (20 mL), brine (10 mL), dried over Na₂SO₄, filtered and concentrated to give 4-aminomethyl-1-CBZ-piperidin-4-ol. M.S. (M+1): 265.32

Step 6:

4-Hydroxy-4-(pyridin-4-ylaminomethyl)-piperidine-1-carboxylic acid benzyl ester*TFA salt

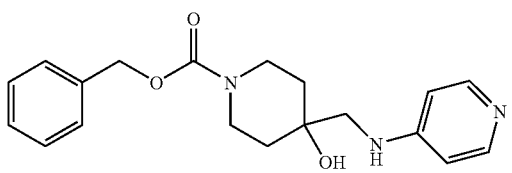

A solution of 4-aminomethyl-1-CBZ-piperidin-4-ol (0.10 g, 0.38 mmol), 4-bromo-pyridine (0.06 g, 0.38 mmol) in IPA (2 mL) was heated at 100° C. in a sealed reaction tube for 7 h. Cooled to rt, the reaction mixture was diluted with ethyl acetate (100 mL), washed with sat. aq. NaHCO₃ (20 mL), water (20 mL), brine (10 mL), dried over Na₂SO₄, filtered and concentrated. The residue was purified by reverse phase chromatography to give 4-hydroxy-4-(pyridin-4-ylaminomethyl)-piperidine-1-carboxylic acid benzyl ester as a TFA salt. M.S. (M+1): 342.35

Example 55

4-[(3-Bromo-pyridin-4-ylamino)-methyl]-piperidine-1-carboxylic acid benzyl ester

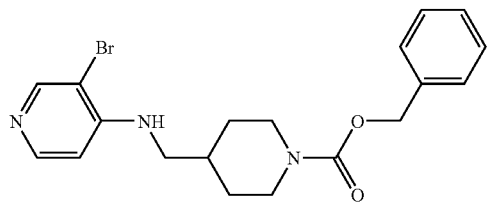

A mixture of benzyl-4-(aminomethyl)piperidine-1-carboxylate (EXAMPLE 13, Step 1, 0.20 g, 0.81 mmol), 3,4-dibromo-pyridine (*Chem. Abstracts*, 58:5627) (0.19 g, 0.81 mmol) in IPA (0.5 mL) was heated at 100° C. in a sealed reaction tube for 7 h, then concentrated in vacuo. The residue was purified by silica gel chromatography (DCM IPA hexane)) to give 4-[(3-Bromo-pyridin-4-ylamino)-methyl]-piperidine-1-carboxylic acid benzyl ester. M.S. (M+1): 405.27

Example 56

4-[(3-Fluoro-pyridin-4-ylamino)-methyl]-piperidine-1-carboxylic acid benzyl ester TFA salt

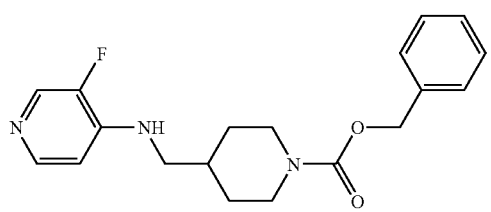

A mixture of benzyl-4-(aminomethyl)piperidine-1-carboxylate (EXAMPLE 13, Step 1, 0.20 g, 0.81 mmol), 3-fluoro-4-iodo-pyridine (*Tetrahedron*, 49:49–64(1993) (0.18 g, 0.81mmol) in IPA (0.1 mL) was heated at 100° C. in a sealed reaction tube for 100 h, then concentrated in vacuo. The residue was purified by reversed phase chromatography to give 4-[(3-fluoro-pyridin-4-ylamino)-methyl]-piperidine-1-carboxylic acid benzyl ester as a TFA salt. M.S. (M+1): 344.36

Example 57

4-[(2-Chloro-6-methyl-pyrimidin-4-ylamino)-methyl]-piperidine-1-carboxylic acid benzyl ester

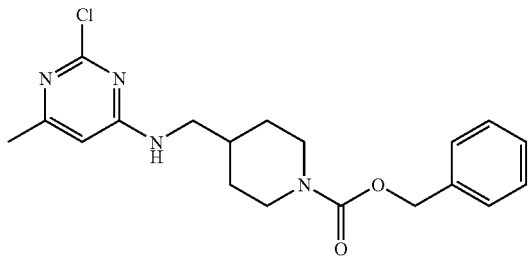

To a stirred solution of 2,4-dichloro-6-methyl-pyrimidine (3.61 g, 22.15 mmol), triethylamine (7.02 mL, 50.34 mmol) in DMF (15 mL) was slowly added benzyl-4-(aminomethyl) piperidine-1-carboxylate (EXAMPLE 13, Step 1, 5.00 g, 20.13 mmol). The resulting reaction solution was stirred at rt for 2 h, then diluted with ethyl acetate (400 mL), washed with water (3×30 mL), brine (30 mL), dried over Na$_2$SO$_4$, filtered and concentrated. The residue was purified by silica gel chromatography (20–80% ethyl acetate in hexane) to give 4-[(2-chloro-6-methyl-pyrimidin-4-ylamino)-methyl]-piperidine-1-carboxylic acid benzyl ester. M.S. (M+1): 375.36

Example 58

4-[(6-Methyl-pyrimidin-4-ylamino)-methyl]-piperidine-1-carboxylic acid benzyl ester Step 1:

4-[(6-Methyl-pyrimidin-4-ylamino)-methyl]-piperidine

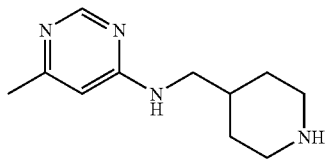

A mixture of 4-[(2-chloro-6-methyl-pyrimidin-4-ylamino)-methyl]-piperidine-1-carboxylic acid benzyl ester (EXAMPLE 57, 0.50 g, 1.33 mmol), Pd/C (10%, 0.05 g) in absolute ethanol (15 mL) was vigorously stirred under 1 atm H$_2$ for 6 h. Filtered and concentrated, the reaction gave 4-[(6-methyl-pyrimidin-4-ylamino)-methyl]-piperidine. M.S. (M+1): 207.30

Step 2:

4-[(6-Methyl-pyrimidin-4-ylamino)-methyl]-piperidine-1-carboxylic acid benzyl ester

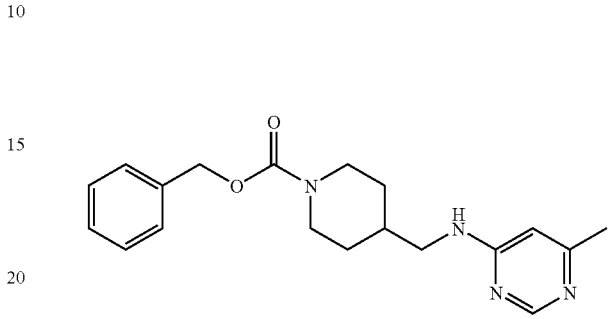

To a stirred solution of 4-[(6-methyl-pyrimidin-4-ylamino)-methyl]-piperidine (0.15 g, 0.73 mmol), in DMF (1 mL) was added carbonic acid benzyl ester 2,5-dioxo-pyrrolidin-1-yl ester (0.18 g, 0.73 mmol). The resulting reaction solution was stirred at rt for 0.5 h, then concentrated in vacuo. The residue was purified by silica gel chromatography (90:10:1 DCM MeOH NH4OH ) to give 4-[(6-methyl-pyrimidin-4-ylamino)-methyl]-piperidine-1-carboxylic acid benzyl ester. M.S. (M+1): 341.37

Example 59

4-[(2-Chloro-5-methyl-pyrimidin-4-ylamino)-methyl]-piperidine-1-carboxylic acid benzyl ester

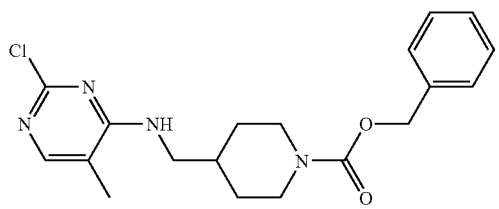

To a stirred solution of 2,4-dichloro-5-methyl-pyrimidine (3.61 g, 22.15 mmol), triethylamine (7.02 mL, 50.34 mmol) in DMF (15 mL) was slowly added benzyl-4-(aminomethyl) piperidine-1-carboxylate (EXAMPLE 13, Step 1, 5.00 g, 20.13 mmol). The resulting reaction solution was stirred at rt for 2 h, then diluted with ethyl acetate (400 mL), washed with water (3×30 mL), brine (30 mL), dried over Na$_2$SO$_4$, filtered and concentrated. The residue was purified by silica gel chromatography (20–80% ethyl acetate in hexane) to give 4-[(2-Chloro-5-methyl-pyrimidin-4-ylamino)-methyl]-piperidine-1-carboxylic acid benzyl ester. M.S. (M+1): 375.36

Example 60

4-[(5-Methyl-pyrimidin-4-ylamino)-methyl]-piperidine-1-carboxylic acid benzyl ester Step 1:

4-[(5-Methyl-pyrimidin-4-ylamino)-methyl]-piperidine

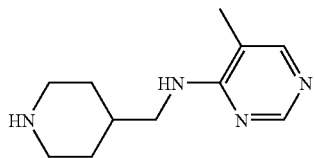

A mixture of 4-[(2-chloro-5-methyl-pyrimidin-4-ylamino)-methyl]-piperidine-1-carboxylic acid benzyl ester (EXAMPLE 59, 2.00 g, 5.34 mmol), Pd/C (10%, 0.20 g) in absolute ethanol (15 mL) was vigorously stirred under 1 atm H$_2$. Filtered and concentrated, the reaction gave 4-[(5-methyl-pyrimidin-4-ylamino)-methyl]-piperidine. M.S. (M+1): 207.29

Step 2:

4-[(5-Methyl-pyrimidin-4-ylamino)-methyl]-piperidine-1-carboxylic acid benzyl ester

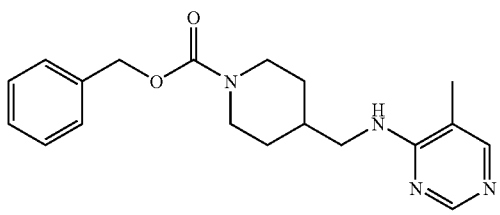

To a stirred solution of 4-[(5-methyl-pyrimidin-4-ylamino)-methyl]-piperidine (0.20 g, 0.97 mmol), in DMF (3 mL) was added carbonic acid benzyl ester 2,5-dioxo-pyrrolidin-1-yl ester (0.24 g, 0.97 mmol). The resulting reaction solution was stirred at rt for 0.5 h, then concentrated in vacuo. The residue was purified by silica gel chromatography (1–10 (10% NH$_4$OH in MeOH)/99–90 CH$_2$Cl$_2$) to give 4-[(5-methyl-pyrimidin-4-ylamino)-methyl]-piperidine-1-carboxylic acid benzyl ester.

$^1$H NMR (400 MHz, CDCl$_3$) δ 8.50 (s, 1 h, Pyr), 7.97 (s, 1 h, Pyr), 7.35 (m, 5 h, Ar), 5.13 (s, 2 h, ArCH$_2$O), 4.62 (s, 1 h, NH), 4.22 (br s, 2 h, NCH$_2$CH$_2$), 3.43 (s, 2 h, NHCH$_2$CH), 2.79 (br s, 2 h, NCH$_2$CH$_2$), 2.02 (s, 3 h, CH$_3$), 1.86 (m, 1 h, CH), 1.76 (d, J=11.7 Hz, 2 h, CHCH$_2$CH$_2$), 1.21 (q, J=9.7 Hz, 2 h, CHCH$_2$CH$_2$);
M.S. (M+1): 341.39

EXAMPLES 61–63 were prepared as described above in EXAMPLE 60, but replacing the carbonic acid benzyl ester 2,5-dioxo-pyrrolidin-1-yl ester with the appropriately substituted analog:

Example 61

4-[(5-Methyl-pyrimidin-4-ylamino)-methyl]-piperidine-1-carboxylic acid-4-methyl-benzyl ester

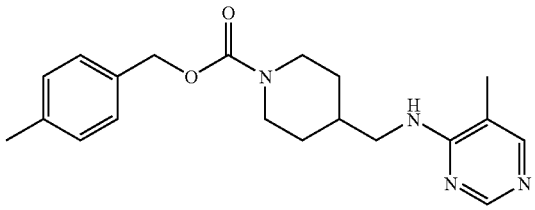

$^1$H NMR (400 MHz, CDCl$_3$) δ 8.49 (s, 1 h, Pyr), 7.97 (s, 1 h, Pyr), 7.25 (d, J=8.5 Hz, 2 h, Ar), 7.16 (d, J=7.9 Hz, 2 h, Ar), 5.08 (s, 2 h, ArCH$_2$O), 4.62 (s, 1 h, NH), 4.20 (br s, 2 h, NCH$_2$CH$_2$), 3.43 (s, 2 h, NHCH$_2$CH), 2.77 (t, J=11.0 Hz, 2 h, NCH$_2$CH$_2$), 2.35 (s, 3 h, PyrCH$_3$), 2.02 (s, 3 h, ArCH$_3$), 1.84 (m, 1 h, CH), 1.74 (d, J=9.7 Hz, 2 h, CHCH$_2$CH$_2$), 1.20 (q, J=10.6 Hz, 2 h, CHCH$_2$CH$_2$);
M.S. (M+1): 355.39

Example 62

4-[(5-Methyl-pyrimidin-4-ylamino)-methyl]-piperidine-1-carboxylic acid-4-chloro-benzyl ester

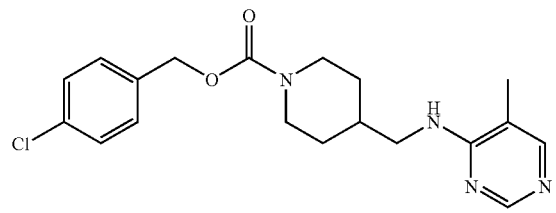

$^1$H NMR (400 MHz, CDCl$_3$) δ 8.50 (s, 1 h, Pyr), 7.97 (s, 1 h, Pyr), 7.34–7.26 (m, 4 h, Ar), 5.08 (s, 2 h, ArCH$_2$O), 4.62 (s, 1 h, NH), 4.20 (br s, 2 h, NCH$_2$CH$_2$), 3.43 (s, 2 h, NHCH$_2$CH), 2.79 (br s, 2 h, NCH$_2$CH$_2$), 2.02 (s, 3 h, CH$_3$), 1.85 (m, 1 h, CH), 1.76 (d, J=12.6 Hz, 2 h, CHCH$_2$CH$_2$), 1.20 (q, J=10.0 Hz, 2 h, CHCH$_2$CH$_2$);
M.S. (M+1): 375.35

Example 63

4-[(5-Methyl-pyrimidin-4-ylamino)-methyl]-piperidine-1-carboxylic acid-4-fluoro-benzyl ester

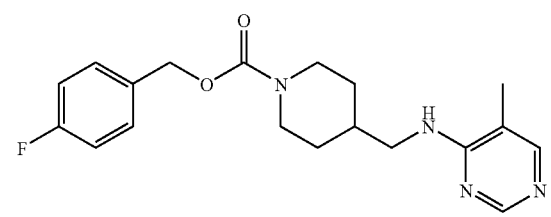

¹H NMR (400 MHz, CD₃OD) δ 8.56 (s, 1 h, Pyr), 7.96 (s, 1 h, Pyr), 7.38 (dd, J=5.6 & 5.4 Hz, 2 h, Ar), 7.08 (t, J=8.7 Hz, 2 h, Ar), 5.08 (s, 2 h, ArCH₂O), 4.14 (d, J=13.3 Hz, 2 h, NCH₂CH₂), 6.94 (d, J=6.9 Hz, 2 h, NHCH₂CH), 2.81 (br s, 2 h, NCH₂CH₂), 2.15 (s, 3 h, CH₃), 1.95 (m, 1 h, CH), 1.74 (d, J=11.4 Hz, 2 h, CHCH₂CH₂), 1.17 (q, J=9.2 Hz, 2 h, CHCH₂CH₂);

M.S. (M+1): 359.36

Example 64

4-[(2-Amino-6-methyl-pyrimidin-4-ylamino)-methyl]-piperidine-1-carboxylic acid benzyl ester Step 1:

4-{[2-(2,4-Dimethoxy-benzylamino)-6-methyl-pyrimidin-4-ylamino]-methyl}-piperidine-1-carboxylic acid benzyl ester

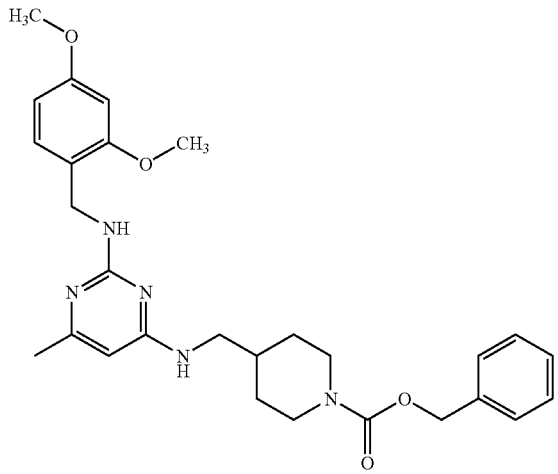

A stirred solution of 4-[(2-chloro-6-methyl-pyrimidin-4-ylamino)-methyl]-piperidine-1-carboxylic acid benzyl ester (EXAMPLE 57, 0.5 g, 1.33 mmol) in 2,4-dimethoxybenzylamine (1.00 mL, 6.67 mmol) was heated at 100° C. for 6 h, then cooled to rt and purified by silica gel chromatography [1–10 (10% NH₄OH in MeOH)/99–90 CH₂Cl₂)] to give 4-{[2-(2,4-dimethoxy-benzylamino)-6-methyl-pyrimidin-4-ylamino]-methyl}-piperidine-1-carboxylic acid benzyl ester. M.S. (M+1): 506.46

Step 2:

4-[(2-Amino-6-methyl-pyrimidin-4-ylamino)-methyl]-piperidine-1-carboxylic acid benzyl ester

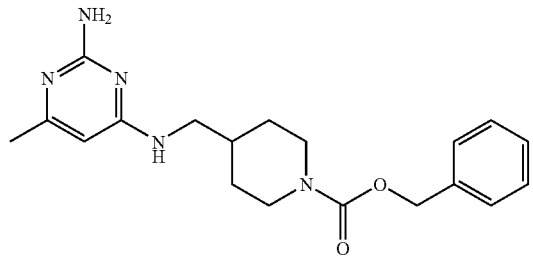

To a stirred solution of the 4-{[2-(2,4-dimethoxy-benzylamino)-6-methyl-pyrimidin-4-ylamino)-methyl}-piperidine-1-carboxylic acid benzyl ester from Step 1 above (0.4 g, 0.79 mmol) in CH₂Cl₂ (5 mL) was added trifluoroacetic acid (1 mL). The resulting reaction solution was stirred at rt for 1 h, then concentrated in vacuo. The residue was purified by silica gel chromatography (1–10 (10% NH₄OH in MeOH)/99–90 CH₂Cl₂) to give 4-[(2-amino-6-methyl-pyrimidin-4-ylamino)-methyl]-piperidine-1-carboxylic acid benzyl ester. M.S. (M+1): 356.36

Example 65

4-[(5,6-Dichloro-pyridazin-4-ylamino)-methyl]-piperidine-1-carboxylic acid benzyl ester Step 1:

3,4,5-Trichloropyridazine

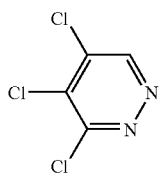

A stirred solution of 4,5-dichloro-2,3-dihydro-3-pyridazinone (15.00 g, 90.92 mmol) in POCl₃ (100 mL) was refluxed for 1.5 h, then concentrated in vacuo. The residue was dissolved in CH₂Cl₂ (400 mL), washed with water (100 mL), dried over Na₂SO₄, filtered and concentrated to give 3,4,5-trichloropyridazine.

M.S. (M+1): 185.00

Step 2:

4-[(5,6-Dichloro-pyridazin-4-ylamino)-methyl]-piperidine-1-carboxylic acid benzyl ester

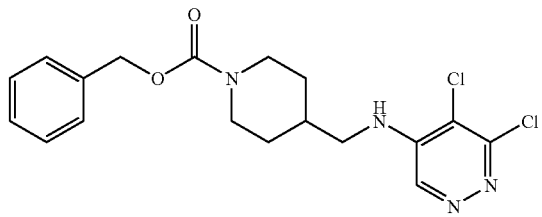

To a stirred solution of 3,4,5-trichloropyridazine (2.22 g, 12.08 mmol) and DIPEA (4.21 mL, 24.16 mmol) in IPA (25 mL) was added benzyl-4-(aminomethyl)piperidine-1-carboxylate (EXAMPLE 13, Step 1, 3.00 g, 12.08 mmol). The resulting reaction solution was stirred at rt for 5 h, then concentrated in vacuo. The residue was dissolved in CH₂Cl₂ (200 mL), washed with water (50 mL), dried over Na₂SO₄, filtered and concentrated. The crude product was purified by silica gel chromatography (1–7 (10% NH₄OH in MeOH)/99–93 CH₂Cl₂) to give 4-[(5,6-dichloro-pyridazin-4-ylamino)-methyl]-piperidine-1-carboxylic acid benzyl ester.

M.S. (M+1): 395.28

Example 66

4-[(Pyridazin-4-ylamino)-methyl]-piperidine-1-carboxylic acid benzyl ester

Step 1:

4-[(Pyridazin-4-ylamino)-methyl]-piperidine

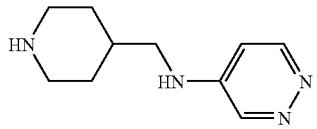

A mixture of 4-[(5,6-dichloro-pyridazin-4-ylamino)-methyl]-piperidine-1-carboxylic acid benzyl ester (EXAMPLE 65, 2.00 g, 5.06 mmol), Pd/C (10%, 0.20 g) in absolute ethanol (15 mL) was vigorously stirred under 1 atm $H_2$ provided by a $H_2$ balloon for 7 h. Filtered and concentrated, the reaction gave 4-[(Pyridazin-4-ylamino)-methyl]-piperidine. M.S. (M+1): 193.25

Step 2:

4-[(Pyridazin-4-ylamino)-methyl]-piperidine-1-carboxylic acid benzyl ester

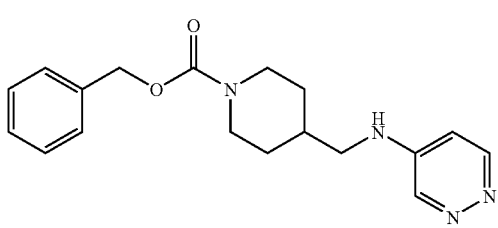

To a stirred solution of 4-[(pyridazin-4-ylamino)-methyl]-piperidine (0.20 g, 1.04 mmol), in DMF (3 mL) was added carbonic acid benzyl ester 2,5-dioxo-pyrrolidin-1-yl ester (0.26 g, 1.04 mmol). The resulting reaction solution was stirred at rt for 0.5 h, then concentrated in vacuo. The residue was purified by silica gel chromatography (1–7 (10% $NH_4OH$ in MeOH)/99–93 $CH_2Cl_2$) to give 4-(pyridazin-4-ylamino)-methyl]-piperidine-1-carboxylic acid benzyl ester.

$^1$H NMR (400 MHz, CDCl$_3$) δ 8.65 (d, J=6.1 Hz, 1 h, Pyr), 8.57 (d, J=3.1 Hz, 1 h, Pyr), 7.36 (m, 5 h, Ar), 6.46 (dd, J=6.1 & 2.9 Hz, 1 h, Pyr), 5.13 (s, 2 h, ArCH$_2$O), 4.40 (s, 1 h, NH), 4.25 (br s, 2 h, NCH$_2$CH$_2$), 3.10 (t, J=6.0 Hz, 2 h, NHCH$_2$CH), 2.78 (br s, 2 h, NCH$_2$CH$_2$), 1.81 (m, 1 h, CH), 1.77 (d, J=12.5 Hz, 2 h, CHCH$_2$CH$_2$), 1.23 (q, J=10.3 Hz, 2 h, CHCH$_2$CH$_2$);

M.S. (M+1): 327.28

Example 67

4-[(Pyridazin-4-ylamino)-methyl]-piperidine-1-carboxylic acid-4-fluoro-benzyl ester

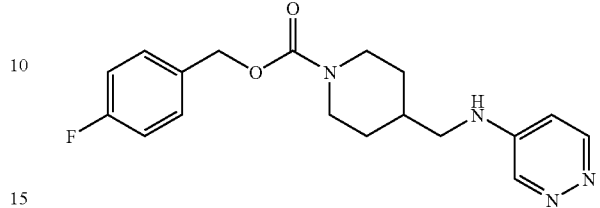

To a stirred solution of 4-[(pyridazin-4-ylamino)-methyl]-piperidine (0.20 g, 1.04 mmol, from EXAMPLE 66, Step 1) in DMF (3 mL) was added carbonic acid-4-fluoro-benzyl ester 2,5-dioxo-pyrrolidin-1-yl ester (0.28 g, 1.04 mmol). The resulting reaction solution was stirred at rt for 0.5 h, then concentrated in vacuo. The residue was purified by silica gel chromatography (1–7 (10% $NH_4OH$ in MeOH)/99–93 $CH_2Cl_2$) to give 4-[(pyridazin-4-ylamino)-methyl]-piperidine-1-carboxylic acid-4-fluoro-benzyl ester. M.S. (M+1): 345.29

Examples 68A and 68B

Example 68A

4-[(6-Chloro-pyridazin-4-ylamino)-methyl]-piperidine-1-carboxylic acid benzyl ester

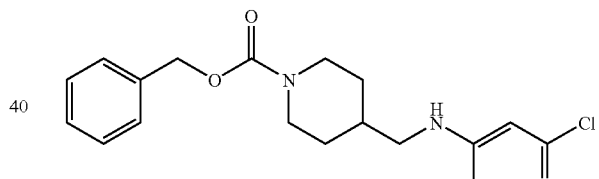

Example 68B

4-[(5-Chloro-pyridazin-4-ylamino)-methyl]-piperidine-1-carboxylic acid benzyl ester

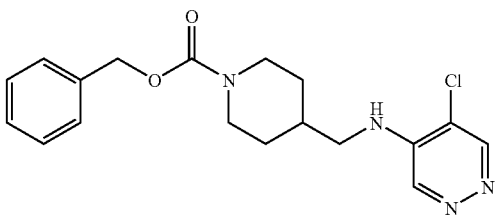

A mixture of 4-[(5,6-dichloro-pyridazin-4-ylamino)-methyl]piperidine-1-carboxylic acid benzyl ester (EXAMPLE 65, 0.15 g, 0.38 mmol), washed Raney Nickel (0.15 g), $NH_4OH$ (1 mL) in absolute ethanol (10 mL) was vigorously stirred under 1 atm $H_2$ for 7 h. The reaction mixture was filtered and concentrated and the residue was purified by silica gel chromatography (1–7 (10% NH₄OH in MeOH)/99–93 CH₂Cl₂) to give 4-[(6-chloro-pyridazin-4-ylamino)-methyl]-piperidine-1-carboxylic acid benzyl ester. M.S. (M+1): 361.25 and 4-[(5-chloro-pyridazin-4-ylamino)-methyl]-piperidine-1-carboxylic acid benzyl ester. M.S. (M+1): 361.25

Example 69

4-[(2-Chloro-5-fluoro-pyrimidin-4-ylamino)-methyl]-piperidine-1-carboxylic acid benzyl ester Step 1:
2,4-Dichloro-5-fluoro-pyrimidine

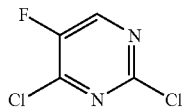

A solution of 5-fluoro-uracil (5.00 g, 38.44 mmol) and N,N-dimethylaniline (5 mL) in POCl₃ (20 mL) was refluxed for 1 h. The solution was then concentrated in vacuo. The resulting residue was quenched with water (20 mL) at 0° C., and extracted with ether (3×150 mL). The combined ether layers were washed with water (2×50 mL), sat. aq. NaHCO₃, water (50 mL), dried over Na₂SO₄, filtered and concentrated to give 2,4-dichloro-5-fluoro-pyrimidine compound.

Step 2:
4-[(2-Chloro-5-fluoro-pyrimidin-4-ylamino)-methyl]-piperidine-1-carboxylic acid benzyl ester

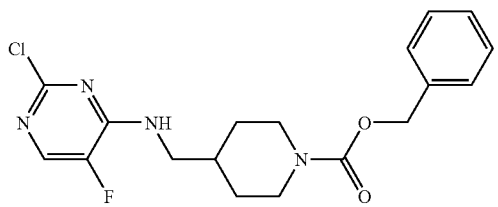

To a stirred solution of 2,4-dichloro-5-fluoro-pyrimidine (0.67 g, 4.03 mmol) and triethylamine (0.84 mL, 6.04 mmol) in DMF (5 mL) was added benzyl 4-(aminomethyl)piperidine-1-carboxylate (EXAMPLE 13, Step 1) (1.00 g, 4.03 mmol). The resulting reaction solution was stirred at rt for 1 h, and concentrated in vacuo. The residue was purified by silica gel chromatography (CH₂Cl₂/IPA/hexanes) to give 4-[(2-chloro-5-fluoro-pyrimidin-4-ylamino)-methyl]-piperidine-1-carboxylic acid benzyl ester. M.S. (M+1): 379.25

Example 70

4-[(5-Fluoro-pyrimidin-4-ylamino)-methyl]-piperidine-1-carboxylic acid benzyl ester

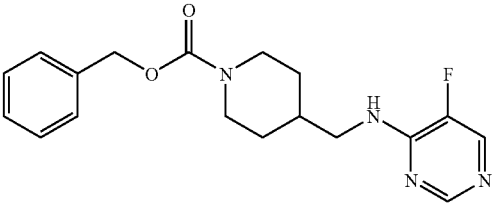

A mixture of 4-[(2-chloro-5-fluoro-pyrimidin-4-ylamino)-methyl]piperidine-1-carboxylic acid benzyl ester (EXAMPLE 69, 0.15 g, 0.40 mmol), washed Raney-Nickel® (0.15 g), NH₄OH (1 mL) in absolute ethanol (10 mL) was vigorously stirred under 1 atm H₂ for 2 h. The reaction mixture was filtered and concentrated and the residue was purified by silica gel chromatography (1–10 (10% NH₄OH in MeOH)/99–90 CH₂Cl₂) to give 4-[(5-fluoro-pyrimidin-4-ylamino)-methyl]-piperidine-1-carboxylic acid benzyl ester. M.S. (M+1): 345.28

Example 71

4-[(5-Fluoro-pyrimidin-2-ylamino)-methyl]-piperidine-1-carboxylic acid benzyl ester Step 1:
2-Chloro-5-fluoro-pyrimidine

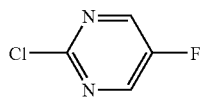

To a refluxing mixture of 2,4-dichloro-5-fluoro-pyrimidine (EXAMPLE 69, Step 1, 3.25 g, 19.47 mmol) and zinc (8–30 mesh, 3.82 g, 58.39 mmol) in THF (30 mL) was slowly added acetic acid (1.11 mL, 19.47 mmol). This reaction mixture was refluxed for 7 h, then cooled to rt, filtered and concentrated to give 2-chloro-5-fluoro-pyrimidine compound.

Step 2:
4-[(5-Fluoro-pyrimidin-2-ylamino)-methyl]-piperidine-1-carboxylic acid benzyl ester

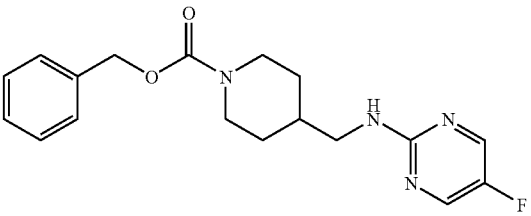

A solution of benzyl-4-(aminomethyl)piperidine-1-carboxylate (EXAMPLE 13, Step 1, 0.10 g, 0.40 mmol), 2-chloro-5-fluoro-pyrimidine (0.053 g, 0.40 mmol) and triethylamine (0.11 mL, 0.81 mmol) in DMF (0.5 mL) was heated at 100° C. for 6 h, then concentrated in vacuo. The residue was purified by silica gel chromatography (10 CH$_2$Cl$_2$: 1–20 IPA: 89–70 hexane) to give 4-[(5-fluoro-pyrimidin-2-ylamino)-methyl]-piperidine-1-carboxylic acid benzyl ester.

M.S. (M+1): 345.29

Example 72

4-[(5-Fluoro-pyrimidin-2-ylamino)-methyl]-piperidine-1-carboxylic acid-4-methyl-benzyl ester

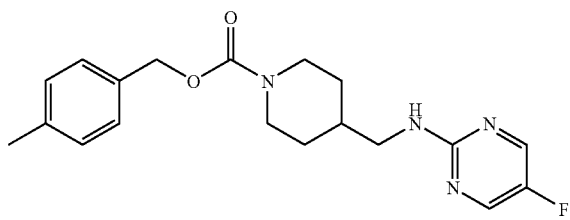

The solution of (4-methyl-benzyl)-4-(aminomethyl)piperidine-1-carboxylate (INTERMEDIATE 2a) (0.20 g, 0.76 mmol), 2-chloro-5-fluoro-pyrimidine (EXAMPLE 71, Step 1) (0.10 g, 0.76 mmol) and triethylamine (0.21 mL, 1.53 mmol) in DMF (1 mL) was heated at 100° C. for 6 h, then concentrated in vacuo. The residue was purified by silica gel chromatography (10 CH$_2$Cl$_2$: 1–10 IPA: 89–80 hexane) to give 4-[(5-fluoro-pyrimidin-2-ylamino)-methyl]-piperidine-1-carboxylic acid-4-methyl-benzyl ester. M.S. (M+1): 359.33

Example 73

4-[(5-Fluoro-pyrimidin-2-ylamino)-methyl]-piperidine-1-carboxylic acid-4-cyclopropyl-benzyl ester Step 1:
4-Cyclopropyl-benzoic acid ethyl ester

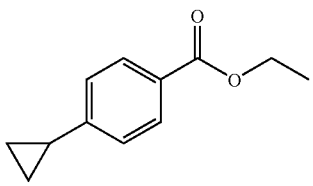

Indium trichloride (2.2 g, 10 mmol) and THF (50 mL) were combined under nitrogen and cooled to −70° C. Cyclopropylmagnesium bromide solution (33 mL, 30 mmol, 0.92 M) was added dropwise while maintaining the reaction temperature ≦−60° C. After the addition was complete, the reaction was stirred 0.5 h with cooling then 0.5 h with the cooling bath removed. The resulting solution was added via cannula to a refluxing solution of ethyl-4-iodobenzoate (5.5 g, 20 mmol), trans-dichlorobis(triphenylphosphine)palladium(II) (421 mg, 0.60 mmol) and THF (100 mL) under nitrogen. After 24 h, the contents of the reaction flask were cooled and the solvent was removed in vacuo. Water (100 mL) and 5% KHSO$_4$ were added and the mixture was extracted with CH$_2$Cl$_2$ (3×100 mL). The combined organic extracts were washed with brine, dried with Na$_2$SO$_4$ and filtered. The filtrate was removed in vacuo and the remaining residue was purified by flash column chromatography (hexane:EtOAc 95:5) to give 4cyclopropyl-benzoic acid ethyl ester as an orange oil.

Step 2:
(4-Cyclopropyl-phenyl)-methanol

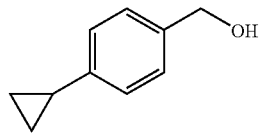

4-Cyclopropyl-benzoic acid ethyl ester (2.46 g, 13 mmol), and THF (250 mL) were combined under nitrogen and cooled in an IPA/dry ice bath to −70° C. Lithium aluminum hydride solution (20 mL, 20 mmol, 1.0M) was added dropwise. After 2 h excess lithium aluminum hydride was quenched by adding EtOAc dropwise. The reaction was warmed to 25° C., then the solvent was removed in vacuo. Water (200 mL) and a few drops of HCl (aq, 6N) were added. The mixture was extracted with EtOAc (3×100 mL). The combined organic extracts were washed with brine, dried with NA$_2$SO$_4$ and filtered. The filtrate was removed in vacuo and the remaining residue was purified by flash column chromatography (hexane:EtOAc 40:60) to give (4-cyclopropyl-phenyl)-methanol as a colorless oil.

Step 3:
Carbonic acid 4-cyclopropyl-benzyl ester 2,5-dioxo-pyrrolidin-1-yl ester

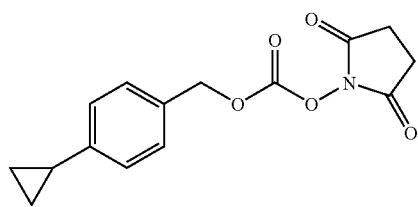

The title compound was prepared from (4-cyclopropyl-phenyl)-methanol as described for similar compounds previously (Chem. Pharm. Bull., 38(1):110–115(1990) and INTERMEDIATE 1A).

Step 4:
4-Aminomethyl-piperidine-1-carboxylic acid 4-cyclopropyl-benzyl ester

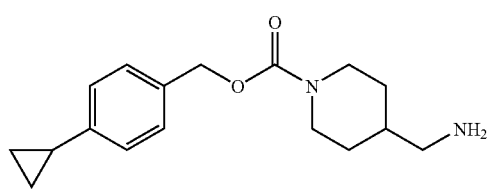

The title compound was prepared from carbonic acid 4-cyclopropyl-benzyl ester 2,5-dioxo-pyrrolidin-1-yl ester as described in EXAMPLE 13, Step 1.

Step 5:

4-[(5-Fluoro-pyrimidin-2-ylamino)-methyl]-piperidine-1-carboxylic acid-4-cyclopropyl-benzyl ester

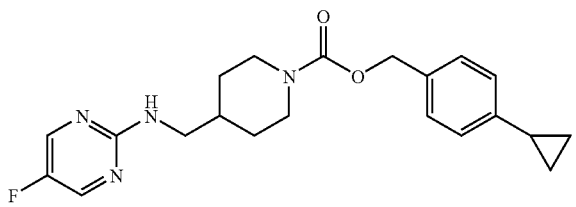

A solution of (4-cyclopropyl-benzyl)-4-(aminomethyl)piperidine-1-carboxylate (0.10 g, 0.35 mmol), 2-chloro-5-fluoro-pyrimidine (EXAMPLE 71, Step 1, 0.046 g, 0.35 mmol) and triethylamine (0.097 mL, 0.69 mmol) in DMF (1 mL) was heated at 100° C. for 6 h, then concentrated in vacuo. The residue was purified by silica gel chromatography ($CH_2Cl_2$/IPA/hexanes) to give 4-[(5-fluoro-pyrimidin-2-ylamino)-methyl]-piperidine-1-carboxylic acid-4-cyclopropyl-benzyl ester.

M.S. (M+1): 385.31

Example 74

4-[(5-Fluoro-pyrimidin-2-ylamino)-methyl]-piperidine-1-carboxylic acid-4-chloro-benzyl ester

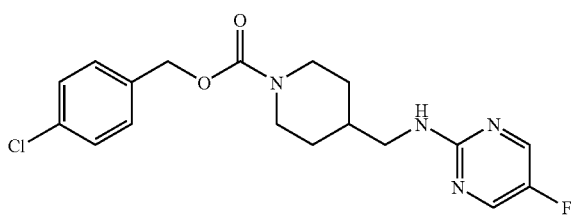

A solution of (4-chloro-benzyl)-4-(aminomethyl)piperidine-1-carboxylate (INTERMEDIATE 2B) (0.10 g, 0.35 mmol), 2-chloro-5-fluoro-pyrimidine (0.047 g, 0.35 mmol) and triethylamine (0.099 mL, 0.71 mmol) in DMF (1 mL) was heated at 100° C. for 6 h, then concentrated in vacuo. The residue was purified by silica gel chromatography ($CH_2Cl_2$/IPA/hexanes) to give 4-[(5-fluoro-pyrimidin-2-ylamino)-methyl]-piperidine-1-carboxylic acid-4-chloro-benzyl ester. M.S. (M+1): 379.26

Example 75

4-[(5-Fluoro-pyrimidin-2-ylamino)-methyl]-piperidine-1-carboxylic acid-4-fluoro-benzyl ester

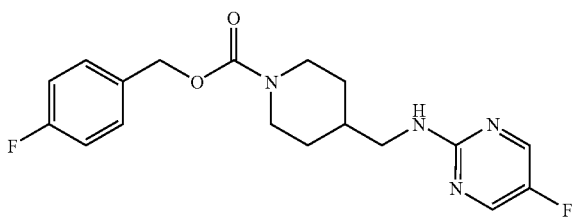

A solution of (4-fluoro-benzyl)-4-(aminomethyl)piperidine-1-carboxylate (INTERMEDIATE 2C) (0.10 g, 0.38 mmol), 2-chloro-5-fluoro-pyrimidine (0.05 g, 0.38 mmol) and triethylamine (0.11 mL, 0.75 mmol) in DMF (1 mL) was heated at 100° C. for 6 h, then concentrated in vacuo. The residue was purified by silica gel chromatography ($CH_2Cl_2$/IPA/hexanes) to give 4-[(5-fluoro-pyrimidin-2-ylamino)-methyl]-piperidine-1-carboxylic acid-4-fluoro-benzyl ester. M.S. (M+1): 363.31

Example 76

4-Methylbenzyl 4-[(2-pyrimidinylamino)methyl]-1-piperidinecarboxylate

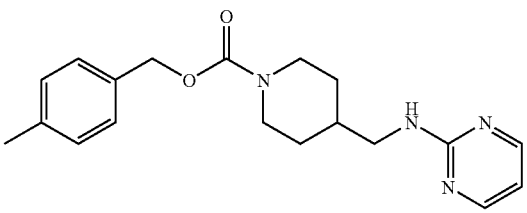

A stirred solution of 4-methylbenzyl 4-(aminomethyl)-1-piperidinecarboxylate (INTERMEDIATE 2A) (20.00 g, 76.23 mmol), 2-chloro-pyrimidine (8.73 g, 76.23 mmol) and triethylamine (21.25 mL, 152.46 mmol) in DMF (40 mL) was heated at 100° C. for 6 h. The reaction solution was cooled to rt, then diluted with ethyl acetate (800 mL), washed with sat. aq. $NaHCO_3$ (100 mL), water (3×100 mL), brine (100 mL), dried over $Na_2SO_4$, filtered and concentrated. The residue was purified by silica gel chromatography ($CH_2Cl_2$/IPA/hexanes) to give 4-methylbenzyl 4-[(2-pyrimidinylamino)methyl]-1-piperidinecarboxylate. M.S. (M+1): 341.30

Example 77

[1-(2-Phenyl-ethanesulfonyl)-piperidin-4-ylmethyl]-pyrimidin-2-yl-amine

Step 1:

4-Aminomethyl-piperidine-1-carboxylic acid tert-butyl ester

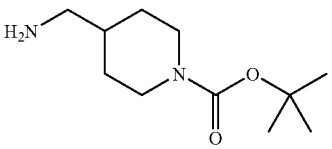

To a mixture of 4-aminomethylpiperidine (15 g) in 250 mL of anhydrous tetrahydrofuran cooled to −78° C. was added, dropwise over 45 min., a solution of di-tert-butyl di-carbonate (24 g) in 100 mL of anhydrous tetrahydrofuran. After stirring for 1 h at −78° C., the mixture was allowed to warm to room temperature and stirred overnight. The mixture was concentrated to near dryness and diluted with 200 mL of 10% aqueous citric acid. The mixture was extracted with 3×100 mL of ether, then made basic with sodium hydroxide pellets and extracted with 3×20 mL of chloroform. The combined chloroform extracts were dried over magnesium sulfate and concentrated to dryness under reduced pressure. The resulting oil was homogeneous by TLC (development with 90:10 chloroform saturated with ammonia: methanol).

$^1$H NMR (400 MHz, CDCl$_3$): δ 4.1 (br s, 2H), 2.7 (br m, 2H), 2.6 (d, 2H), 1.7 (m, 3H), 1.42 (s, 9H), 1.1 (m, 2H).

Step 2:
4-(Benzyloxycarbonylamino-methyl)-piperidine-1-carboxylic acid tert-butyl ester

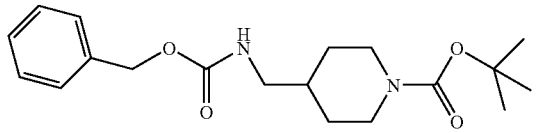

To a solution of 4-aminomethyl-piperidine-1-carboxylic acid tert-butyl ester (21 g) in 100 mL of ethyl acetate cooled to 0° C. was added 100 mL of saturated sodium carbonate and benzyl chloroformate (17 g). The solution was stirred for 3 h, then separated. The organic layer was dried over magnesium sulfate and concentrated under reduced pressure. Drying under vacuum gave the product as an oil:

$^1$H NMR (400 MHz, CDCl$_3$): δ 7.35 (m, 5H), 5.3 (d, 1H), 5.1 (s, 2H), 4.1 (br s, 2H), 3.0 (br m, 2H), 2.6 (br m, 2H), 1.7 (m, 3H), 1.42 (s, 9H), 1.1 (m, 2H).

Step 3:
Piperidin-4-ylmethyl-carbamic acid benzyl ester

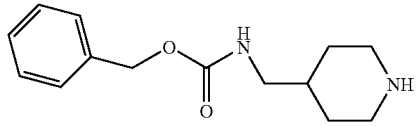

A mixture of 4-(benzyloxycarbonylamino-methyl)-piperidine-1-carboxylic acid tert-butyl ester (35 g) and 50 mL of 4N HCl in dioxane was stirred at room temperature for 3 h, then diluted with 200 mL of ether and filtered. There was obtained piperidin-4-ylmethyl-carbamic acid benzyl ester hydrochloride salt as a white fluffy solid. The free base was obtained by partitioning the hydrochloride between chloroform (50 mL) and saturated aqueous Na$_2$CO$_3$ (50 mL).

$^1$H NMR (400 MHz, CDCl$_3$ ): δ 7.35 (m, 5H), 5.15 (s, 2H), 4.9 (br s, 1H), 3.1 (m, 2H), 2.6 (m, 3H), 1.7 (m, 2H), 1.6 (m, 2H), 1.1 (m, 2H).

MS (m+1)=249.

Step 4:
[1-(2-Phenyl-ethenesulfonyl)-piperidin-4-ylmethyl]-carbamic acid benzyl ester

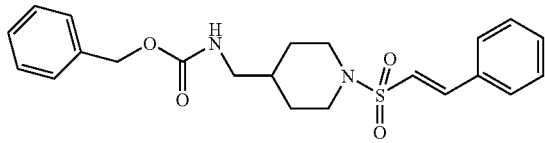

A mixture of piperidin-4-ylmethyl-carbamic acid benzyl ester hydrochloride (2 g), 25 mL of dichloromethane, trans-2-styrenesulfonyl chloride (1.5 g), and 3 mL of N,N-diisopropylethylamine was stirred at room temperature overnight, then diluted with 200 mL af chloroform and washed with 100 mL of saturated sodium carbonate. The chloroform extracts were dried over magnesium sulfate and concentrated. There was obtained [1-(2-phenyl-ethenesulfonyl)-piperidin-4-ylmethyl]-carbamic acid benzyl ester as a white solid.

$^1$H NMR (400 MHz, CDCl$_3$ ): δ 7.5–7.2 (m, 10H), 6.65 (m, 1H), 5.15 (s, 2H), 4.8 (br s, 1 H), 3.8 (d, 2H), 3.1 (dd, 2H), 2.6 (dd, 2H), 1.8 (d, 2H), 1.6 (m, 2H), 1.35 (m, 2H)

MS (m+1)=415.

Step 5:
C-[1-(2-Phenyl-ethanesulfonyl)-piperidin-4-yl]-methylamine

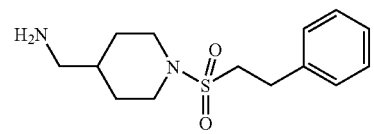

A mixture of [1-(2-phenyl-ethenesulfonyl)-piperidin-4-ylmethyl]-carbamic acid benzyl ester (2.5 g), 20% palladium hydroxide (1 g) on carbon, 200 mL of methanol and 50 mL of tetrahydrofuran were shaken under 50 psi of hydrogen for 2 days at room temperature. The catalyst was filtered off and washed with 250 mL of methanol. Concentration under reduced pressure gave C-[1-(2-phenyl-ethanesulfonyl)-piperidin-4-yl]-methylamine as white solid.

$^1$H NMR (400 MHz, CDCl$_3$ ): δ 7.4–7.2 (m, 5H), 5.1 (s, 2H), 3.8 (d, 2H), 3.1 (m, 4H), 2.7 (dd, 2H), 1.8 (d, 2H), 1.6 (m, 5H), 1.3 (m, 2H)

MS (m+1)=283.

Step 6:
[1-(2-Phenyl-ethanesulfonyl)-piperidin-4-ylmethyl]-pyrimidin-2-yl-amine

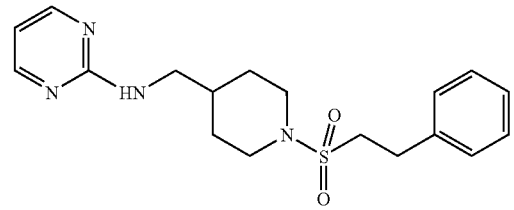

A mixture of 0.5 g of [1-(2-phenyl-ethanesulfonyl)-piperidin-4ylmethyl]-pyrimidin-2-yl-amine, 0.56 g of 2-bromopyrimidine, 25 mL of 2-propanol and 0.5 mL of N,N-diisopropylethylamine was heated to reflux overnight. Purification of the residue obtained after concentration under reduced pressure by chromatography on silica, eluting with ethyl acetate gave [1-(2-phenyl-ethanesulfonyl)-piperidin-4-ylmethyl]-pyrimidin-2-yl-amine as a white solid.

$^1$H NMR (400 MHz, CDCl$_3$)): δ 8.15 (d, 2H), 7.3–7.18 (m, 5H), 6.5 (dd, 1H), 5.5 (dd, 1H), 3.8 (d, 2H), 3.35 (d, 2H), 3.15 (dd, 4H), 2.7 (m, 2H), 1.9 (d, 2H), 1.8 (m, 1H), 1.3 (m, 2H)

MS (m+1)=361.

Example 78

{1-[2-(4-Fluoro-phenyl)-ethanesulfonyl]-piperidin-4-yl-methyl}-pyrimidin-2-yl-amine Step 1:

1-(2-Chloro-ethyl)-4-fluoro-benzene

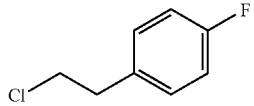

A mixture of 7 g 2-(4-fluoro-phenyl)-ethanol, 25 mL of chlorobenzene, 42 mL of 37% HCl, and 0.9 g of Aliquot® 336 (tricaprylylmethyl ammonium chloride) was heated to reflux for 3 days, cooled and extracted into 3×100 mL of hexane. The combined extracts were dried over magnesium sulfate and concentrated under reduced pressure. The resulting oil was mainly 1-(2-chloro-ethyl)-4-fluoro-benzene:

$^1$H NMR (400 MHz, CDCl$_3$): δ 7.3 (dd, 2H), 7.0 (dd, 2H), 3.7 (t, 2H), 3.05 (t, 2H).

Step 2:

Thioacetic acid S-[2-(4-fluoro-phenyl)-ethyl]ester

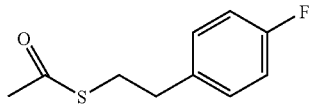

A mixture of 2.4 g of 1-(2-chloro-ethyl)-4-fluoro-benzene, 30 mL of DMF and 25 mL of potassium thioacetate was stirred under nitrogen for 24 h. The mixture was diluted with 200 mL of water and extracted with 3×50 mL of dichloromethane. The combined organic layers were dried over magnesium sulfate and concentrated under reduced pressure. Drying under vacuum gave an oil:

$^1$H NMR (400 MHz, CDCl$_3$): δ 7.18 (dd, 2H), 6.98 (dd, 2H), 3.08 (t, 2H), 2.81 (t, 2H), 2.32 (s, 3H).

Step 3:

2-(4-Fluoro-phenyl)-ethanesulfonyl chloride

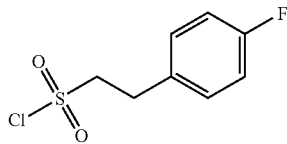

A stream of chlorine gas was dispersed into a stirred, ice cold mixture of 2.5 g of thioacetic acid S-[2-(4-fluoro-phenyl)-ethyl]ester, 30 mL of dichloromethane and 30 mL of water over 1 h. The mixture was diluted with 200 mL of dichloromethane, shaken and separated. The combined organic layers were dried over magnesium sulfate and concentrated under reduced pressure. Trituration with hexane gave a white solid:

$^1$H NMR (400 MHz, CDCl$_3$): δ 7.2 (dd, 2H), 7.0 (dd, 2H), 3.1 (dd, 2H), 3.3 (dd, 2H), 2.32 (s, 3H).

Step 4:

4-(tert-Butoxycarbonylamino-methyl)-piperidine-1-carboxylic acid benzyl ester

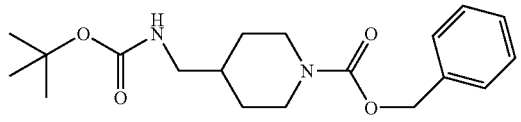

To an ice cold, stirred solution of 21 g of benzyl 4-(aminomethyl)piperidine-1-carboxylate (EXAMPLE 13, Step1) in 250 mL of dichloromethane was added 18 g of di-tert-butyldicarbonate in 100 mL of dichloromethane over 30 min. After stirring overnight, the mixture was concentrated to dryness. Trituration with hexane gave a white solid:

$^1$H NMR (400 MHz, CDCl$_3$): δ 7.4 (m, 5H), 5.15 (s, 2H), 4.6 (br s, 1H), 4.2 (br s, 2H), 3.0 (br s, 2H), 2.8 ((m, 2H), 1.7 (m, 3H), 1.42 (s, 9H), 1.15 (m, 2H).

Step 5:

Piperidin-4-ylmethyl-carbamic acid tert-butyl ester

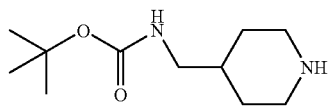

A mixture of 28 g of 4-(tert-butoxycarbonylamino-methyl)-piperidine-1-carboxylic acid benzyl ester, 1 g of 10% palladium on carbon, 100 mL of THF and 200 mL of methanol was stirred under an atmosphere of hydrogen for 2 days. The mixture was filtered concentrated under reduced pressure. Drying under reduced pressure gave a white solid:

$^1$H NMR (400 MHz, CDCl$_3$): δ 4.8 (br s, 1H), 3.05 (d, 2H), 2.9 (dd, 2H), 2.6 (m, 3H), 1.6 (d, 2H), 1.5 (m, 1H), 1.4 (s, 9H), 1.05 (m, 2H).

Step 6:

{1-[2-(4-Fluoro-phenyl)-ethanesulfonyl]-piperidin-4-yl-methyl}-carbamic acid tert-butyl ester

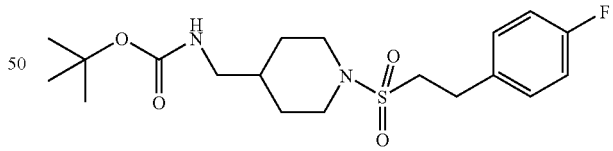

To an ice cold, stirred solution of 0.2 g of piperidin-4-ylmethyl-carbamic acid tert-butyl ester and 0.2 mL of N,N-diisopropylethylamine in 20 mL of dichloromethane was added 0.3 g of 2-(4-fluoro-phenyl)-ethanesulfonyl chloride. After stirring overnight the mixture was diluted with 50 mL of chloroform, washed with 50 mL of saturated sodium carbonate, dried over magnesium sulfate and concentrated to dryness under reduced pressure. Trituration with hexane gave a white solid:

$^1$H NMR (400 MHz, CDCl$_3$): δ 7.2 (m, 2H), 7.0 (dd, 2H), 4.6 (br m, 1H), 3.8 (d, 2H), 3.1 (m, 3H), 3.0 (m, 2H), 2.7 (dd, 2H), 1.8 (d, 2H), 1.6 (br m, 2H), 1.42 (s, 9H), 1.3 (m, 2H).

Step 7:
C-{1-[2-(4-Fluoro-phenyl)-ethanesulfonyl]-piperidin-4-yl}-methylamine

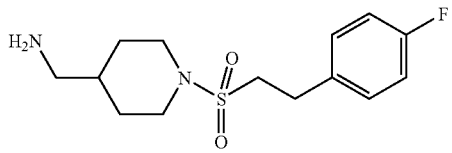

A mixture of 0.4 g of {1-[2-(4-fluoro-phenyl)-ethanesulfonyl]-piperidin-4-ylmethyl}-carbamic acid tert-butyl ester and 5 mL of 4N HCl in dioxane was stirred at room temperature for 3 h, then diluted with 50 mL of chloroform, washed with 50 mL of saturated sodium carbonate, dried over magnesium sulfate and concentrated to dryness under reduced pressure. The product was a white solid:

$^1$H NMR (400 MHz, CDCl$_3$): δ 7.2 (m, 2H), 7.0 (dd, 2H), 3.92 (d, 2H), 3.1 (s, 4H), 2.7 (dd, 2H), 2.6 (d, 2H), 1.8 (d, 2H), 1.5 (br m, 3H), 1.3 (m, 2H)

MS (m+1)=301.

Step 8:
{1-[2-(4-Fluoro-phenyl)-ethanesulfonyl]-piperidin-4-ylmethyl}-pyrimidin-2-yl-amine

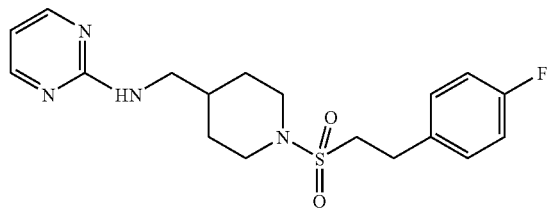

A mixture of 0.3 g of C-{1-[2-(4-Fluoro-phenyl)-ethanesulfonyl]-piperidin-4-yl}-methylamine, 0.3 g of 2-bromopyrimidine, 25 mL of 2-propanol and 0.3 mL of N,N-diisopropylethylamine was heated to reflux overnight. Purification of the residue obtained after concentration under reduced pressure by preparative chromatography, eluting with ethyl acetate gave a white solid.

$^1$H NMR (400 MHz, CDCl$_3$ ): δ 8.25 (d, 2H), 7.2 (m, 2H), 7.0 (dd, 2H), 6.58 (dd, 1H), 5.25 (br m, 1H), 3.82 (d, 2H), 3.4 (dd, 2H), 3.15 (s, 4H), 2.75 (dd, 2H), 1.9 (d, 2H), 1.8 (m, 1H), 1.3 (m, 2H)

MS (m+1)=379.

Example 79

3-(Pyrimidin-2-ylaminomethyl)-pyrrolidine-1-carboxylic acid benzyl ester

Step 1:
1-Benzyl-pyrrolidine-3-carboxylic acid amide

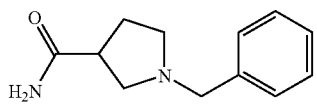

To a mixture of 4.4 g 1-benzyl-pyrrolidine-3-carboxylic acid methyl ester (M. J. Kornet, P. A. Thio, S. E. Tan, *J. Organic Chemistry*, 33:3637–3639(1968) and 3 g formamide in 10 mL of anhydrous DMF heated to 100° C., a solution of sodium methoxide, from 0.33 g of sodium dissolved in methanol, was added dropwise over 20 minutes. After stirring for 1h at 100° C., the mixture was allowed to cool to room temperature and added to 100 mL of isopropanol. The mixture was concentrated to dryness. The residue was triturated with 200 mL of chloroform, filtered and concentrated to dryness under reduced pressure. The resulting oil was fairly homogeneous by TLC (development with 90:10 chloroform saturated with ammonia: methanol):

$^1$H NMR (400 MHz, CDCl$_3$): δ 7.1 (5H), 4.3 (br s, 2 H), 3.5 (d, 2H), 3.4 (m, 1H), 2.6 (m, 2H), 2.5 (m, 1H), 2.25 (m, 1H), 1.9 (m, 1H).

Step 2:
3-Carbamoyl-pyrrolidine-1-carboxylic acid benzyl ester

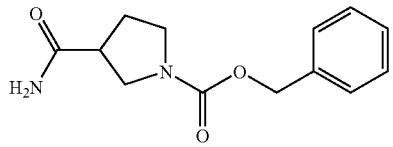

A mixture of 4.5 g 1-benzyl-pyrrolidine-3-carboxylic acid amide, 200 mL THF, 20 mL methanol and 1 g 20% palladium hydroxide on carbon was shaken under 50 psi of hydrogen for 12 h. The catalyst was filtered off and the filtrate concentrated under reduced pressure. Drying under vacuum gave 3 g of an oil. To a stirred solution of the crude residue in 500 mL of chloroform was added 5.5 g of N-(benzyloxycarbonyloxy)succinimide and 2.2 mL of triethylamine. The mixture was allowed to stir overnight then washed with 50 mL of saturated sodium carbonate, dried over magnesium sulfate, and concentrated to dryness. Purification by chromatography on silica gel, eluting with 90:10 ethyl acetate: methanol, gave 3-carbamoyl-pyrrolidine-1-carboxylic acid benzyl ester:

$^1$H NMR (400 MHz, CDCl$_3$): δ 7.35 (m, 5H), 5.6 (br m, 2H), 3.6 (m, 3H), 3.4 (m, 1H), 2.9 (br m, 1H), 2.1 (m, 2H).

Step 3:
3-Aminomethyl-pyrrolidine-1-carboxylic acid benzyl ester

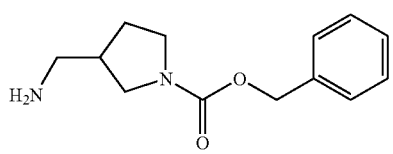

A mixture of 1 g 3-carbamoyl-pyrrolidine-1-carboxylic acid benzyl ester and 24 mL 1M borane-THF was stirred at room temperature for 24 h, then carefully quenched with 50 mL of 3N HCl. The mixture was concentrated under reduced pressure, then partitioned between 50 mL chloroform and 25 mL saturated aqueous sodium carbonate. Concentration of the combined extracts after drying over magnesium sulfate gave 3-aminomethyl-pyrrolidine-1-carboxylic acid benzyl ester:

$^1$H NMR (400 MHz, CDCl$_3$ ): δ 7.35 (m, 5H), 5.15 (s, 2H), 3.7–4 (complex, 4H), 2.7 (m, 1H), 2.4–2.0 (complex, 2H), 1.6 (m, 4H).

Step 4:
3-(Pyrimidin-2-ylaminomethyl)-pyrrolidine-1-carboxylic acid benzyl ester

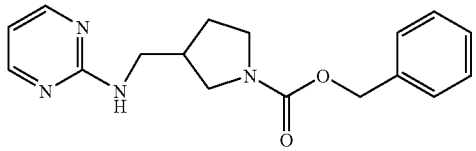

A mixture of 3-aminomethyl-pyrrolidine-1-carboxylic acid benzyl ester (0.15 g), 2-bromopyrimidine (0.25 g), 2-propanol (10 mL), and of N,N-diisopropylethylamine (0.1 mL) was heated to reflux overnight. Purification of the residue obtained after concentration under reduced pressure by preparative chromatography, and eluting with ethyl acetate, gave 3-(pyrimidin-2-ylaminomethyl)-pyrrolidine-1-carboxylic acid benzyl ester as a solid:

$^1$H NMR (400 MHz, CDCl$_3$) ): δ 8.15 (d, 2H), 7.3 (m, 5H), 6.5 (dd, 1H), 5.8 (m, 1H), 5.1 (s 2H), 3.s (m, 2H), 3.4 (m, 3H), 3.2 (m, 1H), 2.55 (m, 1H), 2.0 (m, 1H), 1.7 (m, 1H) MS (m+1)=313.

Example 80

(R,S) 4-[1-(Pyridin-4-ylamino)-ethyl]-piperidine-1-carboxylic acid benzyl ester

Step 1:
4-Acetyl-piperidine-1-carboxylic acid benzyl ester

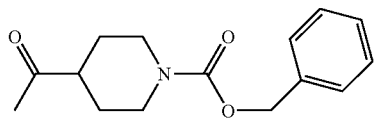

To a solution of 5 g of 4-(N-methoxy-N-methyl-carbamoyl)-piperidine-1-carboxylic acid benzyl ester (S. Nahm and S. W. Weinreb, *Tetrahedron Letters*, 22:3815–3818(1981)) in 50 mL of anhydrous THF cooled to 0° C., was added dropwise 6 mL of 3M methylmagnesium bromide in ether over 10 minutes. After stirring for 1 h at 0° C., the resulting mixture was quenched with 50 mL of 1N HCl and extracted with 3×50 mL of ether. The combined extracts were dried over magnesium sulfate and concentrated to dryness under reduced pressure. Drying under vacuum gave 4-Acetyl-piperidine-1-carboxylic acid benzyl ester as a white solid:

$^1$H NMR (400 MHz, CDCl$_3$): δ 7.35 (m, 5H), 5.15 (s, 2H), 4.2 (br s, 2H), 2.9 (br t, 2H), 2.5 (m, 1H), 2.2 (s, 3H), 1.9 (m, 2H), 1.6 (m, 21).

Step 2:
4-(1-Hydroxyimino-ethyl)-piperidine-1-carboxylic acid benzyl ester

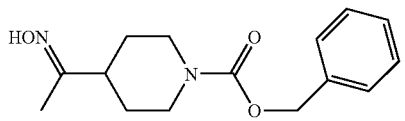

A mixture of 4.0 g of 4-acetyl-piperidine-1-carboxylic acid benzyl ester, 25 mL of pyridine, and 6 g of hydroxylamine hydrochloride were heated to 100° C. for 12 h. The mixture was concentrated under reduced pressure and partitioned between 200 mL of ethyl acetate and 50 mL of 1N HCl. The organic extract was dried over magnesium sulfate and concentrated to dryness under reduced pressure. Drying under vacuum gave 4-(1-hydroxyimino-ethyl)-piperidine-1-carboxylic acid benzyl ester as a solid:

$^1$H NMR (400 MHz, CDCl$_3$): δ 7.35 (m, 5H), 5.15 (s, 2H), 4.3 (br s, 2H), 2.8 (br t, 2H), 2.3 (m, 1H), 2.05 and 1.85 (2s, 3H), 1.8 (m, 2H), 1.5 (m, 2H).

Step 3:
4-(1-Hydroxyimino-ethyl)-piperidine-1-carboxylic acid tert-butyl ester

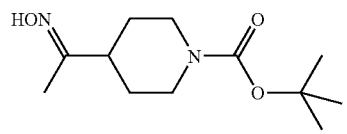

A mixture of 3.2 g of 4-(1-hydroxyimino-ethyl)-piperidine-1-carboxylic acid benzyl ester, 0.4 g of di-tert-butyl-dicarbonate, 0.15 g of 10% palladium on carbon and 20 mL of THF was stirred under an atmosphere of hydrogen for 2 h. The mixture was filtered and concentrated under reduced pressure. Drying under vacuum gave 4-(1-hydroxyimino-ethyl)-piperidine-1-carboxylic acid tert-butyl ester:

$^1$H NMR (400 MHz, CDCl$_3$): δ 4.15 (br s, 2H), 2.7 (br t, 2H), 2.25 (m, 1H), 1.8 (s, 3H), 1.7 (m, 2H), 1.42 (m, 2H), 1.4 (s, 9H).

Step 4:
(R,S) 4-(1-Amino-ethyl)-piperidine-1-carboxylic acid tert-butyl ester

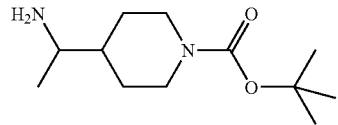

A mixture of 3 g of 4-(1-hydroxyimino-ethyl)-piperidine-1-carboxylic acid tert-butyl ester, 5 g of wet Raney-nickel and 100 mL of 5% ammonia in ethanol was shaken under 55 psi of hydrogen for 12 h. The mixture was filtered and concentrated under reduced pressure. The resulting crude product was taken up in 250 mL of chloroform, dried over magnesium sulfate, and concentrated under reduced pressure. Drying under vacuum gave (R,S) 4-(1-amino-ethyl)-piperidine-1-carboxylic acid tert-butyl ester:

$^1$H NMR (400 MHz, CDCl$_3$): δ 4.05 (br s, 2H), 2.6 (br m, 3H), 2.25 (m, 1H), 1.6 (dd, 2H), 1.4 (s, 9H), 1.2 (m, 2H), 1.1 (m, 2H), 1.0 (d, 3H).

Step 5:

(R,S) 4-[1-(Pyridin-4-ylamino)-ethyl]-piperidine-1-carboxylic acid tert-butyl ester

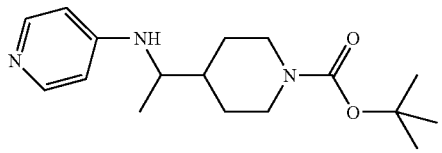

A mixture of 3 g of 4-(1-amino-ethyl)-piperidine-1-carboxylic acid tert-butyl ester, 2.5 g of 4-bromopyridine hydrochloride, 3.6 g of sodium tert-butoxide, 0.14 g of palladium acetate, 0.38 g of racemic BINAP and 50 mL of THF was heated to reflux for 12 h. The mixture was cooled, diluted with 50 mL of water and concentrated under reduced pressure. The resulting residue was partitioned between 500 mL of chloroform and 200 mL of water. The extracts were dried over magnesium sulfate and concentrated under reduced pressure. Purification by chromatography, eluting with 90:10 chloroform saturated with ammonia: methanol gave (R,S) 4-[1-(pyridin-4-ylamino)-ethyl]-piperidine-1-carboxylic acid tert-butyl ester resin:

$^1$H NMR (400 MHz, CDCl$_3$): δ 8.15 (d, 2H), 6.4 (d, 2H), 4.3 (d, 1H), 4.15 (br s, 2H), 3.2 (m, 1H), 2.65 (m, 2H), 2.5 (m, 1H), 1.7 (dd, 2H), 1.6 (m, 1H), 1.42 (s, 9H), 1.25 (m, 2H), 1.15 (m, 2H), 1.1 (d, 3H).

Step 6:

(R,S) 4-[1-(Pyridin-4-ylamino)-ethyl]-piperidine-1-carboxylic acid benzyl ester

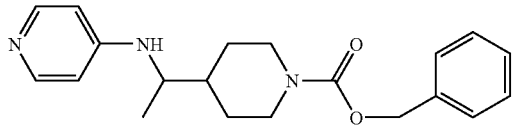

A mixture of 0.1 g of 4-[1-(pyridin-4-ylamino)-ethyl]-piperidine-1-carboxylic acid tert-butyl ester and 10 mL of 4N HCl in dioxane was stirred at room temperature for 2 h, then concentrated to dryness. The residue was diluted with 50 mL of chloroform and 1 mL of saturated sodium carbonate, cooled to 0° C. and treated with 0.05 mL of benzyl chloroformate. The resulting solution was allowed to stir for 3 h then separated. The organic layer was dried over magnesium sulfate and concentrated under reduced pressure. Purification by preparative chromatography eluting with 90:10 chloroform saturated with ammonia: methanol gave (R,S) 4-[1-(pyridin-4-ylamino)-ethyl]-piperidine-1-carboxylic acid benzyl ester:

$^1$H NMR (400 MHz, CDCl$_3$) δ 8.15 (d, 2H), 7.3 (m, 5H), 6.4 (d, 2H), 4.38 (d, 1H), 4.15 (br s, 2H), 3.4 (m, 1H), 2.9 (m, 1H), 2.75 (m, 2H), 1.65 (dd, 2H), 1.6 (m, 1H), 1.32 (m, 4H), 1.1 (d, 3H)

MS (m+1)=340.

The following EXAMPLES 81–103 were prepared from a primary amine described herein and a chloro-substituted heterocycle using conditions and procedures similar to those described in EXAMPLE 77, Step 6 unless otherwise stated:

Example 81

N2-[1-(2-Phenyl-ethanesulfonyl)-piperidin-4-ylmethyl]-quinazoline-2,4-diamine

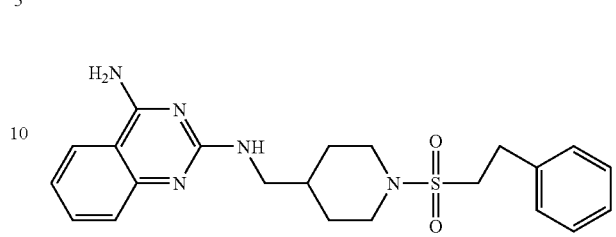

EXAMPLE 81 was prepared from C-[1-(2-phenyl-ethanesulfonyl)-piperidin-4-yl]-methylamine and 2-chloro-quinazolin-4-yl-amine (2-chloro-quinazolin-4-ylamine was prepared from 2,4-dichloroquinazoline and ammonia in THF at room temperature; N. B. Chapman, G. M. Gibson, F. G. Mann, *J. Chem. Soc.*, 1947, 890–899): MS (m+1)=426.

Example 82

[1-(2-Phenyl-ethanesulfonyl)-piperidin-4-ylmethyl]-(9H-purin-2-yl)amine

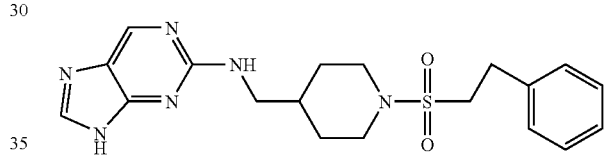

EXAMPLE 82 was prepared from C-[1-(2-phenyl-ethanesulfonyl)-piperidin-4-yl]-methylamine and 2-chloro-9H-purine (2-chloro-9H-purine was prepared according to S. R. Brashears, S. S. Wang, S. G. Bechtolt, B. E. Christensen, *J. Am. Chem. Soc.*, 81:3789–3792(1959)): MS (m+1)=401.

Example 83

2-{[1-(2-Phenyl-ethanesulfonyl)-piperidin-4-ylmethyl]-amino}-pyrimidine-4-carboxylic acid amide

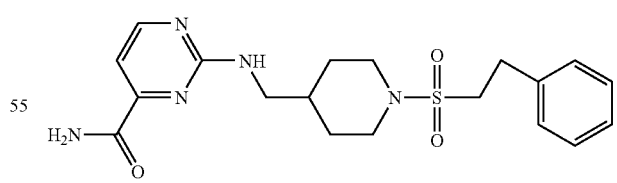

EXAMPLE 83 was prepared from C-[1-(2-phenyl-ethanesulfonyl)-piperidin-4-yl]-methylamine and 2-chloro-pyrimidine-4-carboxylic acid amide (2-chloro-pyrimidine-4-carboxylic acid amide was prepared according to G. D. Davies, D. E. O'Brien, L. R. Lewis, C. C. Cheng, *J. Heterocyclic Chem.*, 1:130–131(1964):

MS (m+1)=404.

Example 84

(9-Methyl-9H-purin-6-yl)-[1-(2-phenyl-ethanesulfonyl)-piperidin-4-ylmethyl]-amine

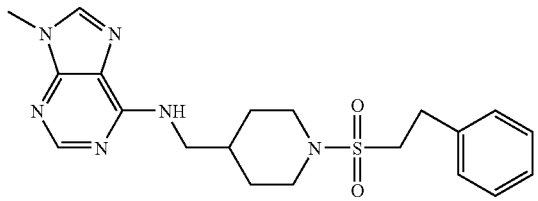

EXAMPLE 84 was prepared from C-[1-(2-phenyl-ethanesulfonyl)-piperidin-4-yl]-methylamine and 6-chloro-9-methyl-9H-purine (6-chloro-9-methyl-9H-purine prepared according to G. B. Eilon, *J. Org. Chem.*, 27:2478–2491(1962):

MS (m+1)=415.

Example 85

(7-Methyl-7H-purin-6-yl)-[1-(2-phenyl-ethanesulfonyl)-piperidin-4-ylmethyl]-amine

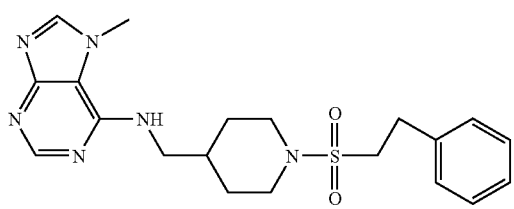

EXAMPLE 85 was prepared from C-[1-(2-phenyl-ethanesulfonyl)-piperidin-4-yl]-methylamine and 6-chloro-7-methyl-7H-purine (6-chloro-7-methyl-7H-purine was prepared according to G. B. Eilon, *J. Org. Chem.*, 27:2478–2491(1962): MS (m+1)=415.

Example 86

4-(Pteridin-4-ylaminomethyl)-piperidine-1-carboxylic acid benzyl ester

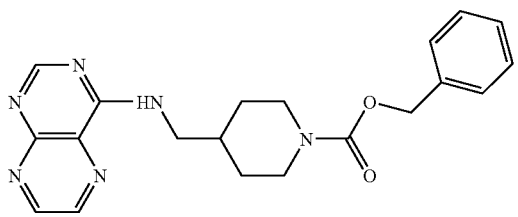

EXAMPLE 86 was prepared from 4-aminomethyl-piperidine-1-carboxylic acid benzyl ester and 4-methylthio-pteridine (4-methylthio-pteridine was prepared according to A. A. Brown, D. J. Brown,h. C. S. Wood, *J. Chem. Soc.*, 1954, 3832–3839): MS (m+1)=379.

Example 87

4-[(7H-Pyrrolo[2,3-d]pyrimidin-4-ylamino)-methyl]-piperidine-1-carboxylic acid benzyl ester

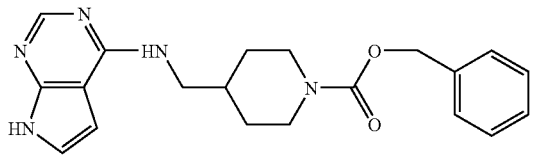

EXAMPLE 87 was prepared from 4-aminomethyl-piperidine-1-carboxylic acid benzyl ester and 4-chloro-7H-pyrrolo[2,3-d]pyrimidine (4-chloro-7H-pyrrolo[2,3-d]pyrimidine was prepared according to U. Lupke, F. Seela, *Chem. Ber.*, 112:3832–3839(1979): MS (m+1)=366.

Example 88

4-[(1H-Imidazo[4,5c]pyridin-4-ylamino)-methyl]-piperidine-1-carboxylic acid benzyl ester

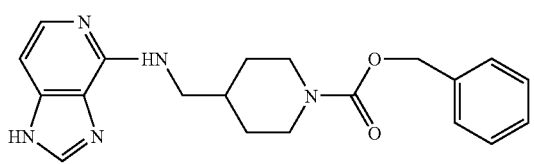

EXAMPLE 88 was prepared from 4-aminomethyl-piperidine-1-carboxylic acid benzyl ester and 7-chloro-3H-imidazo[4,5-b]pyridine (7-chloro-3H-imidazo[4,5-b]pyridine was prepared according to Y. Mizuno, T. Itoh, K. Saito, *Chem. Pharm. Bull.*, 12:866–872(1964): MS (m+1)=366.

Example 89

(3-Chloro-pyrazin-2-yl)-[1-(2-phenyl-ethanesulfonyl)-piperidin-4-ylmethyl]-amine

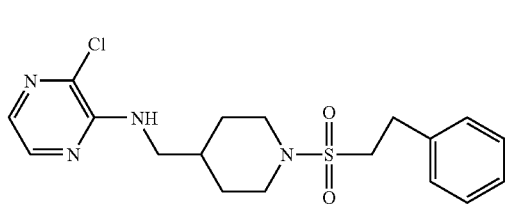

EXAMPLE 89 was prepared from C-[1-(2-phenyl-ethanesulfonyl)-piperidin-4-yl]-methylamine and 2,3-dichloropyrazine (refluxing 2-butanol):

MS (m+1)=396.

Example 90

[1-(2-Phenyl-ethanesulfonyl)-piperidin-4-ylmethyl]-pyrazin-2-yl-amine

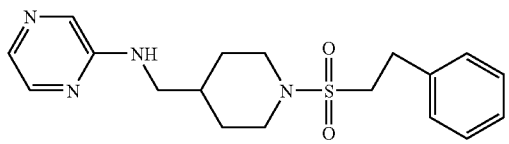

EXAMPLE 90 was prepared from (3-chloro-pyrazin-2-yl)-[1-(2-phenyl-ethanesulfonyl)-piperidin-4-ylmethyl]-amine by hydrogenation in ethanol-triethylamine over 5% palladium on carbon, 1 atm of hydrogen: MS (m+1)=361.

Example 91

(2-Chloro-5-methyl-pyrimidin-4-yl)-[1-(2-phenyl-ethanesulfonyl)-piperidin-4-ylmethyl]-amine

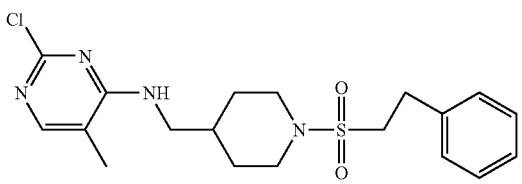

EXAMPLE 91 was prepared from C-[1-(2-phenyl-ethanesulfonyl)-piperidin-4-yl]-methylamine and 2,4-dichloro-5-methyl-pyrimidine: MS (m+1)=410.

Example 92

(5-Methyl-pyrimidin-4-yl)-[1-(2-phenyl-ethanesulfonyl)-piperidin-4-ylmethyl]-amine

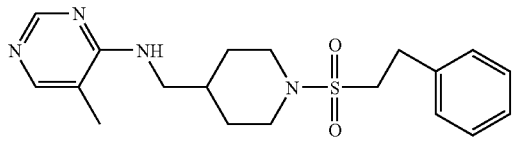

EXAMPLE 92 was prepared from (2-chloro-5-methyl-pyrimidin-4-yl)-[1-(2-phenyl-ethanesulfonyl)-piperidin-4-ylmethyl]-amine by hydrogenation in ethanol-triethylamine over 5% palladium on carbon, 1 atm of hydrogen: MS (m+1)=375.5.

Example 93

[1-(2-Phenyl-ethanesulfonyl)-piperidin-4-ylmethyl]-pyrimidin-4-yl-amine

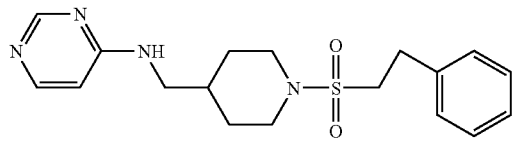

EXAMPLE 93 was prepared from C-[1-(2-phenyl-ethanesulfonyl)-piperidin-4-yl]-methylamine and 2,4-dichloro-pyrimidine followed by hydrogenation in ethanol-triethylamine over 5% palladium on carbon, 1 atm of hydrogen: MS (m+1)=361.5.

Example 94

(4-Methyl-pyrimidin-2-yl)-[1-(2-phenyl-ethanesulfonyl)-piperidin-4-ylmethyl]-amine

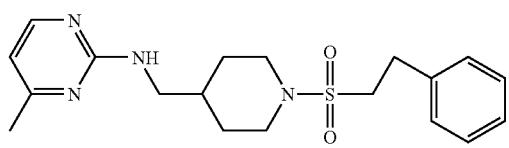

EXAMPLE 94 was prepared from C-[1-(2-phenyl-ethanesulfonyl)-piperidin-4-yl]-methylamine and 2-chloro-4-methyl-pyrimidine: MS (m+1)=375.5.

Example 95

5-Fluoro-N2-[1-(2-phenyl-ethanesulfonyl)-piperidin-4-ylmethyl]-pyrimidine-2,4-diamine

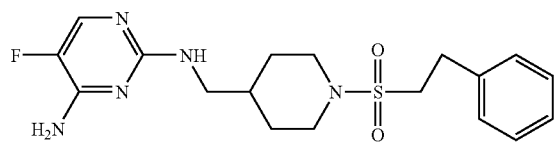

EXAMPLE 95 was prepared from C-[1-(2-phenyl-ethanesulfonyl)-piperidin-4-yl]-methylamine and 2-chloro-5-fluoro-pyrimidin-4-ylamine: MS (m+1)=394.5.

Example 96

N2-[1-(2-Phenyl-ethanesulfonyl)-piperidin-4-ylmethyl]-pyrimidine-2,4-diamine

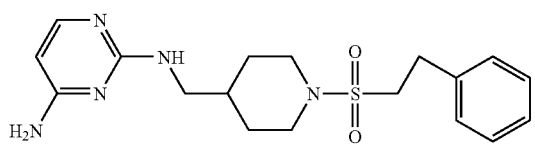

EXAMPLE 96 was prepared from C-[1-(2-phenyl-ethanesulfonyl)-piperidin-4-yl]-methylamine and 2-chloro-pyrimidin-4-ylamine (prepared from 2,4-chloro-pyrimidin-4-ylamine by hydrogenation in ethanol over 5% palladium on carbon, 1 atm of hydrogen): MS (m+1)=376.5.

Example 97

(3-Methyl-pyrazin-2-yl)-[1-(2-phenyl-ethanesulfonyl)-piperidin-4-ylmethyl]-amine

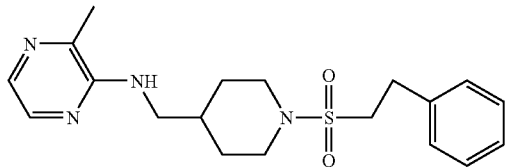

EXAMPLE 97 was prepared from C-[1-(2-phenyl-ethanesulfonyl)-piperidin-4-yl]-methylamine and 3-bromo-pyrazin-2-carboxylic acid methyl ester followed by reduction with lithium tri-sec-butylborohydride at 0° C. in THF: MS (m+1)=375.5.

Example 98

{1-[2-(2-Fluoro-phenyl)-ethanesulfonyl]-piperidin-4-ylmethyl}-pyrimidin-2-yl-amine

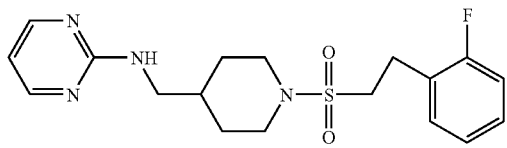

EXAMPLE 98 was prepared from 2-(2-fluoro-phenyl)-ethanol as described in EXAMPLE 78, Steps 1–7 above: MS (m+1)=378.5.

Example 99

{1-[2-(4-Chloro-phenyl)-ethanesulfonyl]-piperidin-4-ylmethyl}-pyrimidin-2-yl-amine

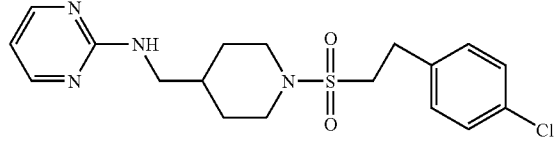

EXAMPLE 99 was prepared from 2-(4-chloro-phenyl)-ethanol as described in EXAMPLE 78, Steps 1–7 above: MS (m+1)=396.

Example 100

Pyrimidin-2-yl-[1-(2-p-tolyl-ethanesulfonyl)-piperidin-4-ylmethyl]-amine

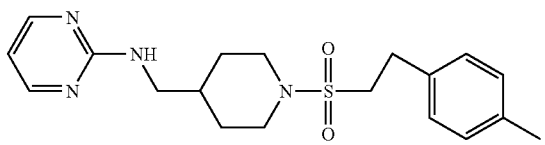

EXAMPLE 100 was prepared from 2-(4-methyl-phenyl)-ethanol as described in EXAMPLE 78, Steps 1–7 above: MS (m+1)=375.5.

Example 101

3-(Pteridin-4-ylaminomethyl)-pyrrolidine-1-carboxylic acid benzyl ester

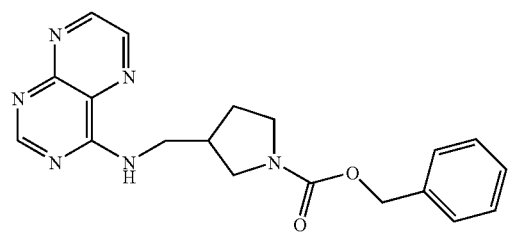

EXAMPLE 101 was prepared from 3-aminomethyl-pyrrolidine-1-carboxylic acid benzyl ester (EXAMPLE 79, Step 3) and 4-methylthio-pteridine (A. A. Brown, D. J. Brown,h. C. S. Wood, J. Chem. Soc., 1954, 3832–3839): MS (m+1)=365.4.

Example 102

3-[(9H-Purin-6-ylamino)-methyl]-pyrrolidine-1-carboxylic acid benzyl ester

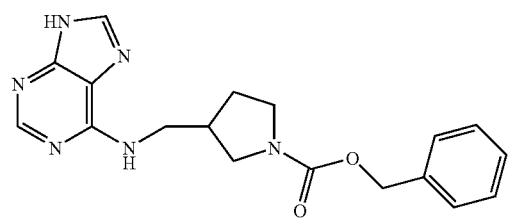

EXAMPLE 102 was prepared from 3-aminomethyl-pyrrolidine-1-carboxylic acid benzyl ester (EXAMPLE 79, Step 3) and 6-chloro-9H-purine:

MS (m+1)=353.4.

Example 103

3-Nitro-$N^6$-[1-(2-phenyl-ethanesulfonyl)-piperidin-4-ylmethyl]-pyridine-2,6-diamine

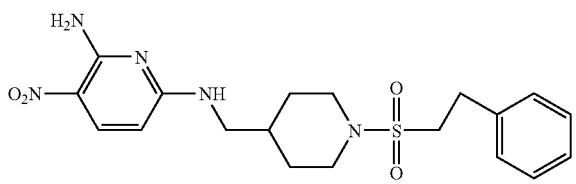

EXAMPLE 103 was prepared from C-[1-(2-phenyl-ethanesulfonyl)-piperidin-4-yl]-methylamine and 6-chloro-3-nitro-pyridin-2-ylamine: MS (m+1)=420.5.

Example 104

(1H-Imidazo[4,5-b]pyridin-5-yl)-[1-(2-phenyl-ethanesulfonyl)-piperidin-4-ylmethyl]-amine

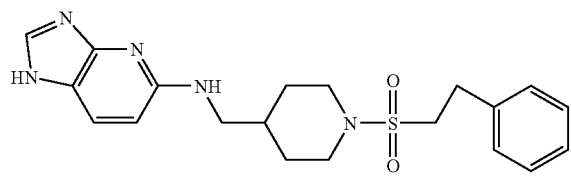

EXAMPLE 104 was prepared from 3-nitro-$N^6$-[1-(2-phenyl-ethanesulfonyl)-piperidin-4-ylmethyl]-pyridine-2,6-diamine (EXAMPLE 103) (1 mmol scale) by hydrogenation in 15 mL of THF/methanol over 0.5 of Raney-nickel under 1 atm of hydrogen for 1 h, followed by immediate conversion of the crude, air sensitive triaminopyridine into the imidazo[4,5b]pyridine by heating with 5 mL of 96% formic acid and 2 mL of 37% hydrochloric acid at reflux overnight. The free base was liberated with sodium hydroxide and purified by preparative chromatography, eluting with 90:10 chloroform: methanol: MS (m+1)=400.5.

Example 105

4-[(1H-Benzoimidazol-4-ylamino)-methyl]-piperidine-1-carboxylic acid benzyl ester

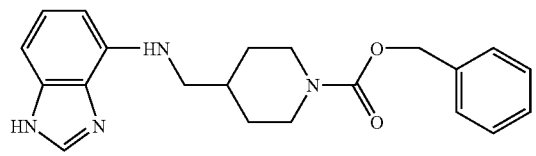

EXAMPLE 105 was prepared from 1H-benzoimidazol-4-ylamine (The 1H-benzoimidazol-4-yl-amine was prepared by heating 1.5 g of 3-nitro-benzene-1,2-diamine in 50 mL of triethyl orthoformate with 10 mg of p-toluenesulfonic acid monohydrate at reflux overnight, concentration to dryness under reduced pressure, hydrolysis with refluxing 3N HCl for 1 h and neutralization with NaOH. Then, cooling and collection yielded the 4-nitro-benzimidazole product by filtration. Catalytic reduction using Raney Nickel® in ethanol under 1 atm of hydrogen for 1 h gave 1H-benzoimidazol-4-ylamine as an air sensitive solid) and 4-formyl-piperidine-1-carboxylic acid benzyl ester (prepared from 4-(N-methoxy-N-methyl-carbamoyl)-piperidine-1-carboxylic acid benzyl ester, using the procedures described by S. Nahm and S. W. Weinreb, *Tetrahedron Letters*, 22:3815–3818(1981)) on a 1 mmol scale by reductive amination in 5 mL of 1,2-dichloromethane using sodium triacetoxyborohydride over 0.5 of Raney Nickel® under 1 atm of hydrogen for 1 h, followed by immediate conversion of the crude, air sensitive triaminopyridine into the imidazo[4,5b]pyridine by heating with 5 mL of 96% formic acid and 2 mL of 37% hydrochloric acid at reflux overnight. The free base was liberated with sodium hydroxide and purified by preparative chromatography, eluting with 90:10 chloroform: methanol: MS (m+1)=365.5.

Example 106

4-[(3-Hydroxy-pyridin-4-ylamino)-methyl]-piperidine-1-carboxylic acid benzyl ester

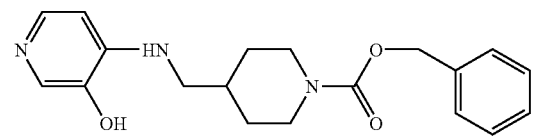

EXAMPLE 106 was prepared from 4-(3-hydroxy-pyridin-4-ylcarbamoyl)-piperidine-1-carboxylic acid benzyl ester (which was prepared by EDC coupling of 4-aminopyridin-3-ol and N-benzyloxycarbonyl piperidine-4-carboxylic acid) by borane-THF reduction overnight at room temperature. The reaction was quenched by slow addition of 1N HCl until pH=2, then basified to pH=10 with 10N NaOH. Extraction with chloroform yielded a crude product which was purified by preparative chromatography, eluting with 90:10 chloroform saturated with ammonia: methanol to give 4-[(3-hydroxy-pyridin-4-ylamino)-methyl]-piperidine-1-carboxylic acid benzyl ester: MS (m+1)=342.4.

Example 107

3-exo-(Pyridin-4-ylaminomethyl)-8-aza-bicyclo[3.2.1]octane-8-carboxylic acid benzyl ester hydrochloride Step 1:

(8-Benzyl-8-azabicyclo[3.2.1]oct-3-exo-yl)methylamine

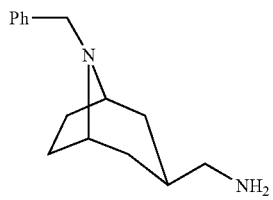

In a three-neck flask equipped with an addition funnel, a nitrogen inlet, and a rubber septum was placed a 1M solution of lithium aluminum hydride in tetrahydrofuran (5.5 mL, 5.5 mmol). To that solution, a solution of 8-benzyl-8-azabicyclo[3.2.1]octane-3-exo-carbonitrile (EP 31219 A1 19810701) (1.13 g, 5.0 mmol) in dry tetrahydrofuran was added dropwise via syringe. The resulting mixture was stirred 3 hours at 60° C. The mixture was cooled in an ice-bath and 3N sodium hydroxide solution (25 mL) was added dropwise. The mixture was extracted with ethyl acetate (2×100 mL). The combined extract was washed with water (50 mL) and brine (50 mL), dried (sodium sulfate), filtered, and the solvent was evaporated under reduced pressure to give crude (8-benzyl-8-azabicyclo[3.2.1]oct-3-exo-yl)methylamine product as an oil.

$^1$H NMR (CDCl$_3$) δ 7.38 (2H, d, J 7 Hz), 7.34–7.23 (3H, m), 3.54 (2H, s), 3.21 (2H, m), 2.55 (2H, d, J 6.5 Hz), 2.01 (2H, m), 1.67 (1H, m), 1.60 (2H, d, J 8 Hz), 1.56–1.34 (6H, m).

Mass spec.: 231.50 (M+1).

Step 2:

(8-Benzyl-8-aza-bicyclo[3.2.1]oct-3-exo-ylmethyl)pyridin-4-yl-amine

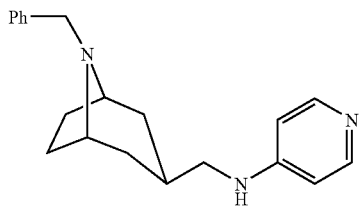

To a mixture of (8-benzyl-8-azabicyclo[3.2.1]oct-3-exo-yl)methylamine (0.999 g, 4.3 mmol), 4-bromopyridine hydrochloride (0.719 g, 3.7 mmol), palladium acetate (0.033 g, 0.15 mmol), and (±)-BINAP (0.092 g, 0.15 mmol) in tetrahydrofuran (34 mL) under nitrogen, was added sodium t-butoxide (0.86 g, 8.9 mmol). The mixture was stirred at 70° C. under nitrogen for 18 h. The mixture was diluted with ether (35 mL), washed with brine (2×35 mL), dried (sodium sulfate), filtered, and the solvent was evaporated under reduced pressure to give crude product (1.42 g) as a brown gum. The crude product was flash chromatographed on silica gel, eluting first with methanol: methylene chloride (10:90) to remove impurities, then with methanol: methylene chloride: ammonium hydroxide (10:90:1 increasing to 20:80:2) to give a yellow foam (1.08 g). The foam was triturated with ether to give a crystalline solid. The solid was filtered off and dried in vacuo to give (8-benzyl-8-aza-bicyclo[3.2.1]oct-3-exo-ylmethyl)pyridin-4-yl-amine product as a yellow solid.

$^1$H NMR (CDCl$_3$) δ 8.16 (2H, m), 7.39 (2H, d, J 1.5 Hz), 7.32 (2H, m), 7.26 (1H, m), 6.41 (2H, m), 4.25 (1H, br s), 3.55 (2H, s), 3.25 (2H, m), 3.02 (2H, t, J 6 Hz), 2.05 (2H, m), 1.97 (1H, m), 1.55 (6H, m).

Mass spec.: 308.36 (M+1).

Step 3:

(8-Benzyl-8-aza-bicyclo[3.2.1]oct-3-exo-ylmethyl)pyridin-4-yl-carbamic acid tert-butyl ester

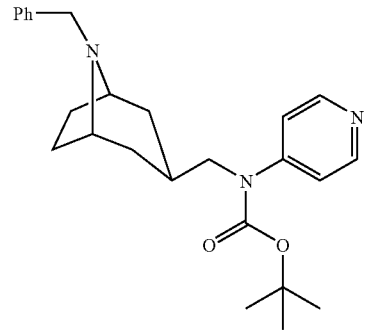

A mixture of (8-benzyl-8-aza-bicyclo[3.2.1]oct-3-exo-ylmethyl)pyridin-4-yl-amine (0.707 g, 2.3 mmol), 4-dimethylaminopyridine (0.037 g, 0.30 mmol, 0.13 equiv.), and di-tert-butyl dicarbonate (0.79 g, 3.6 mmol) in acetonitrile was stirred under nitrogen at ambient temperature for 18 h. The mixture was concentrated under reduced pressure and the residue was taken up in methylene chloride (60 mL). The mixture was washed with saturated sodium bicarbonate solution (30 mL), water (30 mL), and brine (30 mL), dried (sodium sulfate), filtered, and the solvent was evaporated under reduced pressure to give a crude product (0.96 g) as an orange gum. The crude product was flash chromatographed on silica gel eluting, first with methanol: methylene chloride (10:90), then with methanol: methylene chloride: ammonium hydroxide (10:90:1) to give (8-benzyl-8-aza-bicyclo[3.2.1]oct-3exo-ylmethyl)pyridin-4-yl-carbamic acid tert-butyl ester product as a yellow oil.

$^1$H NMR (CDCl$_3$) δ 8.52 (2H, m), 7.40–7.23 (5H, m), 7.19 (2H, m), 3.60 (2H, d, J7 Hz), 3.51 (2H, m), 3.18 (2H, br s), 1.99 (3H, m), 1.48 (9H, s), 1.42 (6H, m).

Step 4:

(8-Aza-bicyclo[3.2.1]oct-3-exo-ylmethyl)pyridin-4-yl-carbamic acid tert-butyl ester

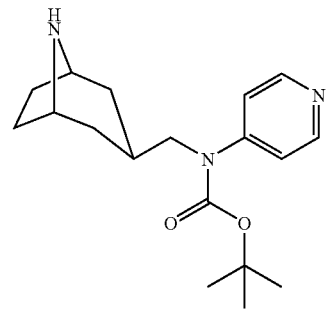

A mixture of (8-benzyl-8-aza-bicyclo[3.2.1]oct-3-exo-ylmethyl)pyridin-4-yl-carbamic acid tert-butyl ester (0.917 g, 2.25 mmol) and 10% palladium on carbon (0.60 g) in methanol (25 mL) was hydrogenated (53 psi hydrogen) for 18 h. The catalyst was removed by filtration through Celite. The filter cake was washed with methanol (3×25 mL) and the filtrate was concentrated under reduced pressure to give crude product (0.592 g)as a gum. The crude product was flash chromatographed on silica gel eluting with methanol: methylene chloride: ammonium hydroxide (10:90:1 increasing to 20:80:2) to give product as a solid white foam.

¹H NMR (CDCl₃) δ 8.53 (2H, m), 7.19 (2H, m), 3.80 (2H, s), 3.64 (2H, d, J 7 Hz), 2.6–2.0 (1H, br s), 2.10 (1H, m), 2.07 (2H, m), 1.63 (6H, m), 1.48 (9H, s).

Step 5:

3-exo-[(tert-Butoxycarbonyl-pyridin-4-yl-amino) methyl]-8-aza-bicyclo[3.2.1]octane-8-carboxylic acid benzyl ester

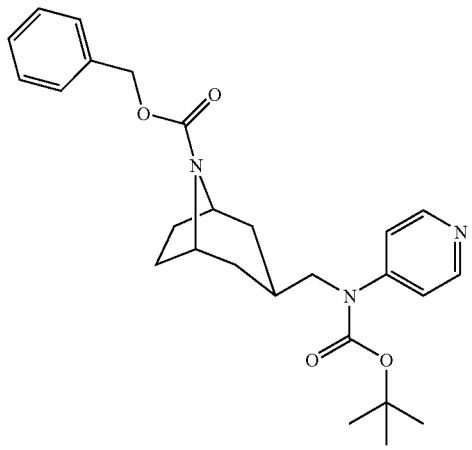

To a rapidly stirred mixture of (8-aza-bicyclo[3.2.1]oct-3-exo-ylmethyl)pyridin-4-yl-carbamic acid tert-butyl ester (95 mg, 0.30 mmol), sodium bicarbonate (76 mg, 0.90 mmol), methylene chloride (0.8 mL), and water (0.8 mL) cooled in an ice-bath, was added benzyl chloroformate (57 μL, 68 mg, 0.40 mmol). The mixture was stirred 18 h while warming from ice-bath to ambient temperature. The mixture was diluted with dichloromethane (5 mL) and the layers were separated. The organic layer was washed with water (2 mL), and brine (2 mL), dried (sodium sulfate), filtered, and the solvent was evaporated under reduced pressure to give a crude product (112 mg) as a pale yellow oil. The crude product was chromatographed on a 2 mm silica gel prep plate eluting with ethyl acetate: hexane (3:2) to give 3-exo-[(tert-butoxycarbonyl-pyridin-4-yl-amino)methyl]-8-aza-bicyclo[3.2.1]octane-8-carboxylic acid benzyl ester product as a colorless gum.

¹H NMR (CDCl₃) δ 8.53 (2H, d, J 6 Hz), 7.34 (5H, m), 7.17 (2H, d, J 6 Hz), 5.12 (2H, s), 4.29 (2H, br s), 3.56 (2H, d, J 7 Hz), 2.17 (1H, m), 1.92 (2H, m), 1.55–1.31 (15H, m).

Step 6:

3-exo-(Pyridin-4-ylaminomethyl)-8-aza-bicyclo [3.2.1]octane-8-carboxylic acid benzyl ester hydrochloride

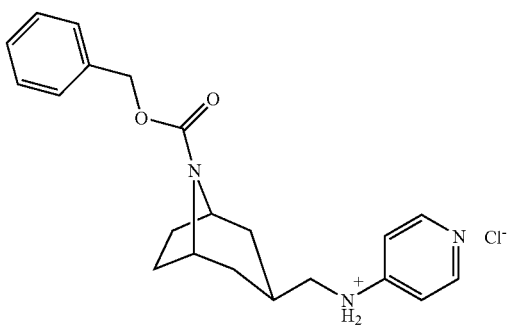

Into a solution of 3-exo-[(tert-butoxycarbonyl-pyridin-4-yl-amino)methyl]-8-aza-bicyclo[3.2.1]octane-8-carboxylic acid benzyl ester (54 mg, 0.12 mmol) in ethyl acetate (1 mL), cooled in an ice-bath, was bubbled hydrogen chloride for 2 minutes. The solution was stirred one hour with ice-bath cooling, de-gassed with nitrogen, then concentrated under reduced pressure. The residual gum was dissolved in methylene chloride (0.5 mL) and the solution was diluted with ether (5 mL) to deposit a gum. The supernatant was decanted, the gum was triturated with ether, and the resulting solid was filtered off and dried in vacuo to give 3-exo-(pyridin-4-ylaminomethyl)-8-aza-bicyclo[3.2.1]octane-8-carboxylic acid benzyl ester hydrochloride as an off-white solid.

¹H NMR (DMSO-d₆) δ 13.34 (1H, br s), 8.68 (1H, m), 8.19 (1H, br s), 8.06 (1H, br s), 7.36 (5H, m), 6.90 (2H, d, J 7 Hz), 5.08 (2H, s), 4.20 (2H, br s),3.11 (2H, t, J 6 Hz), 2.17 (1H, m), 1.88 (2H, m), 1.65 (4H, m), 1.31 (2H, m).

Mass spec.: 352.41 (M+1).

Example 108

3-exo-[(9H-Purin-6-ylamino)-methyl]-8-aza-bicyclo [3.2.1]octane-8-carboxylic acid benzyl ester Step 1:
(8-Benzyl-8-aza-bicyclo[3.2.1]oct-3-exo-ylmethyl)carbamic acid tert-butyl ester

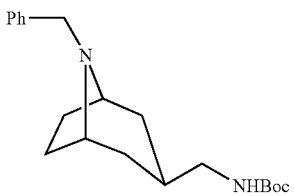

To a solution of (8-benzyl-8-azabicyclo[3.2.1]oct-3-exo-yl)methylamine (EXAMPLE 107, Step 1) (0.65 g, 2.8 mmol) in dichloromethane (30 mL) was added di-tert-butyl dicarbonate (0.65 mL, 0.69 g, 3.0 mmol). The solution was stirred 18 h under nitrogen. The solution was diluted with dichloromethane (50 mL), washed with saturated sodium bicarbonate solution (25 mL), water (25 mL), and brine (25 mL), dried (sodium sulfate), filtered, and the solvent was evaporated under reduced pressure to give a crude product (0.993 g) as a pale yellow solid. A solution of the crude product in ethyl acetate (5 mL) was filtered through a pad of silica gel, eluting with ethyl acetate: hexane (2:1). The filtrate was evaporated under reduced pressure to give (8-benzyl-8-aza-bicyclo[3.2.1]oct-3-exo-ylmethyl)carbamic acid tert-butyl ester product as a white solid.

$^1$H NMR (CDCl$_3$) δ 7.37 (2H, d, J 7 Hz), 7.30 (2H, t, J 7 Hz), 7.24 (1H, m), 4.55 (1H, br s), 3.53 (2H, s), 3.19 (2H, s), 2.99 (2H, m), 2.00 (2H, m), 1.80 (1H, m), 1.55 (4H, m), 1.44 (11H, m).

Step 2:

(8-Aza-bicyclo[3.2.1]oct-3-exo-ylmethyl)carbamic acid tert-butyl ester

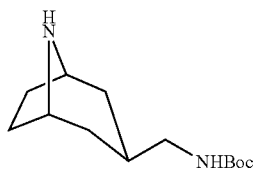

A mixture of tert-butyl (8-benzyl-8-azabicyclo[3.2.1]oct-3-exo-yl)methylcarbamate (0.892 g, 2.7 mmol) and 10% palladium on carbon (0.55 g) in methanol (50 mL) was hydrogenated under a hydrogen balloon for 18 h. The catalyst was removed by filtration through Celite. The filter cake was washed with methanol (3×25 mL) and the filtrate was concentrated under reduced pressure to give crude (8-aza-bicyclo[3.2.1]oct-3-exo-ylmethyl)carbamic acid tert-butyl ester product as a white solid.

$^1$H NMR (CDCl$_3$) δ 4.57 (1H, br s), 3.53 (2H, s), 2.96 (2H, m), 1.95–1.77 (4H, m), 1.72–1.50 (4H, m), 1.44 (9H, m), 1.24 (2H, m).

Mass spec.: 241.32 (M+1).

Step 3:

3-exo-(tert-Butoxycarbonylamino-methyl)-8-aza-bicyclo[3.2.1]octane-8-carboxylic acid benzyl ester

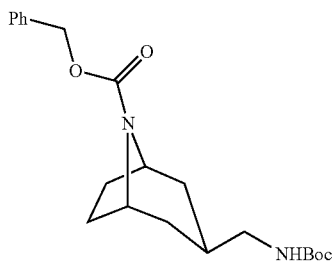

To a mixture of tert-butyl 8-azabicyclo[3.2.1]oct-3-exo-ylmethylcarbamate (0.84 g, 3.5 mmol) in acetonitrile (35 mL) was added 1-{[(benzyloxy)carbonyl]oxy}pyrrolidine-2,5-dione (0.87 g, 3.5 mmol). The mixture was stirred 18 h under nitrogen. The resulting solution was concentrated under reduced pressure. The residue was partitioned between ethyl acetate (150 mL) and water (75 mL) and the layers were separated. The organic layer was washed with water (2×75 mL) and brine (50 mL), dried (sodium sulfate), filtered, and the solvent was evaporated under reduced pressure to give a crude product (1.31 g) as a white solid. The crude product was purified by flash column chromatography on silica gel, eluting with ethyl acetate: hexane (30:70 increasing to 50:50) to give 3-exo-(tert-butoxycarbonylamino-methyl)-8-aza-bicyclo[3.2.1]octane-8-carboxylic acid benzyl ester product as a white solid.

$^1$H NMR (CDCl$_3$) δ 7.36 (5H, m), 5.13 (2H, s), 4.56 (1H, br s), 4.32 (2H, br s), 2.94 (2H, m), 2.00 (3H, m), 1.62 (4H, m), 1.48–1.25 (11H, m).

Mass spec.: 375.39 (M+1).

Step 4:

3-exo-Aminomethyl-8-aza-bicyclo[3.2.1]octane-8-carboxylic acid benzyl ester

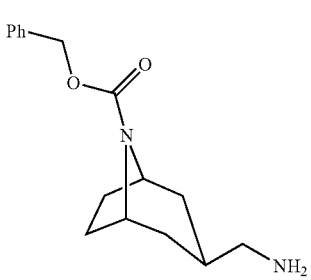

Benzyl 3-exo-{[(tert-butoxycarbonyl)amino]methyl}-8-azabicyclo[3.2.1]octane-8-carboxylate (0.94 g, 2.5 mmol) was placed in a round-bottom flask under nitrogen and cooled in an ice-bath. Trifluoroacetic acid (6 mL) was added dropwise and the mixture was stirred one hour with ice-bath cooling. The mixture was poured into ice-cold 5N sodium hydroxide solution (16 mL) and the aqueous mixture was extracted with methylene chloride (4×50 mL). The extract was washed with brine (50 mL), dried (sodium sulfate), filtered, and the solvent was evaporated under reduced pressure to give product as a colorless oil.

$^1$H NMR (CDCl$_3$) δ 7.36 (5H, m), 5.14 (2H, s), 4.33 (2H, br s), 2.52 (2H, d, J 6 Hz), 1.96 (2H, m), 1.88 (1H, m), 1.67 (2H, d, J 7 Hz), 1.61 (2H, m), 1.42–1.25 (4H, m).

Mass spec.: 275.34 (M+1).

Step 5:

3-exo-[(9H-Purin-6-ylamino)-methyl]-8-aza-bicyclo[3.2.1]octane-8-carboxylic acid benzyl ester

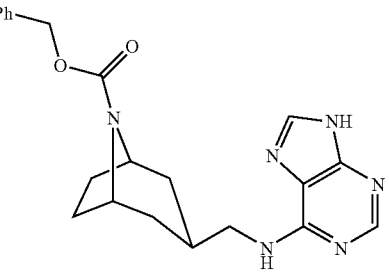

A solution of 3-exo-aminomethyl-8-aza-bicyclo[3.2.1]octane-8-carboxylic acid benzyl ester (27 mg, 0.10 mmol), 6-chloropurine (31 mg, 0.20 mmol), and diisopropylethylamine (35 μL, 0.20 mmol) in isopropanol (2 mL) was heated at reflux for 18 h. The resulting mixture was concentrated under reduced pressure and the residue was taken up in ethyl acetate (3 mL). The resulting mixture was washed with saturated sodium bicarbonate solution (1 mL), water (2×1 mL), and brine (1 mL), dried (sodium sulfate), filtered, and the solvent was evaporated under reduced pressure to give a crude product (39 mg) as a yellow solid. The solid was triturated in hot ethyl acetate (1 mL), the mixture cooled to ambient temperature, and the solid precipitate filtered off and dried in vacuo to give 3-exo-[(9H-purin-6-ylamino)-methyl]-8-aza-bicyclo[3.2.1]octane-8-carboxylic acid benzyl ester product as a white solid.

$^1$H NMR (DMSO-d$_6$) δ 12.86 (1H, br s), 8.16 (1H, s), 8.07 (1H, s), 7.61 (1H, br s), 7.35 (5H, m), 5.08 (2H, d, J 2 Hz), 4.17 (2H, br s), 3.32 (2H, m), 2.26 (1H, m), 1.86 (2H, br s), 1.61 (4H, m), 1.34 (2H, m).

Mass spec.: 393.36 (M+1).

Example 109

3-exo-[(3-Chloropyrazin-2-ylamino)methyl]-8-aza-bicyclo[3.2.1]octane-8-carboxylic acid benzyl ester

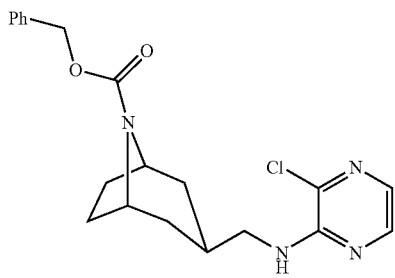

Employing the procedure substantially as described for 3-exo-[(9H-purin-6-ylamino)-methyl]-8-aza-bicyclo[3.2.1]octane-8-carboxylic acid benzyl ester (EXAMPLE 108), but substituting 2,3-dichloropyrazine for 6-chloropurine, the crude product (51 mg) was obtained as an oil. The crude product was filtered through a pad of silica gel eluting with ethyl acetate:hexane (2:1), and the filtrate was concentrated under reduced pressure. The residual oil was dissolved in ether, the solvent evaporated under reduced pressure, and the residue dried in vacuo to give 3-exo-[(3-chloropyrazin-2-ylamino)methyl]-8-aza-bicyclo[3.2.1]octane-8-carboxylic acid benzyl ester as a yellow gum.

$^1$H NMR (CDCl$_3$) δ 7.93 (1H, d, J 3 Hz), 7.56 (1H, d, J 3 Hz), 7.36 (5H, m), 5.20 (1H, m), 5.15 (2H, s), 4.34 (2H, br s), 3.32 (2H, m), 2.21 (1H, m), 1.97 (2H, m), 1.66 (4H, m), 1.60–1.40 (2H, m).

Mass spec.: 387.27 (M+1).

Example 110

[8-(2-Phenylethanesulfonyl)-8-aza-bicyclo[3.2.1]oct-3-exo-ylmethyl]pyrimidin-2-yl-amine Step 1:

[8-(2-trans-Phenylethenesulfonyl)-8-aza-bicyclo[3.2.1]oct-3-exo-ylmethyl]carbamic acid tert-butyl ester

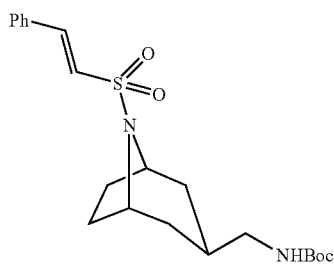

To a solution of tert-butyl 8-azabicyclo[3.2.1]oct-3-exo-ylmethylcarbamate (EXAMPLE 107, Step 1) (0.60 g, 2.5 mmol) and diisopropylethylamine (0.52 mL, 0.39 g, 3.0 mmol) in methylene chloride (15 mL), under nitrogen cooled in an ice-bath, was added dropwise over 10 minutes a solution of trans-2-phenylethenesulfonyl chloride (0.57 g, 2.8 mmol) in methylene chloride (10 mL). The resulting mixture was stirred 18 h under nitrogen while warming from ice-bath to ambient temperature. The solution was diluted with dichloromethane (125 mL), washed with 1N sodium hydroxide solution (50 mL), water (50 mL), and brine (50 mL), dried (sodium sulfate), filtered, and the solvent was evaporated under reduced pressure to give a crude product (0.95 g) as yellow gum. The crude product was purified by flash column chromatography on silica gel, eluting with ethyl acetate:hexane (33:67 increasing to 50:50) to give [8-(2-trans-phenylethenesulfonyl)-8-aza-bicyclo[3.2.1]oct-3-exo-ylmethyl]carbamic acid tert-butyl ester product as a colorless gum.

$^1$H NMR (CDCl$_3$) δ 7.50–7.40 (6H, m), 6.65 (1H, d, J 15 Hz), 4.58 (1H, br s), 4.24 (2H, br s), 3.00 (2H, m), 1.96 (3H, m), 1.69 (3H, m), 1.54 (3H, m), 1.44 (9H, m).

Step 2:

[8-(2-Phenylethanesulfonyl)-8-aza-bicyclo[3.2.1]oct-3-exo-ylmethyl]carbamic acid tert-butyl ester

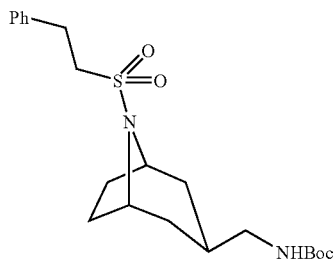

A mixture of [8-(2-trans-phenylethenesulfonyl)-8-aza-bicyclo[3.2.1]oct-3-exo-ylmethyl]carbamic acid tert-butyl ester (0.61 g, 1.5 mmol) and 20% palladium hydroxide on carbon (0.30 g) in ethanol (50 mL) was hydrogenated (52 psi hydrogen) for 18 h. The catalyst was removed by filtration through Celite. The filter cake was washed with ethanol (3×25 mL) and the filtrate was concentrated under reduced pressure to give crude [8-(2-phenylethanesulfonyl)-8-aza-bicyclo[3.2.1]oct-3-exo-ylmethyl]carbamic acid tert-butyl ester product as a gum.

$^1$H NMR (CDCl$_3$) δ 7.35–7.20 (5H, m), 4.56 (1H, br s), 4.24 (2H, br s), 3.24 (2H, m), 3.11 (2H, m), 2.98 (2H, t, J 6 Hz), 2.02 (2H, m), 1.92 (1H, m), 1.74–1.51 (4H, m), 1.44 (9H, s), 1.37 (2H, m).

Step 3:

C-[8-(2-Phenylethanesulfonyl)-8-aza-bicyclo[3.2.1]oct-3-exo-yl]methylamine

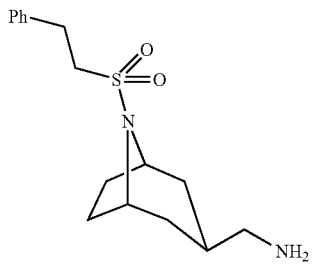

A solution of crude [8-(2-phenylethanesulfonyl)-8-aza-bicyclo[3.2.1]oct-3-exo-ylmethyl]carbamic acid tert-butyl ester (0.64 g, 1.5 mmol) in dioxane (2 mL) and 3N hydrochloric acid (2 mL) was heated at reflux for 3 h. The solvent was removed under reduced pressure. The aqueous residue was cooled in an ice-bath and made basic with 3N sodium hydroxide solution. The aqueous mixture was extracted with methylene chloride (4×20 mL). The organic layer was washed with brine (20 mL), dried (sodium sulfate), filtered, and the solvent was evaporated under reduced pressure to give a crude product (0.404 g) as a pale yellow oil. A solution of the crude product in methylene chloride was filtered through a pad of silica gel eluting with methanol:methylene chloride:ammonium hydroxide (20:80:2) to give C-[8-(2-phenylethanesulfonyl)-8-aza-bicyclo[3.2.1]oct-3-exo-yl]methylamine product as a yellow oil.

$^1$H NMR (CDCl$_3$) δ 7.32 (2H, m), 7.26 (1H, m), 7.21 (2H, d, J 7 Hz), 4.24 (2H, m), 3.24 (2H, m), 3.11 (2H, m), 2.56 (2H, d, J 6 Hz), 2.03 (2H, m), 1.82–1.65 (5H, m), 1.37 (4H, m).

Mass spec.: 309.33 (m+1).

Step 4:

[8-(2-Phenylethanesulfonyl)-8-aza-bicyclo[3.2.1]oct-3-exo-ylmethyl]pyrimidin-2-yl-amine

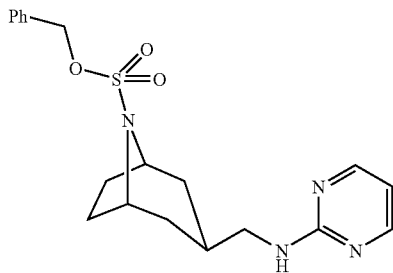

A solution of C-[8-(2-phenylethanesulfonyl)-8-aza-bicyclo[3.2.1]oct-3-exo-yl]methylamine (31 mg, 0.10 mmol), 2-bromopyrimidine (32 mg, 0.20 mmol), and diisopropylethylamine (35 μL, 0.20 mmol) in isopropanol (2 mL) was heated at reflux for 18 h. The mixture was concentrated under reduced pressure and the residue was taken up in ethyl acetate (3 mL). The resulting mixture was washed with saturated sodium bicarbonate solution (1 mL), water (2×1 mL), and brine (1 mL), dried (sodium sulfate), filtered, and the solvent was evaporated under reduced pressure to give a crude product (39 mg) as a yellow solid. The crude product was chromatographed on a 1 mm silica gel prep plate eluting with ethyl acetate:hexane (2:1) to give a colorless gum (27 mg). The gum was crystallized from ethyl acetate, the precipitate filtered off, and dried in vacuo to give [8-(2-phenylethanesulfonyl)-8-aza-bicyclo[3.2.1]oct-3-exo-ylmethyl]pyrimidin-2-yl-amine product as a white solid.

$^1$H NMR (CDCl$_3$) δ 8.26 (2H, d, J 5 Hz), 7.32 (2H, m), 7.26 (1H, m), 7.21 (2H, d, J 7 Hz), 6.53 (1H, t, J5 Hz), 5.11 (1H, m), 4.25 (2H, m), 3.31 (2H, t, t, J 6.5 Hz), 3.24 (2H, m), 3.12 (2H, m), 2.03 (3H, m), 1.74 (4H, m), 1.46 (2H, m).

Mass spec.: 387.31 (M+1).

Example 111

1-[4-(Pyridin-2-ylaminomethyl)-piperidin-1-yl]4-thiophen-2-yl-butan-1-one

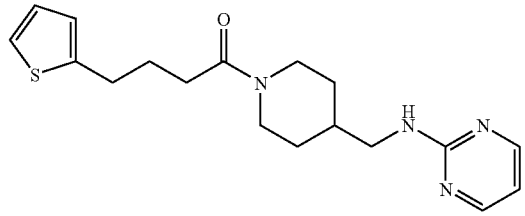

Benzyl 4-[(2-pyrimidinylamino)methyl]-1-piperidinecarboxylate (EXAMPLE 16) was hydrogenated as described in EXAMPLE 30, Step 1. The resulting piperidine was combined with EDC (1.3 equiv.), HOBT (1.0 equiv.), and 4-thiophen-2-yl-butyric acid (1.0 equiv.) in DMF and stirred for 2 h. The resulting reaction solution was partitioned into ethyl acetate and aqueous sodium bicarbonate. The organic layer was separated and washed with pH 4.5 citric acid buffer (10% citric acid and sodium hydroxide), dried (sodium sulfate), and concentrated to yield the desired 1-[4-(pyrimidin-2-ylaminomethyl)-piperidin-1-yl]4-thiophen-2-yl-butan-1-one. M.S. (M+1): 345.25

Example 112

3-Phenyl-1-[4-(pyrimidin-2-ylaminomethyl)-piperidin-1-yl]-propan-1-one

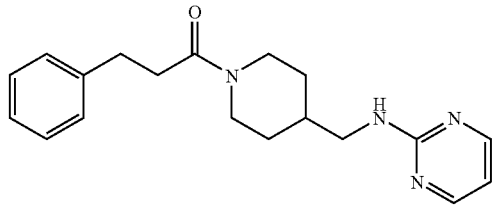

The title compound was prepared as described in EXAMPLE 111, except substituting 4-thiophen-2-yl-butyric acid with 3-phenylpropionic acid.

M.S. (M+1): 325.28

Example 113

(2-Phenyl-cyclopropyl)-[4-(pyrimidin-2-ylaminomethyl)-piperidin-1-yl]-methanone

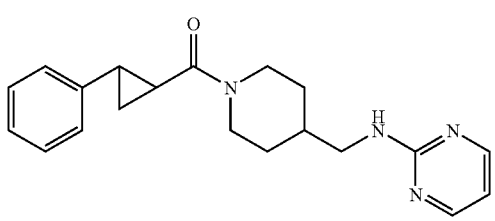

The title compound was prepared as described in EXAMPLE 111, except substituting 4-thiophen-2-yl-butyric acid with 2-phenyl-cyclopropanecarboxylic acid. M.S. (M+1): 337.27

Example 114

2-Phenoxy-1-[4-(pyrimidin-2-ylaminomethyl)-piperidin-1-yl]-ethanone

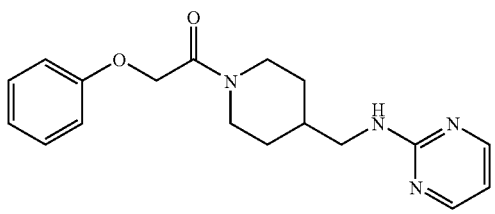

The title compound was prepared as described in EXAMPLE 111, except substituting 4-thiophen-2-yl-butyric acid with phenoxyacetic acid.

M.S. (M+1): 341.27

Example 115

4-(Pyridin-4-ylaminomethyl)-piperidine-1-carboxylic acid thiophen-3-ylmethyl ester

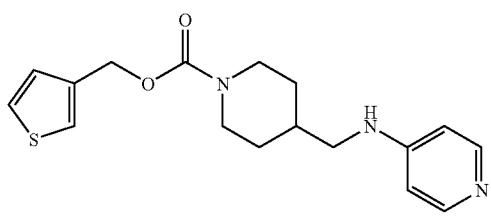

The title compound was prepared as described in EXAMPLE 30, except substituting 3-fluorobenzyl alcohol with thiophen-3-yl-methanol.

M.S. (M+1): 332.31

Example 116

N-benzyl-N'-cyano-N''-[4-(pyridin-4-ylaminomethyl)-piperidinyl]guanidine

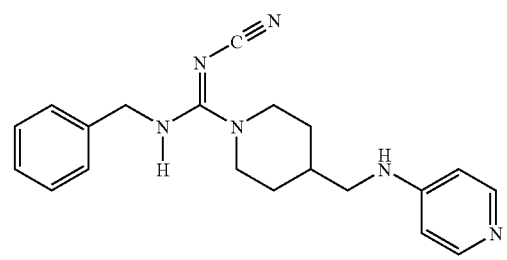

To a solution of diphenyl cyanocarbonimidate (0.44 mmol) in THF (3 mL) at −78° C. was added benzylamine (0.44 mmol, in 2 mL THF) dropwise. The cooling bath was removed, and after reaching 20° C., piperidin-4-ylmethyl-pyridin-4-yl-amine (0.44 mmol, in 2 mL DMF, EXAMPLE 30) was added. The resulting reaction mixture was heated to 90° C. for 14 h, cooled, the volatiles were removed under vacuum, and the resulting residue purified by silica gel chromatography.

M.S. (M+1): 349.38

Example 117

4-[(3-Chloro-pyrazin-2-ylamino)-methyl]-piperidine-1-carboxylic acid 4-chloro-benzyl ester

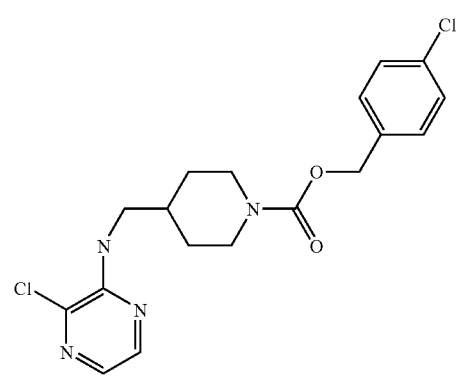

The title compound was prepared as described in EXAMPLE 47, reacting 2,3-dichloropyrazine with INTERMEDIATE 2b to give the title compound. M.S.(M+1): 395.

Example 118

4-[(3-Chloro-pyrazin-2-ylamino)-methyl]-piperi-
dine-1-carboxylic acid 4-methyl-benzyl ester

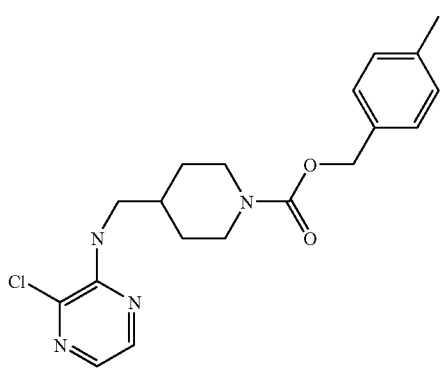

The title compound was prepared as described in EXAMPLE 47, reacting 2,3-dichloropyrazine with INTERMEDIATE 2a to give the title compound. M.S.(M+1): 375.

Example 119

4-[(3-Chloro-pyrazin-2-ylamino)-methyl]-piperi-
dine-1-carboxylic acid indan-2-yl ester

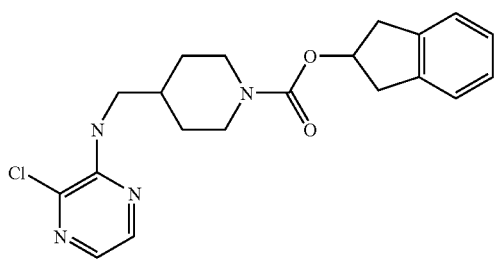

Step 1:

4-Aminomethyl-piperidine-1-carboxylic acid
indan-2-yl ester

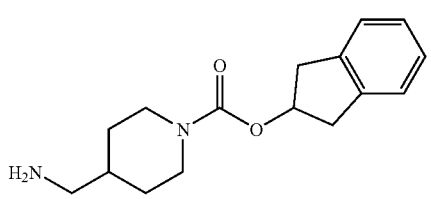

The title compound was prepared in the same way as described for the preparation of INTERMEDIATES 2A–E.

Step 2:

4-[(3-Chloro-pyrazin-2-ylamino)-methyl]-piperi-
dine-1-carboxylic acid indan-2-yl ester The title compound was prepared as described in EXAMPLE 47, reacting 2,3-dichloropyrazine with the amine described in STEP 1. M.S.(M+1): 387.

Example 120

4-[(3-Chloro-pyrazin-2-ylamino)-methyl]-piperi-
dine-1-carboxylic acid benzylamide

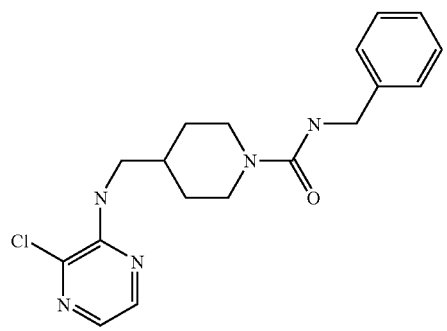

Step 1:

4-Aminomethyl-piperidine-1-carboxylic acid
benzylamide

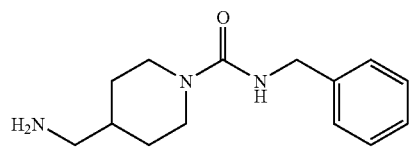

The title compound was prepared in the same way as described for the preparation of INTERMEDIATES 2A–E, replacing the INTERMEDIATE 1A–E with benzyl isocyanate Step 2:

4-[(3-Chloro-pyrazin-2-ylamino)-methyl]-piperi-
dine-1-carboxylic acid benzylamide The title compound was prepared as described in EXAMPLE 47, reacting 2,3-dichloropyrazine with the amine described in STEP 1, to give the title compound. M.S.(M+1): 360

Example 121

4-[(3-Cyano-pyrazin-2-ylamino)-methyl]-piperidine-1-carboxylic acid benzyl ester

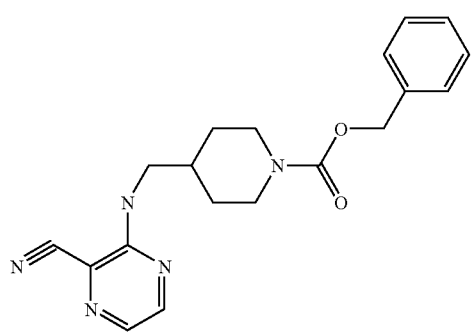

The title compound was prepared in a manner similar to that described for the preparation of EXAMPLE 47, utilizing 2-chloro-3-cyanopyrazine (Maybridge Chemicals) in place of 2,3-dichloropyrazine. M.S. (M+1): 352.

Example 122

4-[(3-Aminomethyl-pyrazin-2-ylamino)-methyl]-piperidine-1-carboxylic acid benzyl ester trifluoroacetic acid salt

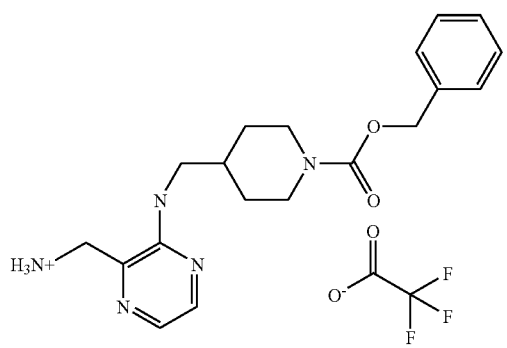

To a solution of 4-[(3-cyano-pyrazin-2-ylamino)-methyl]-piperidine-1-carboxylic acid benzyl ester (130 mg) (EXAMPLE 121) in ethanol (10 mL) under nitrogen, was added Raney Nickel (20 mg) and the mixture stirred under hydrogen (1 atm) for 8 h. The reaction was filtered, concentrated in vacuo, and then purified using reverse phase chromatography C-18 (gradient elution 0.1% aqueous trifluoroacetic acid/acetonitrile) to give the title compound as the trifluoroacetic acid salt. M.S.(M+1): 356.

Example 123

4-[(6-Aminomethyl-pyrazin-2-ylamino)-methyl]-piperidine-1-carboxylic acid benzyl ester trifluoroacetic acid salt

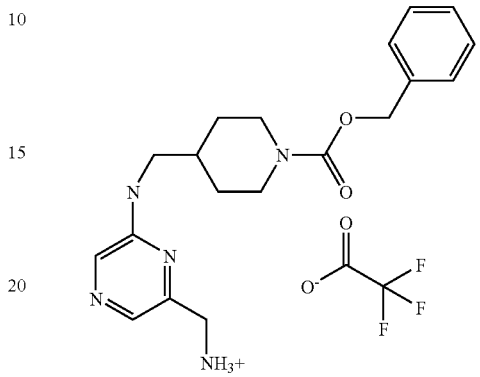

This was prepared in a manner similar to that described for the preparation of EXAMPLE 122, from 2-chloro-6-cyanopyrazine (L. Bernadi et al *Gazz. Chim. Ital.*, 91, 1431 (1961) and benzyl 4-(aminomethyl)-piperidine-1-carboxylate (EXAMPLE 13, Step 1). M.S.(M+1): 356

Example 124

4-[(3-Methoxy-pyrazin-2-ylamino)-methyl]-piperidine-1-carboxylic acid benzyl ester

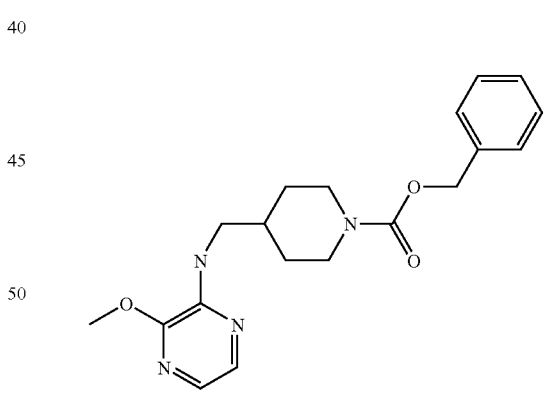

4-[(3-Chloro-pyrazin-2-ylamino)-methyl]-piperidine-1-carboxylic acid benzyl ester (2.72 g, 7.54 mmol) and 0.5 M sodium methoxide in methanol (40 mL) were heated under nitrogen at 60° C. for 2 days, cooled, evaporated and the residue partitioned between EtOAc and water. The organic layer was washed with brine, dried and solvent evaporated to afford crude material, purified by flash chromatography on silica (gradient 25 to 100% EtOAc hexane) to give the desired compound as a solid. The solid was stirred with approx. (10 ML) 2:1 isopropyl acetate:hexane and filtered to give the title compound as white solid. M.S. (M+1): 357

Example 125

4-[(3-Ethoxy-pyrazin-2-ylamino)-methyl]-piperidine-1-carboxylic acid benzyl ester

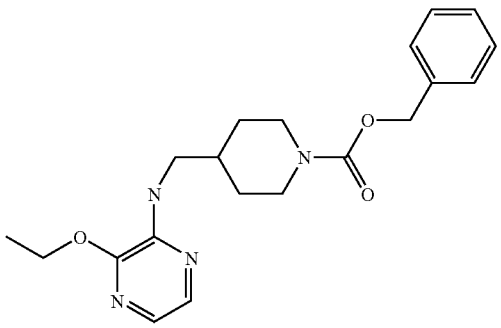

The title compound was prepared as described for EXAMPLE 124, using sodium ethoxide in ethanol in place of sodium methoxide in methanol. M.S.(M+1): 371

Example 126

4-[(3-isopropoxy-pyrazin-2-ylamino)-methyl]-piperidine-1-carboxylic acid benzyl ester

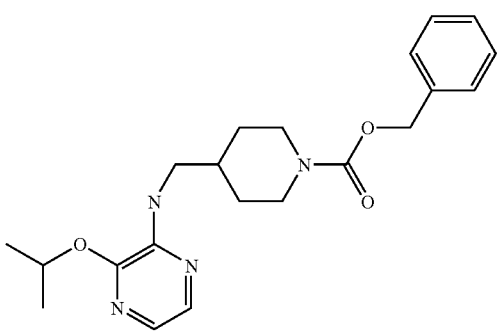

The title compound was prepared as described for EXAMPLE 124, using sodium isopropoxide in isopropanol in place of sodium methoxide in methanol. M.S.(M+1): 385

Example 127

{4-[(3-Methoxy-pyrazin-2-ylamino)-methyl]-piperidin-1-yl}-((1R,2R)-2-phenyl-cyclopropyl)-methanone

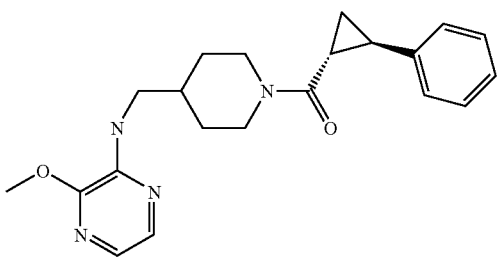

Step 1:

4-[(3-Chloro-pyrazin-2-ylamino)-methyl]-piperidine-1-carboxylic acid tert-butyl ester

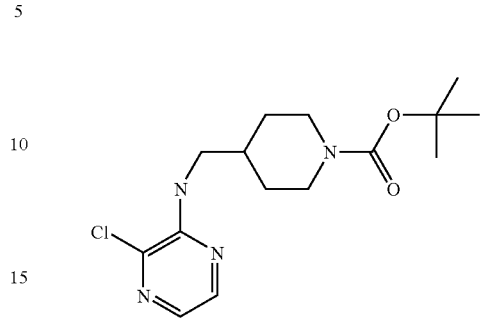

2,3-Dichloropyrazine (1.0 g, 0.0067 mol), tert-butyl-4-(aminomethyl)-piperidine-1-carboxylate (1.6 g, 0.0075 mol) (Astatech) and cesium carbonate (2.4 g, 0.0075 mol) in acetonitrile (10 mL) were heated to 90° C. under nitrogen for 18 h. The reaction was concentrated in vacuo, diluted with ethyl acetate (50 mL) and washed with water (50 mL). The organic extract was dried over sodium sulfate, filtered and chromatographed on silica using a gradient of 10 to 30% ethyl acetate/hexane to give the title compound as a foam. M.S. (M+1): 327

Step 2:

4-[(3-Methoxy-pyrazin-2-ylamino)-methyl]-piperidine-1-carboxylic acid tert-butyl ester

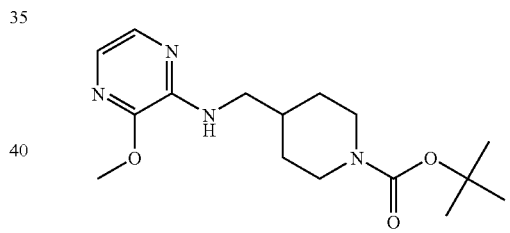

4[(3-Chloro-pyrazin-2-ylamino)-methyl]-piperidine-1-carboxylic acid tert-butyl ester (3.0 g, 0.0092 mol) and 0.5M sodium methoxide in methanol (40 mL) were heated under nitrogen at 75° C. for 18 h. The reaction was concentrated in vacuo, diluted with methylene chloride (100 mL) and washed with water (pH=9, adjusted with NaOH). The organic extract was dried over sodium sulfate filtered and concentrated to give the title compound. M.S. (M+1): 323.

Step 3:

4-[(3-Methoxy-pyrazin-2-ylamino)-methyl]-piperidine

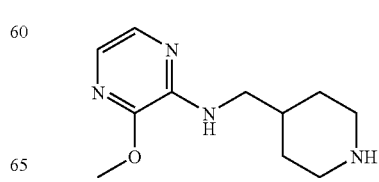

4-[(3-Methoxy-pyrazin-2-ylamino)-methyl]-piperidine-1-carboxylic acid tert-butyl ester (0.5 g, 0.0015 mol) and trifluoroacetic acid (5 mL) were allowed to stir under nitrogen for 0.5 h. The reaction was concentrated in vacuo, and chromatographed on silica using methylene chloride/methanol/ammonium hydroxide (90/10/2) to give the title compound. M.S. (M+1): 223.

Step 4:

{4-[(3-Methoxy-pyrazin-2-ylamino)-methyl]-piperidin-1-yl}-((1R,2R)-2-phenyl-cyclopropyl)-methanone

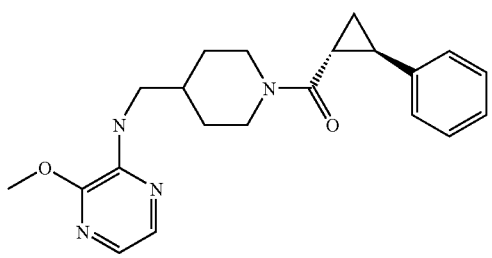

A mixture of 4-[(3-methoxy-pyrazin-2-ylamino)-methyl]-piperidine (0.093 g, 0.00042 mol), 1-hydroxybenzotriazole (0.078 g, 0.0005 mol), 1-ethyl-3-(3-dimethylaminopropyl)carbodiimide hydrochloride (0.097 g, 0.0005 mole) and (1R,2R)-2-phenylcyclopropropanecarboxylic acid (T. Riley et al., *J. Med. Chem.*, 15, 1187, 1972) (0.072 g, 0.00044 mol) in DMF (2 mL) were stirred at rt for 18 h. The reaction was diluted with ethyl acetate (30 mL), washed with 10% aqueous sodium bicarbonate (20 mL) followed by brine (10 mL), concentrated in vacuo and chromatographed on silica using 50–100% ethyl acetate/hexane. Crystallization from ether/hexane gave the title compound. M.S. (M+1): 367.

Example 128

[2-((1R,2R)-(2-Fluoro-phenyl))-cyclopropyl]-{4-[(3-methoxy-pyrazin-2-ylamino)-methyl]-piperidin-1-yl}-methanone

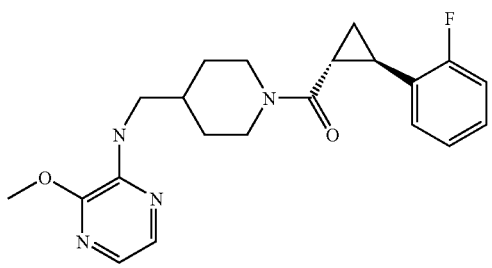

The title compound was prepared in a manner similar to that described for the preparation of EXAMPLE 127, Step 4 using (1R,2R)-2-(2-fluorophenyl)cyclopropropanecarboxylic acid, prepared as described below: M.S.(M+1): 385.

Step 1:

(R,R)-2-(2-Fluoro-phenyl)-cyclopropanecarboxylic acid tert-butyl ester

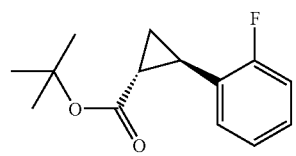

To a solution of copper triflate (2:1 benzene complex) (21 mg, 0.041 mmol) in chloroform (20 mL) under nitrogen was added 2,2'-isopropylidenebis-(4S)-4-t-butyl-2-oxazoline (12.5 mg, 0.042 mmol) and the mixture allowed to stir at rt for 1 h. The reaction was filtered under nitrogen into a flask and 2-fluorostryene (1.0 gm, 8.19 mmole) added. A solution of t-butyl diazoacetate (0.63 mL, 4.09 mmole) in chloroform (10 mL) was added dropwise over 1.5 h and the mixture allowed to stir overnight at rt. The reaction was concentrated in vacuo and chromatographed on silica using 3–10% ethyl acetate/hexane to give (hi-Rf (0.6)-trans of the title compound as an oil.

$^1$H NMR 400 MHz (δ, CDCl$_3$) δ: 1.22(m, 1H), 1.48(s, 9H), 1.54 (m, 1H), 1.84 (m, 1H), 2.58 (m, 1H), 6.9–7.1 (m, 3H), 7.17 (m,1H).

Step 2:

2-(2-Fluoro-phenyl)-cyclopropanecarboxylic acid

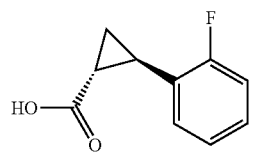

To the t-butyl ester from Step 1 (0.52 g, 0.0022 mole) in dichloromethane at 0° C. was added trifluoroacetic acid and the mixture stirred at rt for 30 min. The reaction was concentrated in vacuo to give the title compound as an oil. Analysis of the acid by chiral HPLC (Chirapak AD, 250×4.6 mm) using 95/5(A/B), 0.2% trifluroacetic acid in hexane(A) and ethanol(B), 1 mL/min, showed the material to have a purity of ≧94% EE. M.S. (M+1): 181.

Example 129

[2-((1R,2R)-(2,6-Difluoro-phenyl))-cyclopropyl]-{4-[(3-methoxy-pyrazin-2-ylamino)-methyl]-piperidin-1-yl}-methanone

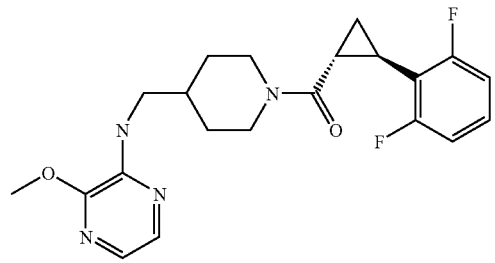

The title compound was prepared in a manner similar to that described for the preparation of EXAMPLE 127, Step 4 using (1R,2R)-2-(2,6-difluorophenyl)cyclopropropanecarboxylic acid (prepared in a similar manner to that described for 2-(2-fluoro-phenyl)-cyclopropanecarboxylic acid (EXAMPLE 128). M.S. (M+1): 403.

Example 130

4-[(3-Methoxy-pyrazin-2-ylamino)-methyl]-piperidine-1-carboxylic acid 4-methyl-benzyl ester

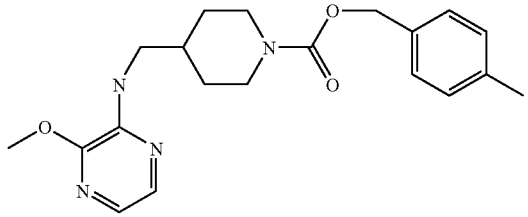

A mixture of 4-[(3-methoxy-pyrazin-2-ylamino)-methyl]-piperidine (EXAMPLE 127, STEP 3) (0.093 g, 0.00042 mol) and N-(4-methylbenzyloxycarbonyloxy)succinimide (INTERMEDIATE 1A) (118 mg) in DMF (2 mL) was stirred at rt for 18 h. The reaction was diluted with ethyl acetate (30 mL), washed with 10% aqueous sodium bicarbonate (20 mL) followed by brine (10 mL), concentrated in vacuo and chromatographed on silica using a gradient elution of 5–15% acetone/dichloromethane. Concentration in vacuo followed by crystallization from ether/hexane gave the title compound. M.S. (M+1): 371.

Example 131

4-[(5-Cyano-3-methoxy-pyrazin-2-ylamino)-methyl]-piperidine-1-carboxylic acid benzyl ester

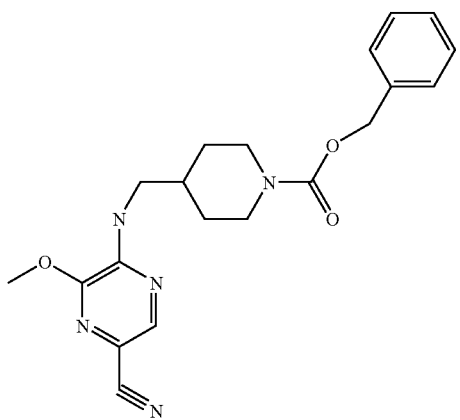

Step 1:

4-[(5-Bromo-3-methoxy-pyrazin-2-ylamino)-methyl]-piperidine-1-carboxylic acid tert-butyl ester

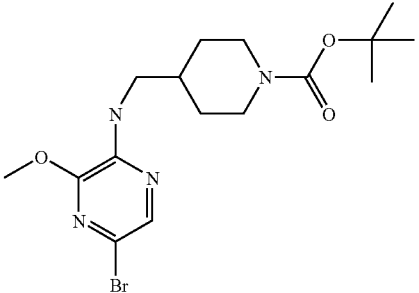

To 4-[(3-methoxy-pyrazin-2-ylamino)-methyl]-piperidine-1-carboxylic acid tert-butyl ester (EXAMPLE 127, STEP 2) (2.0 g, 0.0062 mol) in chloroform (160 mL) and under nitrogen was added pyridine (0.528 mL, 0.0064 mol), followed by a slow addition (~1 h) of a solution of bromine (1.044 g, 0.0064 mol) in chloroform (16 mL). The reaction was diluted with water (100 mL) and the organic layer removed, dried over sodium sulfate, filtered and concentrated to an oil. The oil was chromatographed on silica using a gradient of 0 to 4% acetone/dichloromethane to give the title compound as a foam. M.S. (M+1): 401.

Step 2:

4-[(5-Cyano-3-methoxy-pyrazin-2-ylamino)-methyl]-piperidine-1-carboxylic acid tert-butyl ester

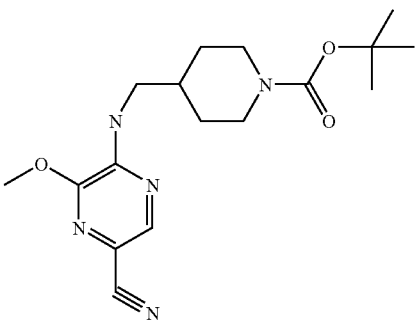

To 4-[(5-bromo-3-methoxy-pyrazin-2-ylamino)-methyl]-piperidine-1-carboxylic acid tert-butyl ester (0.5 g, 0.00125 mol) in DMSO (10 mL), under nitrogen, was added copper cyanide (0.565 g, 0.00625 mol) and the mixture heated to 150° C. for 1.5 h. The reaction mixture was cooled to rt, diluted with a mixture of 20% ammonium hydroxide in water (50 mL) and dichloromethane (50 mL) and allowed to stir for 1 h. The organic layer was removed, dried over sodium sulfate and concentrated to an oil. The oil was chromatographed on silica using a gradient of 20–40% ethyl acetate/hexane to give the title compound as a foam. M.S. (M+1): 348.

Step 3:

4-[(5-Cyano-3-methoxy-pyrazin-2-ylamino)-methyl]-piperidine

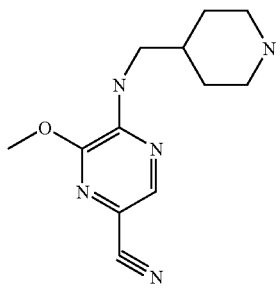

The above compound was prepared in a similar manner as described in EXAMPLE 127, STEP 3 from 4-[(5-cyano-3-methoxy-pyrazin-2-ylamino)-methyl]-piperidine-1-carboxylic acid tert-butyl ester. M.S. (M+1): 248.

Step 4:

4-[(5-Cyano-3-methoxy-pyrazin-2-ylamino)-methyl]-piperidine-1-carboxylic acid benzyl ester The above compound was prepared in a similar manner as described in EXAMPLE 130 from 4-[(5-cyano-3-methoxy-pyrazin-2-ylamino)-methyl]-piperidine using N-(benzyloxycarbonyloxy)succinimide (Sigma-Aldrich). M.S. (M+1): 382.

Example 132

6-Methoxy-5-{[1-(2-(1R,2R)-phenyl-cyclopropanecarbonyl)-piperidin-4-ylmethyl]-amino}-pyrazin-2-carbonitrile

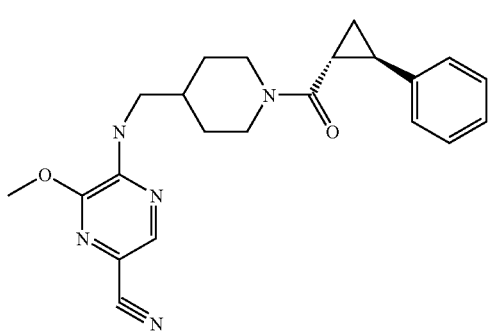

The above compound was prepared in a similar manner as described in EXAMPLE 127, STEP 4 from 4-[(5-cyano-3-methoxy-pyrazin-2-ylamino)-methyl]-piperidine (EXAMPLE 131, STEP 3). M.S. (M+1): 392.

Example 133

4-[(3-Methoxy-5-methyl-pyrazin-2-ylamino)-methyl]-piperidine-1-carboxylic acid benzyl ester

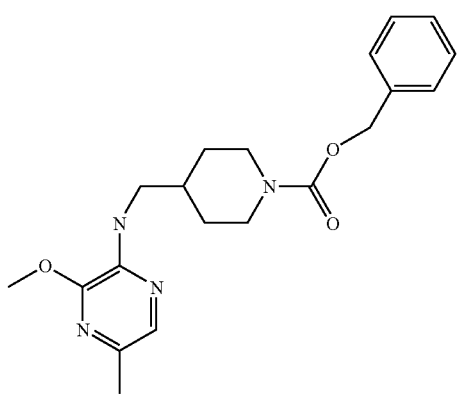

Step 1:

4-[(3-Methoxy-5-methyl-pyrazin-2-ylamino)-methyl]-piperidine-1-carboxylic acid tert-butyl ester

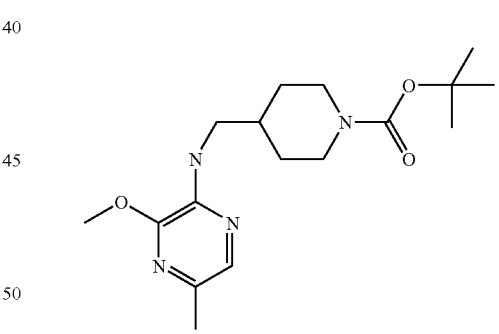

To 4-[(5-bromo-3-methoxy-pyrazin-2-ylamino)-methyl]-piperidine-1-carboxylic acid tert-butyl ester (EXAMPLE 131, STEP 1) (0.20 g, 0.0005 mol) in tetrahydrofuran (1 mL), under nitrogen, was added 1,3-bis(diphenylphosphino)propane nickel(II) chloride (0.034 g, 0.0625 mmol) followed by a dropwise addition of 2.0M dimethylzinc in toluene (0.313 mL, 0.000625 mol). The reaction mixture was stirred for 1.5 h, diluted with water (5 mL) and ethyl acetate (30 mL). The organic layer was removed, dried over sodium sulfate, filtered and concentrated to an oil. The oil was chromatographed on silica using a gradient of 20–50% ethyl acetate/hexane to give the title compound as a foam. M.S. (M+1): 337.

Step 2

4-[(3-Methoxy-5-methyl-pyrazin-2-ylamino)-methyl]-piperidine

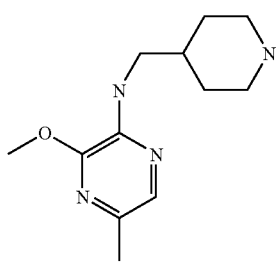

The above compound was prepared in a similar manner as described in EXAMPLE 127, STEP 3 from 4-[(3-methoxy-5-methyl-pyrazin-2-ylamino)-methyl]-piperidine-1-carboxylic acid tert-butyl ester. M.S. (M+1): 237

Step 3:

4-[(3-Methoxy-5-methyl-pyrazin-2-ylamino)-methyl]-piperidine-1-carboxylic acid benzyl ester

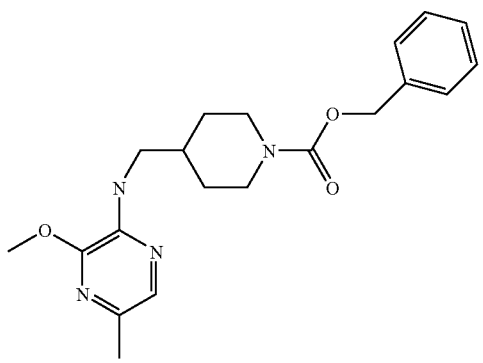

The above compound was prepared in a similar manner as described in EXAMPLE 130 from 4-[(3-methoxy-5-methyl-pyrazin-2-ylamino)-methyl]-piperidine using N-(benzyloxycarbonyloxy)succinimide (Sigma-Aldrich). M.S. (M+1): 371.

Example 134

4-[(3-Methoxy-5-methyl-pyrazin-2-ylamino)-methyl]-piperidine-1-carboxylic acid 4-methyl-benzyl ester

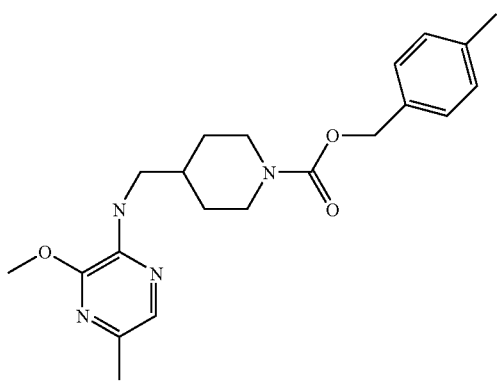

The above compound was prepared in a similar manner as described in EXAMPLE 130 from 4-[(3-methoxy-5-methyl-pyrazin-2-ylamino)-methyl]-piperidine (EXAMPLE 130, STEP 2) using N-(4-methylbenzyloxycarbonyloxy)succinimide (INTERMEDIATE 1A). M.S. (m+1): 385.

Example 135

{4-[(3-Methoxy-5-methyl-pyrazin-2-ylamino)-methyl]-piperidin-1-yl}-(2-((1R,2R)-phenyl)-cyclopropyl)-methanone

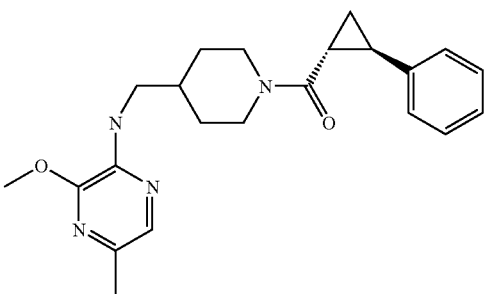

The above compound was prepared in a similar manner as described in EXAMPLE 127, STEP 4, from 4-[(3-methoxy-5-methyl-pyrazin-2-ylamino)-methyl]-piperidine (EXAMPLE 133, STEP 2). M.S. (M+1): 381.

Example 136 trans N-[(1-{[2-(2-Fluorophenyl)cyclopropyl]carbonyl}piperidin-4-yl)methyl]-5-fluoropyrimidin-2-amine

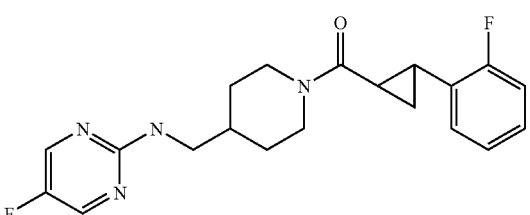

Step 1:

Methyl (2E)-3-(2-fluorophenyl)prop-2-enoate

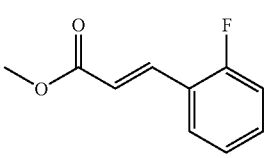

HCl gas was bubbled through a stirring solution of 2-fluorocinnamic acid in anhydrous methanol. The reaction mixture was allowed to cool to room temperature, then concentrated to yield the title compound. M.S. (M+1): 181.

Step 2:

Methyl 2-(2-fluorophenyl)cyclopropanecarboxylate

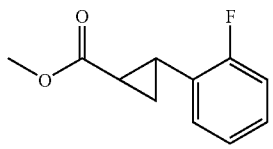

Diazomethane was prepared as follows: To a stirring solution of ether (290 mL) and 40% KOH (aq, 90 mL) at 0° C., was added 1-methyl-3-nitro-1-nitrosoguanidine (24.42 g, 166.53 mmol), portionwise. After stirring for 1 h, the mixture was cooled to −78° C. and allowed to stir for an additional ten minutes. The ether layer and palladium acetate (approx 200 mg) were then both added in approx. 10 portions to a stirred solution of methyl (2E)-3-(2-fluorophenyl)prop-2-enoate (3.0 g, 16.65 mmol) in ether (20 mL) at 0° C. After stirring at rt for approximately thirty minutes, the reaction mixture was then filtered through silica gel and concentrated. M.S. (M+1): 195.

Step 3:

Preparation of
2-(2-fluorophenyl)cyclopropanecarboxylic acid

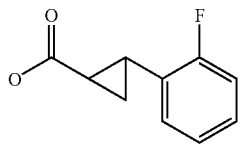

To a stirred solution of methyl 2-(2-fluorophenyl)cyclopropanecarboxylate (4.8 g, 24.72 mmol) in tetrahydrofuran (25 mL), was added 10M sodium hydroxide solution (approximately 2 mL), a small amount of water, and sufficient methanol to achieve a homogeneous reaction mixture. The reaction mixture was then allowed to stir at rt for approximately 2 h. After concentrating the reaction mixture, 1N HCl was added until the mixture was acidic. The organic layer was extracted twice with ethyl acetate, then washed with brine, dried over anhydrous $Na_2SO_4$, and concentrated to afford the title compound. M.S. (M+1): 181.

Step 4:

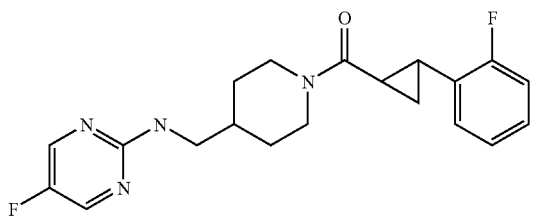

N-[(1-{[2-(2-fluorophenyl)cyclopropyl]carbonyl}piperidin-4-yl)methyl]-5-fluoropyrimidin-2-amine A solution of 4-[(5-fluoro-pyrimidin-2-ylamino)-methyl]-piperidine-1-carboxylic acid benzyl ester (EXAMPLE 71, STEP 2) was hydrogenated at 1 atm. of hydrogen over 10% Pd/C in ethanol until debenzylation was complete. The reaction mixture was then filtered, the catalyst washed with ethanol and solvent evaporated to give the deprotected amine which was coupled with 2-(2-fluorophenyl)cyclopropanecarboxylic acid using the conditions described in EXAMPLE 127, STEP 4 to give the title compound after chromatography on silica.

$^1$H NMR (400 MHz): δ 8.15 (m, 2H); 7.17 (brs, 1H); 7.04 (m, 2H); 5.47 (brs, 1H); 4.65 (brs, 1H); 4.15 (d, 1H); 3.31 (m, 2H); 3.08 (t, 1H); 2.56 (m, 2H); 2.02 (brs, 1H); 1.90 (m, 3H); 1.67 (m, 1H); 1.22 (m, 4H).

M.S. (M+1): 373.

Example 137

(S,S) and (R,R) N-[(1-{[2-(2-fluorophenyl)cyclopropyl]carbonyl}piperidin-4-yl)methyl]-5-fluoropyrimidin-2-amine

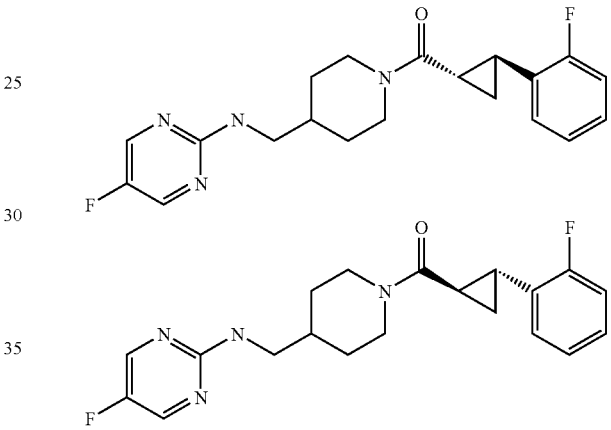

Separation of the two enantiomers of N-[(1-{[2-(2-fluorophenyl)cyclopropyl]carbonyl}piperidin-4-yl)methyl]-5-fluoropyrimidin-2-amine was accomplished on a Chiralpak AD column, eluting with 0.1% diethylamine in hexane/2-propanol.

Example 138

N-[(1-{[2-(2,6-difluorophenyl)cyclopropyl]carbonyl}piperidin-4-yl)methyl]-5-fluoropyrimidin-2-amine

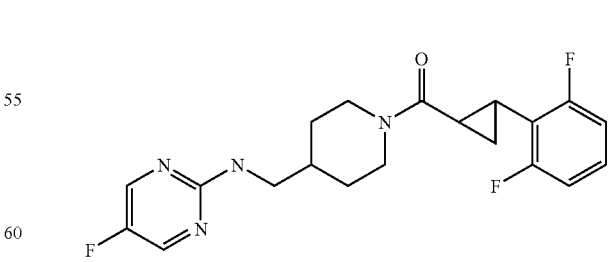

The title compound was prepared in a manner similar to that described for EXAMPLE 136, starting with 2,6-difluorocinnamic acid.

$^1$H NMR (400 MHz, $CDCl_3$): δ 8.16 (s, 2H); 7.13 (brs, 1H); 6.82 (dd, 2H); 5.20 (s, 1H); 4.67 (m, 1H); 4.23 (m, 1H);

3.32 (dd, 2H); 3.11 (m, 1H); 2.64 (m, 1H); 2.38 (m, 1H); 2.30 (m, 1H); 1.94–1.80 (m, 2H); 1.66 (m, 2H); 1.40–1.39 (m, 1H); 1.27–1.22 (m, 2H).

M.S. (M+1): 391.

Example 139

(S,S) and (R,R) N-[(1-{[2-(2,6-difluorophenyl)cyclopropyl]carbonyl}piperidin-4-yl)methyl]-5-fluoropyrimidin-2-amine

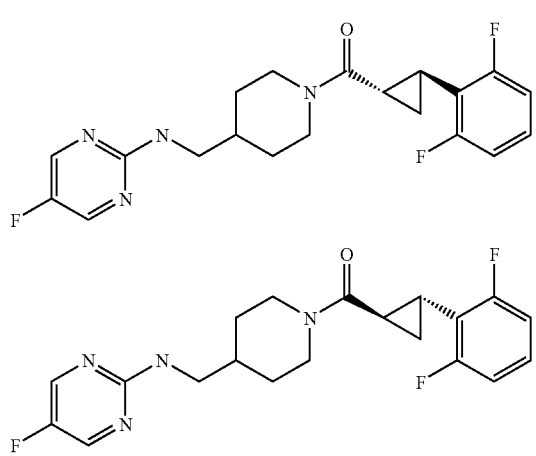

Separation of the two enantiomers of N-[(1-{[2-(2-fluorophenyl)cyclopropyl]carbonyl}piperidin-4-yl)methyl]-5-fluoropyrimidin-2-amine was accomplished on a Chiralpak AD column, eluting with 0.1% diethylamine in hexane/2-propanol.

Example 140

N-[(1-{[2-(2,3-difluorophenyl)cyclopropyl]carbonyl}piperidin-4-yl)methyl]-5-fluoropyrimidin-2-amine

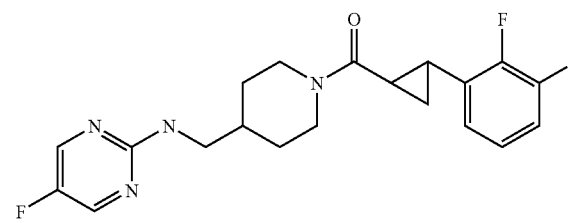

The title compound was prepared in a manner similar to that described for EXAMPLE 136 using 2,3-difluorocinnamic acid.

¹H NMR (400 Mz): δ 8.15 (s, 2H); 7.00 (m, 2H); 6.77 (brs, 1H); 5.44 (brs, 1H); 4.65 (brs, 1H); 4.14 (d, 1H); 3.09 (t, 1H); 2.59 (m, 2H); 2.05 (brs, 1H); 1.89 (m, 3H); 1.69 (brs, 1H); 1.26 (m, 3H).

M.S. (M+1): 391.

Example 141

(S,S) and (R,R) N-[(1-{[2-(2,3-difluorophenyl)cyclopropyl]carbonyl}piperidin-4-yl)methyl]-5-fluoropyrimidin-2-amine

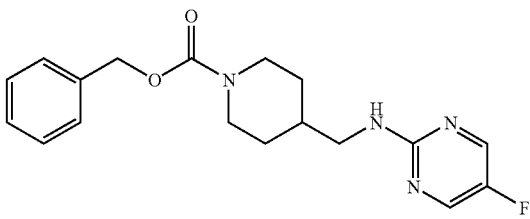

Separation of the two enantiomers of N-[(1-{[2-(2,3-difluorophenyl)cyclopropyl]carbonyl}piperidin-4-yl)methyl]-5-fluoropyrimidin-2-amine was accomplished on a Chiralpak AD column, eluting with 0.1% diethylamine in hexane/2-propanol.

Example 142

Benzyl 4-{[(5-fluoro-pyrimidin-2-yl)amino]methyl}piperidine-1-carboxylate

Step 1:

2,4-dichloro-5-fluoropyrimidine

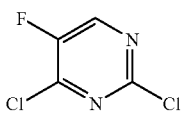

A stirred solution of 5-fluorouracil (15.0 g, 0.115 mol), N,N-dimethylaniline (7.31 mL, 0.058 mol) in POCl₃ (107 mL) was heated to reflux for 1 h. The reaction mixture was concentrated in vacuo and the residue quenched with ice (100 g) at 0° C. The solution was then extracted with ethyl ether (3×200 mL). The combined ether layer was washed with aqueous saturated NaHCO₃ (100 mL), water (100 mL), brine (50 mL), dried over Na₂SO₄, filtered and concentrated to give the title compound.

¹H NMR (400 MHz, CDCl₃): δ 8.49 (s, 1 H, Ar).

Step 2:

2-Chloro-5-fluoropyrimidine (7)

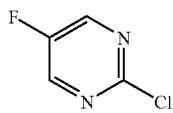

To a stirred, refluxing mixture of 2,4-dichloro-5-fluoropyrimidine (17.0 g, 0.102 mol) and zinc (100 mesh, 20.0 g, 0.305 mol) in THF (100 mL) was slowly added acetic acid (5.8 mL, 0.102 mol). The resulting reaction mixture was refluxed for 3 h, then cooled to RT. Solids were removed by filtration and the filtrate concentrated in vacuo. The residue was chromatographed on silica gel 60 (200 g), eluting with 10–50% ethyl acetate in hexane to give the title compound.
¹H NMR (400 MHz, CDCl₃): δ 68.53 (s, 2H, Ar).

Step 3:

Benzyl 4-{[(5-fluoro-pyrimidin-2-yl)amino]methyl}piperidine-1-carboxylate

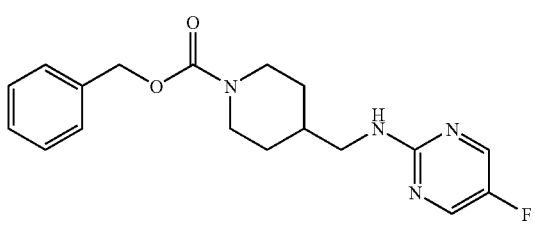

A stirred mixture of benzyl 4-(aminomethyl)-piperidine-1-carboxylate (EXAMPLE 13, STEP 1) (10.0 g, 0.040 mol), 2-chloro-5-fluoropyrimidine (5.3 g, 0.040 mol) and cesium carbonate (26.2 g, 0.081 mol) in DMF (100 mL) was heated at 100° C. for 2 h. The reaction mixture was cooled to rt, diluted with ethyl acetate (400 mL), washed with aqueous saturated NaHCO₃ (100 mL), water (5×100 mL), and brine (50 mL), dried over anhydrous Na₂SO₄, filtered and concentrated. The residue was chromatographed on silica gel 60 (0.5 kg), eluting with 50–100% ethyl acetate in hexane to give the title compound. M.S. (M+1): 345.

¹H NMR (400 MHz, CDCl₃): δ 8.15 (s, 2 H, Pyr), 7.35 (m, 5 H, Ar), 5.12 (s, 2H, ArCH₂), 4.21 (brs, 2H, NCH₂), 3.29 (t, J=6.4 Hz, 2H, NHCH₂), 2,78 (brs, 2H, NCH₂), 1.80 (m, 2H, CH), 1.77 (m, 2H, CHCH₂CH₂), 1.20 (m, 2H, CHCH₂CH₂).

Example 143

5-Fluoro-2-{[(1-{[(1R,2R)-2-phenylcyclopropyl]carbonyl}piperidin-4-yl)methyl]amino}pyrimidine

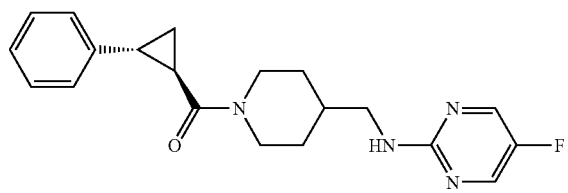

Step 1:

5-Fluoro-N-(piperidin-4-ylmethyl)pyrimidin-2-amine

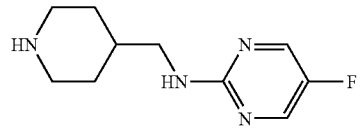

A mixture of benzyl 4-{[(5-fluoropyrimidin-2-yl)amino]methyl}piperidine-1-carboxylate (EXAMPLE 142, STEP 3) (9.0 g, 0.026 mol) and Pd/C (10%, 0.9 g) in anhydrous methanol (250 mL) was vigorously stirred under hydrogen atmosphere provided by a hydrogen balloon for 2 h. The reaction mixture was filtered and the filtrate was concentrated to give the title compound. M.S. (M+1): 211.

¹H NMR (400 MHz, CDCl₃): δ 8.15 (s, 2H, Pyr), 5.19 (s, 1H, NH), 3.27 (t, J=6.3 Hz, 2H, NHCH₂CH), 3.11 (d, J=9.1 Hz, 2H, NHCH₂CH₂), 2.61 (t, J=12.1 Hz, 2H, NHCH₂CH₂), 1.77 (d, J=12.7 Hz, 2H, CH₂CH₂CH), 1.73 (m, 1H, CH), 1.24 (m, 2H, CH₂CH₂CH).

Step 2:

5-Fluoro-2-{[(1-{[(1R,2R)-2-phenylcyclopropyl]carbonyl}piperidin-4-yl)methyl]amino}-pyrimidine

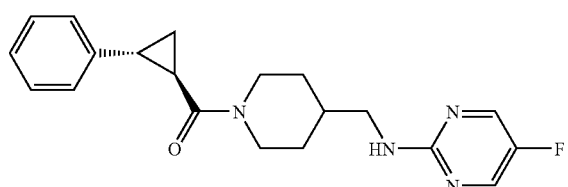

A solution of 5-fluoro-N-(piperidin-4-ylmethyl)pyrimidin-2-amine (1.00 g, 4.76 mmol), (1R,2R)-2-phenylcyclopropanecarboxylic acid (T. Riley et al., J. Med. Chem., 15, 1187, 1972) (0.77 g, 4.76 mmol), EDC (1.37 g, 7.13 mmol) and HOBt (0.96 g, 7.13 mmol) in DMF (10 mL) was stirred at rt for 2 h. The reaction mixture was diluted with ethyl acetate (200 mL), washed with aqueous saturated NaHCO₃ (50 mL), water (5×50 mL), brine (20 mL), dried over Na₂SO₄, filtered and concentrated. The residue was chromatographed on silica gel 60 (90 g), eluting with 10:1–15:89–75 CH$_2$Cl$_2$:2-propanol:hexane to give the title compound. M.S. (M+1): 355.

$^1$H NMR (400 MHz, CDCl$_3$): δ 8.15 (s, 2H, Pyr), 7.28 (t, J=7.6 Hz, 2 H, Ar), 7.19 (t, J=6.6 Hz, 1H, Ar), 7.10 (d, J=7.4 Hz, 2H, Ar), 5.15 (s, 1H, NH), 4.64 (d, J=13.5 Hz, 1H, NCH$_2$), 4.14 (d, J=12.7 Hz, 1H, NCH$_2$), 3.30 (s, 2H, CH$_2$NH), 3.06 (q, J=12.8 Hz, 1H, NCH$_2$), 2.62 (t, J=12.1 Hz, 1H, NCH$_2$), 2.46 (brs, 1H, ArCH), 1.98 (m, 1H, CHCO), 1.87 (m, 1H, CH$_2$CHCH$_2$), 1.82 (m, 2H, CH$_2$CH$_2$CH), 1.65 (m, 1H, CHCH$_2$CH), 1.26 (m, 1H, CHCH$_2$CH), 1.21 (m, 2H, CH$_2$CH$_2$CH).

Example 144

Benzyl 4-{[(5-methylpyrimidin-2-yl)amino]methyl}piperidine-1-carboxylate

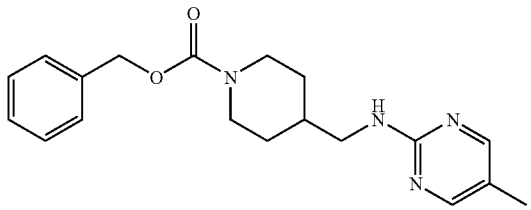

Step 1:

2-chloro-5-methylpyrimidine

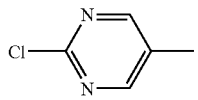

To a stirred, refluxing mixture of 2,4-dichloro-5-methylpyrimidine [1780-31-0](Sigma-Aldrich) (40.0 g, 0.245 mol) and zinc (100 mesh, 48.1 g, 0.736 mol) in THF (250 mL) was slowly added acetic acid (14.0 mL, 0.245 mol). The resulting reaction mixture was refluxed for 3 h, then cooled to RT. The solids were removed by filtration and the filtrate concentrated in vacuo. The residue was chromatographed on silica gel 60 (0.5 kg), eluting with a gradient of 10–50% ethyl acetate in hexane to give the title compound. M.S. (M+1): 129.

$^1$H NMR (400 MHz, CDCl$_3$): δ 8.47 (s, 2H, Ar), 2.32 (s, 3H, CH$_3$).

Step 2:

Benzyl 4-{[(5-methylpyrimidin-2-yl)amino]methyl}piperidine-1-carboxylate

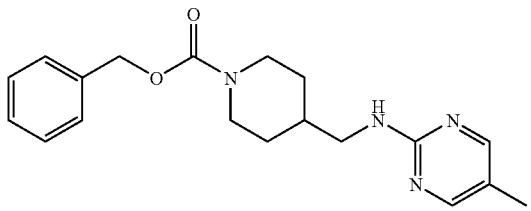

A stirred mixture of benzyl 4-(aminomethyl)-piperidine-1-carboxylate (EXAMPLE 13, STEP 1) (20.0 g, 0.081 mol), 2-chloro-5-methylpyrimidine (10.4 g, 0.081 mol) and cesium carbonate (52.5 g, 0.161 mol) in DMF (200 mL) was heated at 150° C. for 6 h. The reaction mixture was cooled to rt, diluted with ethyl acetate (700 mL), washed with aqueous saturated NaHCO$_3$ (200 mL), water (5×200 mL), and brine (100 mL), dried over anhydrous sodium sulfate, filtered and concentrated. The residue was chromatographed on silica gel 60 (1 kg), eluting with 50–100% ethyl acetate in hexane to give the title compound. M.S. (M+1): 341.

$^1$H NMR (400 MHz, CDCl$_3$): δ 8.11 (s, 2H, Pyr), 7.35 (m, 5H, Ar), 5.12 (s, 2H, ArCH$_2$), 5.00 (s, 1H, NH), 4.20 (brs, 2H, NCH$_2$), 3.31 (t, J=6.3 Hz, 2 H, NHCH$_2$), 2.77 (brs, 2H, NCH$_2$), 2.12 (s, 3H, CH$_3$), 1.78 (m, 1 H CH), 1.77 (m, 2 H, CHCH$_2$CH$_2$), 1.20 (m, 2H, CHCH$_2$CH$_2$).

Example 145

5-Methyl-2-{[(1-{[(1R,2R)-2-phenylcyclopropyl]carbonyl}piperidin-4-yl)methyl]amino}pyrimidine

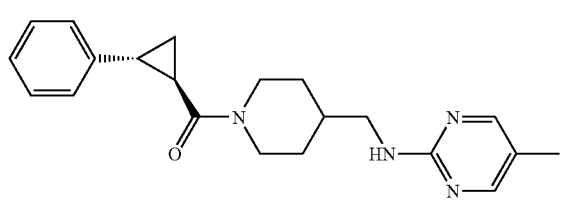

Step 1:

5-Methyl-N-(piperidin-4-ylmethyl)pyrimidin-2-amine

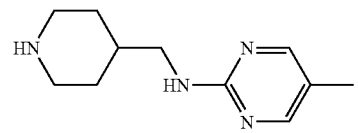

A mixture of benzyl 4-{[(5-methylpyrimidin-2-yl)amino]methyl}piperidine-1-carboxylate (EXAMPLE 144) (13.0 g, 0.038 mol) and Pd/C (10%, 1.3 g) in anhydrous methanol (500 mL) was vigorously stirred under a hydrogen atmosphere provided by a hydrogen balloon for 6 h. The reaction mixture was filtered and the filtrate was concentrated to give 5-methyl-N-(piperidin-4-ylmethyl)pyrimidin-2-amine. M.S. (M+1): 207.

$^1$H NMR (400 MHz, CDCl$_3$): δ 8.11 (s, 2H), 5.10 (s, 1H), 3.30 (t, J=6.4 Hz, 2H), 3.20 (d, J=12.3 Hz, 2H), 2.65 (dt, J=12.3 & 2.6 Hz, 2H), 2.12 (s, 3 H), 1.82 (d, J=13.5 Hz, 2H), 1.77 (m, 1H), 1.31(q d, J=12.1 & 3.7 Hz, 2H).

Step 2:

5-Methyl-2-{[(1-{[(1R,2R)-2-phenylcyclopropyl]carbonyl}piperidin-4-yl)methyl]amino}pyrimidine

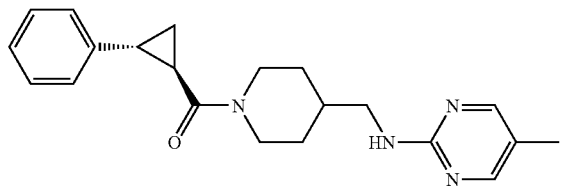

A solution of 5-methyl-N-(piperidin-4-ylmethyl)pyrimidin-2-amine (5.00 g, 0.024 mol), (1R,2R)-2-phenylcyclopropanecarboxylic acid (T. Riley et al., *J. Med. Chem.*, (1972), 15, 1187) (3.93 g, 0.024 mol), EDC (6.97 g, 0.036 mol) and HOBt (4.91 g, 0.036 mol) in DMF (50 mL) was stirred at RT for 2 h. The reaction mixture was diluted with ethyl acetate (400 mL), washed with aqueous saturated NaHCO$_3$ (100 mL), water (5×100 mL), brine (50 mL), dried over anhydrous sodium sulfate, filtered and concentrated. The residue was chromatographed on silica gel 60 (400 g), eluting with 50–100% ethyl acetate in hexane to give 5-methyl-2-{[(1-{[(1R,2R)-2-phenylcyclopropyl]carbonyl}piperidin-4-yl)methyl]amino}pyrimidine. M.S. (M+1): 351.

$^1$H NMR (400 MHz, CDCl$_3$): δ 8.11 (s, 2H), 7.28 (t, J=7.0 Hz, 2H), 7.19 (t, J=7.2 Hz, 1H), 7.11 (d, J=7.6 Hz, 2H), 5.01 (s, 1H), 4.63 (d, J=12.1 Hz, 1H), 4.13 (d, J=13.2 Hz, 1H), 3.31 (s, 2H), 3.05 (q, J=12.2 Hz, 1H), 2.62 (t, J=12.5 Hz, 1H), 2.46 (brs, 1H), 2.12 (s, 3H), 1.97 (s, 1H), 1.86 (m, 1H), 1.81 (d, J=13.3 Hz, 2H), 1.64 (s, 1H), 1.26 (s, 1H), 1.22 (m, 2H).

Example 145A

5-Methyl-2-{[(1-{[(1R,2R)-2-phenylcyclopropyl]carbonyl}piperidin-4-yl)methyl]amino}pyrimidinium chloride

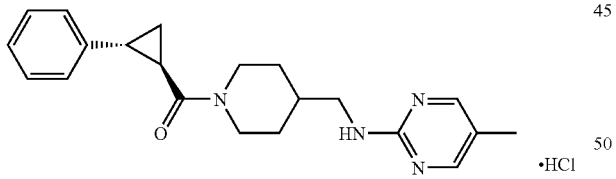

5-Methyl-2-{[(1-{[(1R,2R)-2-phenylcyclopropyl]carbonyl}piperidin-4-yl)methyl]amino}-pyrimidine (6.81 g, 19.4 mmol) (EXAMPLE 145) was dissolved in EtOH (400 mL) and 1M HCl in ether (19.4 mL, 19.4 mmol) added. The solution was then concentrated and the residue was crystallized from 30% 2-propanol in ether (100 mL) to give the title compound. Melting Point 157.5° C.

M.S. (M+1): 351.

$^1$H NMR (500 MHz, CD$_3$OD): δ 8.42 (s, 2H), 7.25 (m, 2H), 7.17 (m, 1H), 7.14 (m, 2H), 4.55 (d, J=12.9 Hz, 1H), 4.26 (m, 1H), 3.38 (m, 2H), 3.14 (q, J=12.9 Hz, 1H), 2.69 (t, J=12.1 Hz, 1H), 2.33 (m, 1H), 2.24 (s, 3H), 2.19 (brs, 1 H), 1.97 (m, 1H), 1.82 (m, 1H), 1.53 (m, 1H), 1.29 (m, 1H), 1.17 (m, 2 H).

Example 146

5-Methyl-N-[(1-{[2-(5-methylthien-2-yl)cyclopropyl]carbonyl}piperidin-4-yl)methyl]pyrimidin-2-amine

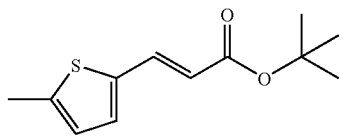

Step 1:

tert-Butyl (2E)-3-(5-methylthien-2-yl)prop-2-enoate

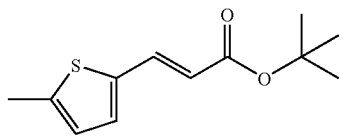

To a solution of tert-butyl diethylphosphonoacetate (1.12 mL, 4.76 mmol) in THF (5 mL) at −78° C. was added LHMDS (1.0M in THF, 4.76 mL, 4.76 mmol). After 5 min at −78° C. 5-methyl-2-thiophene-carboxaldehyde (0.43 mL, 3.96 mmol) was added. The reaction mixture was warmed to RT, stirred for 10 min and poured onto EtOAc/H$_2$O. The layers were separated and the organic layer was washed with H$_2$O, dried over Na$_2$SO$_4$, filtered and concentrated. The residue was chromatographed on silica (gradient elution; hexanes to 4:1 hexanes:EtOAc) to give tert-butyl (2E)-3-(5-methylthien-2-yl)prop-2-enoate as a clear oil.

Step 2:

tert-Butyl 2-(5-methylthien-2-yl)cyclopropanecarboxylate

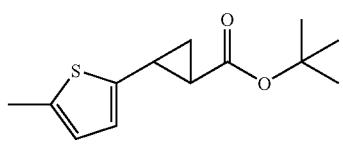

tert-Butyl (2E)-3-(5-methylthien-2-yl)prop-2-enoate was cyclopropanated according to the procedure described for EXAMPLE 136, STEP 2, providing, after chromatography, ten-butyl 2-(5-methylthien-2-yl)cyclopropanecarboxylate.

Step 3:

2-(5-Methylthien-2-yl)cyclopropanecarboxylic acid

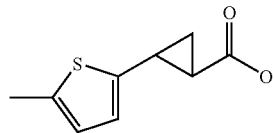

To a solution of tert-butyl 2-(5-methylthien-2-yl)cyclopropanecarboxylate (100 mg, 0.42 mmol) in CH$_2$Cl$_2$ (3 mL) at RT was added trifluoroacetic acid (1 mL). The reaction mixture was stirred at RT for 10 min and concentrated in vacuo. The crude 2-(5-methylthien-2-yl)cyclopropanecarboxylic acid was used without further purification. M.S.(M+1) 182

Step 4:

5-Methyl-N-[(1-{[2-(5-methylthien-2-yl)cyclopropyl]carbonyl}piperidin-4-yl)methyl]pyrimidin-2-amine

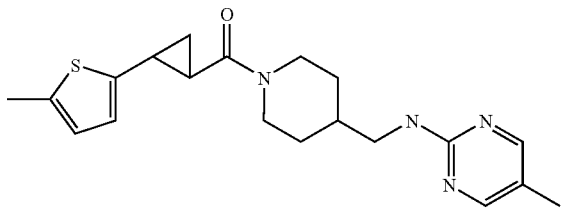

2-(5-Methylthien-2-yl)cyclopropanecarboxylic acid was coupled to amine 5-methyl-N-(piperidin-4-ylmethyl)pyrimidin-2-amine (EXAMPLE 144, STEP 3) according to the procedure described for EXAMPLE 144, STEP 4, providing, after chromatography, 5-methyl-N-[(1-{[2-(5-methylthien-2-yl)cyclopropyl]carbonyl}piperidin-4-yl)methyl]pyrimidin-2-amine. M.S. (M+1): 371.

Example 147

N-[(4-fluoro-1-{[(1R,2R)-2-phenylcyclopropyl]carbonyl}piperidin-4-yl)methyl]-5-methylpyrimidin-2-amine

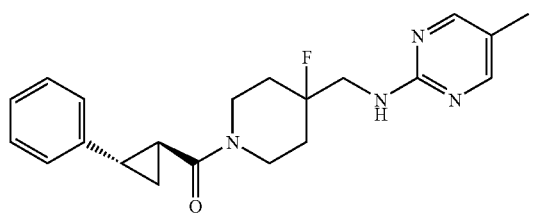

Step 1:

tert-Butyl 1-oxa-6-azaspiro[2.5]octane-6-carboxylate

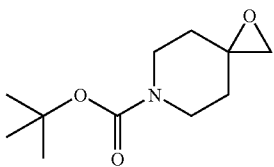

To a solution of tert-butyl 4-oxopiperidine-1-carboxylate (0.50 g, 2.51 mmol) in THF/DMF (2:1, 6 mL) at 60° C. was added trimethylsulfoxonium iodide (0.58 g, 2.63 mmol) and sodium t-butoxide (0.25 g, 2.63 mmol). The reaction mixture was stirred at 60° C. for 30 min, cooled to RT and concentrated. Water was added and the mixture was extract with EtOAc twice. The combined organics were dried over Na$_2$SO$_4$, filtered and concentrated. Purification on silica gel (3:1, hexanes:EtOAc) gave tert-butyl 1-oxa-6-azaspiro[2.5]octane-6-carboxylate as a clear oil that solidified upon standing.

Step 2:

Benzyl 4-fluoro-4-(hydroxymethyl)-piperidine-1-carboxylate

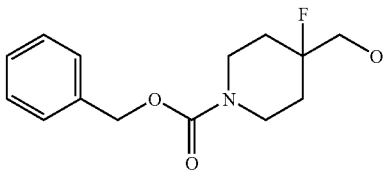

To a solution of tert-butyl 4-oxopiperidine-1-carboxylate (7.0 g, 32.8 mmol) in CH$_2$Cl$_2$ (14 mL) at −10° C. was added HF-pyridine (11.6 mL, 82.1 mmol) portionwise. The reaction mixture was stirred for 10 min at −10° C., warmed to RT. After stirring for 16 h, the reaction was quenched with aqueous NaCO$_3$, and extracted with CH$_2$Cl$_2$. The aquoues layer was concentrated to a white paste that was suspended in CH$_2$Cl$_2$ (100 mL). N-benzyloxycarbonyloxysuccinimide (8.2 g, 32.8 mmol) was added and the mixture was stirred at RT for 3 h. The reaction mixture was partitioned between EtOAc and H$_2$O, the organic layer was dried over Na$_2$SO$_4$, filtered and concentrated. Purification on silica gel (10:1 to 1:1 hexanes:EtOAc) gave benzyl 4-fluoro4-(hydroxymethyl)-piperidine-1-carboxylate as a clear oil. M.S. (M+1): 268

Step 3:

Benzyl 4-fluoro-4-{[(methylsulfonyl)oxy]methyl}piperidine-1-carboxylate

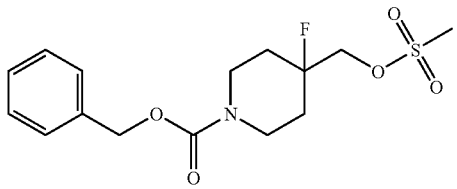

To a solution of benzyl 4-fluoro-4-(hydroxymethyl)-piperidine-1-carboxylate (1.0 g, 3.7 mmol) in $CH_2Cl_2$ (10 mL) at RT was added methanesulfonyl chloride (0.29 mL, 3.7 mmol) and triethylamine (1.04 mL, 7.5 mmol). The reaction mixture was stirred at rt for 5 min, and partitioned between ethyl acetate and water. The organic layer was dried over $Na_2SO_4$, filtered, concentrated and purified on silica gel (10:1 to 1:2 hexanes:EtOAc) to give benzyl 4-fluoro-4-{[(methylsulfonyl)oxy]methyl}piperidine-1-carboxylate. M.S. (M+1): 346

Step 4:

Benzyl 4-(azidomethyl)-4-fluoropiperidine-1-carboxylate

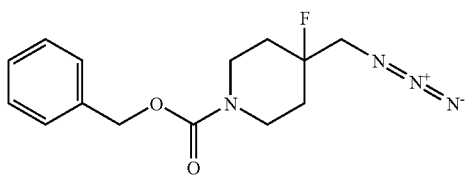

To a solution of benzyl 4-fluoro-4-{[(methylsulfonyl)oxy]methyl}piperidine-1-carboxylate (1.3 g, 3.7 mmol) in DMF (10 mL) at RT was added $NaN_3$ (2.4 g, 37.0 mmol). The reaction mixture was heated to 110° C. and stirred for 60 h, cooled and partitioned between EtOAc and $H_2O$. The organic layer was dried over $Na_2SO_4$, filtered, concentrated and purified on silica gel (10:1 to 1:2 hexanes:EtOAc) to give benzyl 4-(azidomethyl)-4-fluoropiperidine-1-carboxylate. (0.86 g, 80% yield). M.S. (M+1): 293

Step 5:

Benzyl 4-(aminomethyl)-4-fluoropiperidine-1-carboxylate

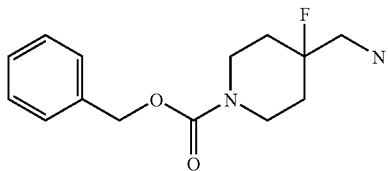

To a solution of benzyl 4-(azidomethyl)-4-fluoropiperidine-1-carboxylate (1.5 g, 5.1 mmol) in THF (10 mL) at RT was added water (0.92 mL, 0.92 mmol) and triphenylphosphine (4.3 g, 15.4 mmol). The reaction mixture was stirred for 60 h, concentrated, dissolved in HCl (1M) and extracted with Et2O four times. The aqueous layer was basified to pH 11 and extracted with EtOAc twice. The organic layer was dried over $Na_2SO_4$, filtered and concentrated. The crude mixture was chromatographed on silica gel ($CH_2Cl_2$ to 80:20:2 $CH_2Cl_2$:MeOH:NH4OH) to give benzyl 4-(aminomethyl)-4-fluoropiperidine-1-carboxylate. M.S. (M+1): 267

Step 6:

N-[(4-fluoro-1-{[(1R,2R)-2-phenylcyclopropyl]carbonyl}piperidin-4-yl)methyl]-5-methylpyrimidin-2-amine

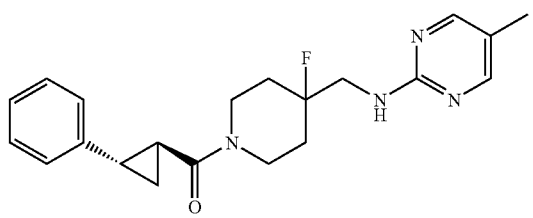

Benzyl 4-(aminomethyl)-4-fluoropiperidine-1-carboxylate was coupled to 2-chloro-5-methylpyrimidine, deprotected and coupled to (1R,2R)-2-phenylcyclopropanecarboxylic acid according to the procedure described for EXAMPLE 144, STEPS 2,3,4, providing, after chromatography, N-[(4-fluoro-1-{[(1R,2R)-2-phenylcyclopropyl]carbonyl}piperidin-4-yl)methyl]-5-methylpyrimidin-2-amine. M.S.(M+1): 369.

Example 148

4-[(4,5-Dimethyl-pyrimidin-2-ylamino)-methyl]-piperidine-1-carboxylic acid benzyl ester

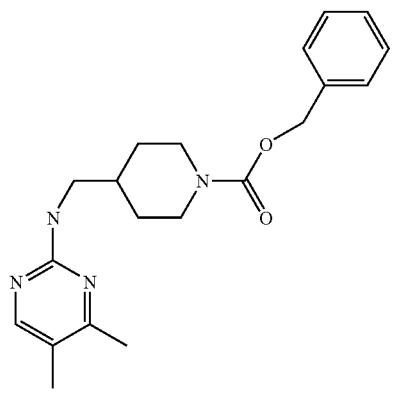

Step 1:

2-Chloro-4,5-dimethylpyrimidine

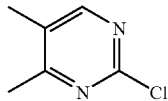

To 2-chloro-5-methylpyrimidine (EXAMPLE 144, STEP 1) (0.50 g, 0.00389 mol) in diethyl ether (12 mL) at −30° C. and under nitrogen was added dropwise 1.4M methyllithium (2.90 mL, 0.00405 mol) and the reaction allowed to stir at −30° C. for 30 min and at 0° C. for 30 min. The reaction was quenched with a solution of acetic acid (0.242 mL), water (0.039 mL, and THF (0.8 mL) and then a solution of DDQ (0.92 g, 0.00405 mol) in THF was added. The reaction was stirred 5 min at rt, recooled to 0° C. and 3N sodium hydroxide added. The reaction was allowed to stir at 0° C. for 30 min after which a thick oily precipitate formed. The organic supernatant was decanted and the residue washed with diethyl ether (2×20 mL). The organic layers were dried over sodium sulfate, filtered through a pad of silica and the silica pad washed with diethyl ether. The filtrate was concentrated in vacuo to give the title compound as an oil. M.S. (M+1): 143.

$^1$H NMR 400 MHz (δ, CDCl$_3$) δ: 2.22(s, 3H), 2.44(s, 3H), 8.27(s, 1H).

Step 2:

4-[(4,5-Dimethyl-pyrimidin-2-ylamino)-methyl]-piperidine-1-carboxylic acid benzyl ester The above compound was prepared in a manner similar to that utilized for the preparation of EXAMPLE 144, STEP 2 using 2-chloro-4,5-dimethylpyrimidine in place of 2-chloro-5-methylpyrimidine, to give the title compound. M.S.(M+1): 355.

Example 149

4-[(4,5-Dimethyl-pyrimidin-2-ylamino)-methyl]-piperidine-1-carboxylic acid 4-methyl-benzyl ester

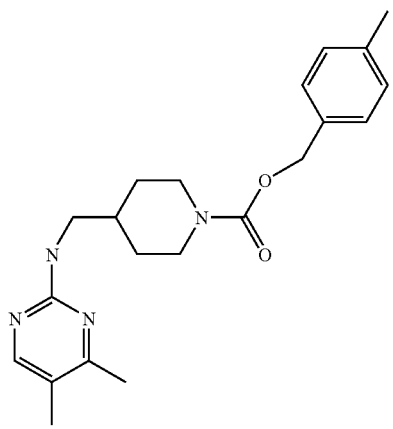

The title compound was prepared from 2-chloro-4,5-dimethylpyrimidine (EXAMPLE 148, STEP 1) and INTERMEDIATE 2A as described in a manner similar to that described in EXAMPLE 144, STEP 2 to give the title compound. M.S.(M+1): 369

The following EXAMPLES 150–152 were prepared from 4-[(4,5-dimethyl-pyrimidin-2-ylamino)-methyl]-piperidine-1-carboxylic acid benzyl ester (EXAMPLE 148) by hydrogenation of the CBZ group as described in EXAMPLE 145, STEP 1, followed by coupling with the appropriate acid as described in EXAMPLE 145, STEP 2

Example 150

Trans {4-[(4,5-Dimethyl-pyrimidin-2-ylamino)-methyl]-piperidin-1-yl}-(2-phenyl-cyclopropyl)-methanone

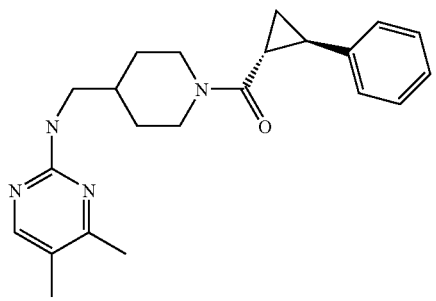

M.S.(M+1): 365.

Example 151

{4-[(4,5-Dimethyl-pyrimidin-2-ylamino)-methyl]-piperidin-1-yl}-[2-(2-fluoro-phenyl)-cyclopropyl]-methanone

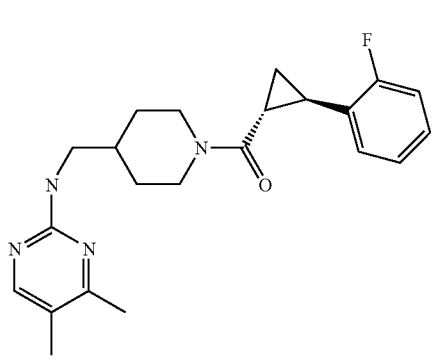

M.S.(M+1): 383.

Example 152

{4-[(4,5-Dimethyl-pyrimidin-2-ylamino)-methyl]-piperidin-1-yl}-[2-(2,6-difluoro-phenyl)-cyclopropyl]-methanone

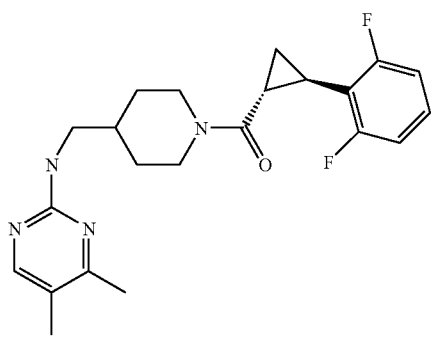

M.S.(M+1): 401.

Example 153

5-bromo-N-[(1-{[(1R,2R)-2-phenylcyclopropyl]carbonyl}piperidin-4-yl)methyl]pyrimidin-2-amine

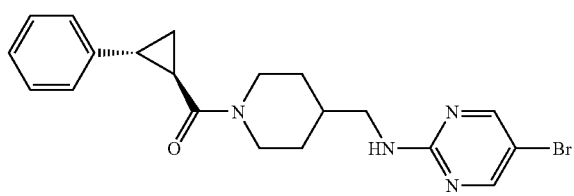

Step 1:

[1-(2-Phenyl-cyclopropanecarbonyl)-piperidin-4-ylmethyl]-carbamic acid tert-butyl ester

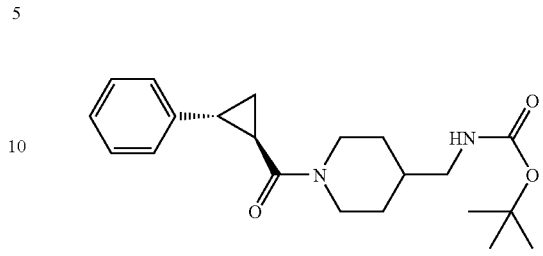

A mixture of tert-butyl piperidin-4-ylmethylcarbamate (Epsilon, 0.80 g, 3.73 mmol), (1R,2R)-2-phenylcyclopropanecarboxylic acid (T. Riley eta al, *J. Med. Chem.*, 15, 1187, 1972) (0.61 g, 3.73 mmol), EDC (1.07 g, 5.60 mmol) and HOBt (0.76 g, 5.60 mmol) in DMF (10 mL) was stirred at RT for 2 h. The reaction mixture was diluted with ethyl acetate (200 mL), washed with aq. sat. NaHCO$_3$ (50 mL), water (5×50 mL), brine (50 mL), dried over Na$_2$SO$_4$, filtered and concentrated. The residue was chromatographed on silica gel 60 (90 g), eluting with 10:1-10:89-80 CH$_2$Cl$_2$:2-propanol:hexane to give the title compound. (1.22 g, 91.0%). M.S. (M+1): 359.

Step 2:

(1-{[(1R,2R)-2-phenylcyclopropyl]carbonyl}piperidin-4-yl)methylamine

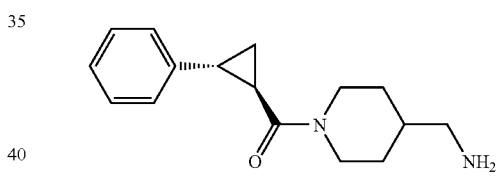

A solution of tert-butyl (1-{[(1R,2R)-2-phenylcyclopropyl]carbonyl}piperidinyl-4-yl)methylcarbamate (1.00 g, 2.79 mmol) in TFA (3 mL) and CH$_2$Cl$_2$ (3 mL) was stirred at R.T. for 0.5 h. The reaction mixture was then concentrated to give the title compound as a trifluoroacetate salt.

Step 3:

5-bromo-N-[(1-{[(1R,2R)-2-phenylcyclopropyl]carbonyl}piperidin-4-yl)methyl]pyrimidin-2-amine

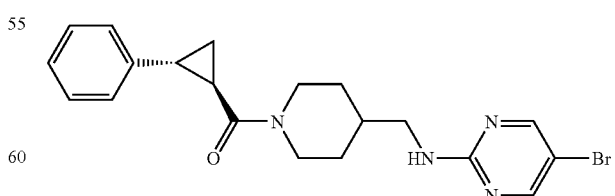

A mixture of (1-{[(1R,2R)-2-phenylcyclopropyl]carbonyl}piperidin-4-yl)methylamine trifluoroacetate salt (1.00 g, 2.69 mmol), 5-bromo-2-chloro-pyrimidine ([32779-36-5], 0.519 g, 2.69 mmol) and cesium carbonate (1.75 g, 5.37 mmol) in DMF (7 mL) was heated at 100° C. for 1.5 h. The reaction mixture was cooled to RT, diluted with ethyl acetate (200 mL), washed with water (5×20 mL), and brine (10 mL), then dried over $Na_2SO_4$, filtered and concentrated. The residue was chromatographed on silica gel 60, eluting with 10:1-20:89-70 $CH_2Cl_2$:2-propanol:hexane to give the title compound. (0.31 g, 28.1%). M.S. (M+1): 416.

$^1$H NMR (400 MHz, $CDCl_3$): δ 8.26 (s, 2H, Pyr), 7.28 (t, J=7.3 Hz, 2 H, Ar), 7.19 (t, J=7.7 Hz, 1H, Ar), 7.11 (d, J=7.6 Hz, 2H, Ar), 5.21 (s, 1H, NH), 4.64 (d, J=11.9 Hz, 1H, $NCH_2$), 4.13 (d, J=12.9 Hz, 1H, $NCH_2$), 3.31 (s, 2H, $NHCH_2$), 3.05 (q, J=12.6 Hz, 1H, $NCH_2$), 2.62 (t, J=12.3 Hz, 1H, $NCH_2$), 2.46 (brs, 1H, ArCH), 1.98 (m, 1H, CHCO), 1.87 (m, 1H, $CH_2CHCH_2$), 1.80 (d, J=13.1 Hz, 2H, $CHCH_2CH_2$), 1.65 (s, 1H, $CHCH_2CH$), 1.25 (s, 1H, $CHCH_2CH$), 1.21 (m, 2 H, $CHCH_2CH_2$).

Example 154

N-[(1-{[(1R,2R)-2-Phenylcyclopropyl] carbonyl}piperidin-4-yl)methyl]-5-[(trimethylsilyl) ethynyl]pyrimidin-2-amine

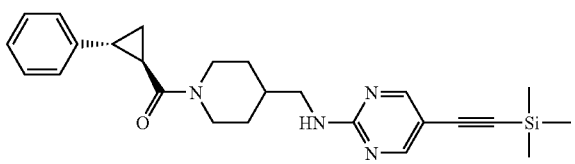

A mixture of 5-bromo-N-[(1-{[(1R,2R)-2-phenylcyclopropyl]carbonyl}piperidin-4-yl)methyl]pyrimidin-2-amine (EXAMPLE 153) (0.300 g, 0.722 mmol), trimethylsilylacetylene (0.177 g, 1.81 mmol), $Pd(PPh_3)_4$ (0.083 g, 0.072 mmol), and copper iodide (0.007 g, 0.036 mmol) in DMSO (1 mL) and diethylamine (1 mL) was heated in a sealed tube at 100° C. for 3 h. The reaction mixture was cooled to RT, diluted with ethyl acetate (50 mL), washed with water (10 mL), and brine (10 mL), then dried over $Na_2SO_4$, filtered and concentrated. The residue was chromatographed on silica gel 60 (35 g), eluting with 10:1-10:89-80 $CH_2Cl_2$:2-propanol:hexane to give the title compound.

Example 155

5-Ethynyl-N-[(1-{[(1R,2R)-2-phenylcyclopropyl] carbonyl}piperidin-4-yl)methyl]pyrimidin-2-amine

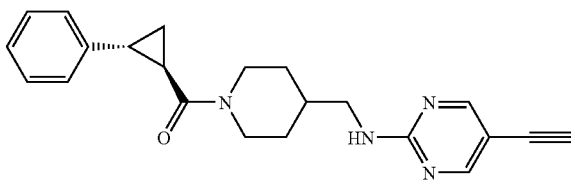

A mixture of N-[(1-{[(1R,2R)-2-phenylcyclopropyl] carbonyl}piperidin-4-yl)methyl]-5-[(trimethylsilyl)ethynyl] pyrimidin-2-amine (EXAMPLE 154) (0.200 g, 0.462 mmol) and potassium carbonate (0.128 g, 0.924 mmol) in methanol (3 mL) was stirred at RT for 0.5 h. The reaction mixture was concentrated in vacuo, diluted with ethyl acetate (50 mL), washed with water (20 mL), and brine (10 mL), then dried over $Na_2SO_4$, filtered and concentrated. The residue was chromatographed on silica gel 60 (35 g), eluting with 10:1-20:89-70 $CH_2Cl_2$:2-propanol:hexane to give the title compound. M.S. (M+1): 361.

$^1$H NMR (400 MHz, $CDCl_3$): δ 8.37 (s, 2H, Pyr), 7.28 (t, J=7.1 Hz, 2 H, Ar), 7.19 (t, J=7.0 Hz, 1H, Ar), 7.11 (d, J=7.4 Hz, 2H, Ar), 5.38 (s, 1H, NH), 4.65 (d, J=12.6 Hz, 1H, $NCH_2$), 4.14 (d, J=14.1 Hz, 1H, $NCH_2$), 3.36 (m, 2H, $NHCH_2$), 3.17 (s, 1H, CCH), 3.05 (q, J=12.2 Hz, 1H, $NCH_2$), 2.62 (t, J=12.5 Hz, 1H, $NCH_2$), 2.46 (brs, 1H, ArCH), 1.97 (m, 1H, CHCO), 1.86 (m, 1H, $CH_2CHCH_2$), 1.80 (d, J=12.5 Hz, 2H, $CHCH_2CH_2$), 1.65 (m, 1H, $CHCH_2CH$), 1.26 (m, 1H, $CHCH_2CH$), 1.23 (m, 2H, $CHCH_2CH_2$).

Example 156

2-{[(1-{[(1R,2R)-2-phenylcyclopropyl] carbonyl}piperidin-4-yl)methyl]amino}pyrimidine-5-carbonitrile

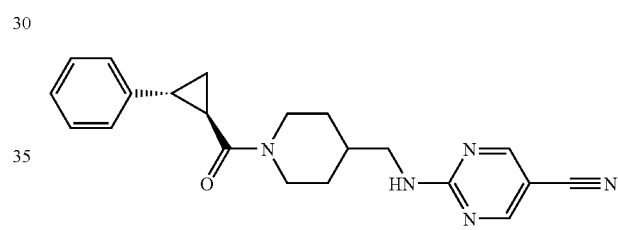

Step 1:

4-chloro-2-(methylthio)pyrimidine-5-carbonitrile

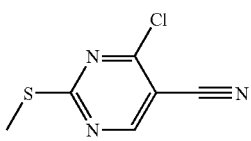

A stirred solution of 4-hydroxy-2-(methylthio)pyrimidine-5-carbonitrile (British patent GB901749) (1.00 g, 5.98 mmol) in $POCl_3$ (5 mL) was heated to reflux for 2 h. The reaction mixture was concentrated in vacuo and the residue quenched with ice (100 g). The solution was then basified to pH 8 with sat. aq $NaHCO_3$ and extracted with ethyl acetate (3×50 mL). The combined ethyl acetate layers were washed with water (20 mL), brine (10 mL), dried over $Na_2SO_4$, filtered and concentrated to give the title compound.

$^1$H NMR (400 MHz, $CD_3OD$): δ 8.84 (s, 1H, Ar), 2.62 (s, 3H, $CH_3$)

Step 2:

2-(Methylthio)pyrimidine-5-carbonitrile

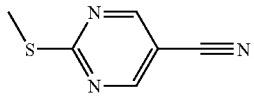

To a stirred mixture of 4-chloro-2-(methylthio)pyrimidine-5-carbonitrile (0.843 g, 4.54 mmol) and zinc dust (1.48 g, 22.71 mmol) in ethanol (7.5 mL) and water (1.4 mL) was slowly added acetic acid (0.29 mL, 5.13 mmol). The resulting reaction mixture was vigorously stirred for 3 h. The solids were removed by filtration and the filtrate concentrated in vacuo. The residue was chromatographed on silica gel 60 (35 g), eluting with 10:1-20:89-70 $CH_2Cl_2$:2-propanol:hexane to give the title compound. M.S. (M+1): 152.

$^1$H NMR (400 MHz, $CDCl_3$): δ 8.72 (s, 2H, Ar), 2.61 (s, 3H, $CH_3$).

Step 3:

2-{[(1-{[(1R,2R)-2-Phenylcyclopropyl]carbonyl}piperidin-4-yl)methyl]amino}pyrimidine-5-carbonitrile

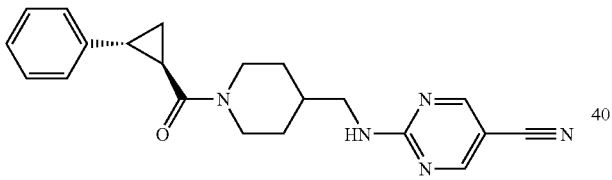

A mixture of (1-{[(1R,2R)-2-phenylcyclopropyl]carbonyl}piperidin-4-yl)methylamine (EXAMPLE 153, STEP 2) (0.100 g, 0.387 mmol), 2-(methylthio)pyrimidine-5-carbonitrile (0.059 g, 0.387 mmol) and cesium carbonate (0.252 g, 0.774 mmol) in DMF (1 mL) was heated at 70° C. for 1 h. The reaction mixture was cooled to RT, diluted with ethyl acetate (50 mL), washed with water (5×10 mL), and brine (10 mL), then dried over $Na_2SO_4$, filtered and concentrated. The residue was chromatographed on a reversed phase column, running 5–95% 0.1% TFA in $CH_3CN$/0.1% TFA in water to give the title compound as a TFA salt. M.S. (M+1): 362.

$^1$H NMR (400 MHz, $CDCl_3$): δ 8.52 (s, 1H, Pyr), 8.45 (s, 1H, Pyr), 7.28 (t, J=7.9 Hz, 2H, Ar), 7.20 (t, J=6.6 Hz, 1H, Ar), 7.11 (d, J=7.3 Hz, 2H, Ar), 5.78 (s, 1H, NH), 4.66 (d, J=12.2 Hz, 1H, $NCH_2$), 4.15 (d, J=13.1 Hz, 1H, $NCH_2$), 3.41 (m, 2H, $NHCH_2$), 3.06 (q, J=12.4 Hz, 1H, $NCH_2$), 2.62 (t, J=12.7 Hz, 1H, $NCH_2$), 2.47 (brs, 1H, ArCH), 1.96 (m, 1H, CHCO), 1.91 (m, 1H, $CH_2CHCH_2$), 1.80 (d, J=13.2 Hz, 2H, $CHCH_2CH_2$), 1.65 (s, 1H, $CHCH_2CH$), 1.27 (s, 1H, $CHCH_2CH$), 1.25 (m, 2H, $CHCH_2CH_2$).

Example 157

5-Ethyl-N-[(1-{[(1R,2R)-2-phenylcyclopropyl]carbonyl}piperidin-4-yl)methyl]pyrimidin-2-amine

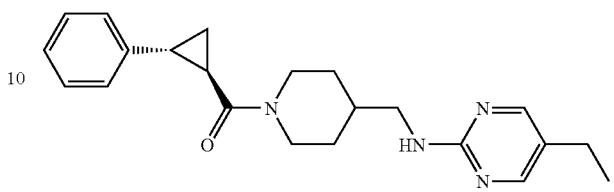

The stirred reaction mixture of (1-{[(1R,2R)-2-phenylcyclopropyl]carbonyl}piperidin-4-yl)methylamine (EXAMPLE 154, STEP 2) (0.100 g, 0.387 mmol), 2-chloro-5-ethyl-pyrimidine ([111196-81-7], 0.055 g, 0.387 mmol) and cesium carbonate (0.252 g, 0.774 mmol) in DMF (5 mL) was heated at 150° C. for 7 h. The reaction mixture was cooled to RT, diluted with ethyl acetate (100 mL), washed with water (5×20 mL), and brine (10 mL), then dried over $Na_2SO_4$, filtered and concentrated. The residue was chromatographed on silica gel 60, eluting with 10:1-20:89-70 $CH_2Cl_2$:2-propanol:hexane to give the title compound. M.S. (M+1): 365.

$^1$H NMR (400 MHz, $CDCl_3$): δ 8.13 (s, 2H, Pyr), 7.28 (t, J=6.6 Hz, 2 H, Ar), 7.19 (t, J=7.2 Hz, 1H, Ar), 7.11 (d, J=7.3 Hz, 2H, Ar), 5.05 (s, 1H, NH), 4.64 (d, J=12.9 Hz, 1H, $NCH_2$), 4.14(d, J=12.8 Hz, 1H, $NCH_2$), 3.32 (s, 2H, $NHCH_2$), 3.05 (q, J=12.5 Hz, 1H, $NCH_2$), 2.62 (t, J=12.6 Hz, 1H, $NCH_2$), 2.46 (q, J=7.5 Hz, 2H, $CH_2CH_3$), 2.43 (brs, 1H, ArCH), 1.97 (m, 1H, CHCO), 1.86 (m, 1 H, $CH_2CHCH_2$), 1.82 (d, J=13.5 Hz, 2H, $CHCH_2CH_2$), 1.64 (m, 1H, $CHCH_2CH$), 1.26 (m, 1H, $CHCH_2CH$), 1.22 (m, 2H, $CHCH_2CH_2$), 1.19 (t, J=7.6 Hz, 3H, $CH_3CH_2$), Example 158

5-(Cyclopropylethynyl)-N-[(1-{[(1R,2R)-2-phenylcyclopropyl]carbonyl}-piperidin-4-yl)methyl]pyrimidin-2-amine

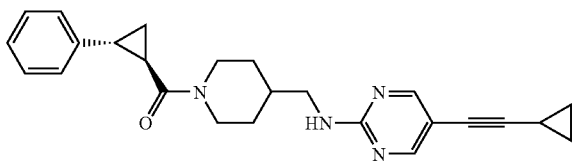

A mixture of 5-bromo-N-[(1-{[(1R,2R)-2-phenylcyclopropyl]carbonyl}piperidin-4-yl)methyl]pyrimidin-2-amine (EXAMPLE 153) (0.050 g, 0.120 mmol), ethynylcyclopropane (0.020 g, 0.301 mmol), Pd(PPh$_3$)$_4$ (0.014 g, 0.012 mmol), copper iodide (0.001 g, 0.006 mmol) in DMSO (1 mL) and diethylamine (1 mL) was heated in a sealed tube at 100° C. for 3 h. The reaction mixture was cooled to RT, diluted with ethyl acetate (50 mL), washed with water (10 mL), and brine (10 mL), then dried over $Na_2SO_4$, filtered and concentrated. The residue was chromatographed on a reverse phase column, running 5–95% 0.1% TFA in $CH_3CN$/0.1% TFA in water to give the title compound as a TFA salt. M.S. (M+1): 401.

¹H NMR (400 MHz, CDCl₃): δ 8.56 (s, 1H, Pyr), 8.02 (s, 1H, Pyr), 7.28 (t, J=7.4 Hz, 2H, Ar), 7.20 (t, J=7.2 Hz, 1H, Ar), 7.11 (d, J=7.5 Hz, 2H, Ar), 4.64 (d, J=13.0 Hz, 1H, NCH₂), 4.15 (d, J=11.7 Hz, 1H, NCH₂), 3.50 (s, 1H, NHCH₂), 3.41 (s, 1H, NHCH₂), 3.07 (q, J=12.8 Hz, 1H, NCH₂), 2.64 (t, J=12.7 Hz, 1H, NCH₂), 2.47 (brs, 1H, ArCH), 1.98 (m, 1H, CHCO), 1.92 (m, 1H, CH₂CHCH₂), 1.79 (d, J=13.6 Hz, 2H, CHCH₂CH₂), 1.64 (s, 1H, CHCH₂CH), 1.44 (m, 1H, CCCH), 1.28 (m, 1H, CHCH₂CH), 1.26 (m, 2H, CHCH₂CH₂), 0.83 (m, 4 H, CH₂).

Example 159

N-[(1-{[(1R,2R)-2-Phenylcyclopropyl]carbonyl}piperidin-4-yl)methyl]-5-(phenylethynyl)pyrimidin-2-amine

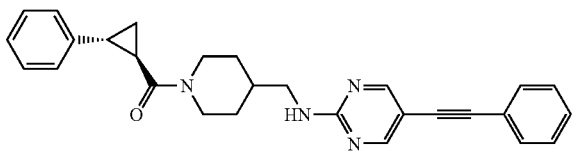

A mixture of 5-bromo-N-[(1-{[(1R,2R)-2-phenylcyclopropyl]carbonyl}piperidin-4-yl)methyl]pyrimidin-2-amine (EXAMPLE 153) (0.200 g, 0.482 mmol), ethynylbenzene (0.123 g, 0.132 mmol), Pd(PPh₃)₄ (0.056 g, 0.048 mmol), and copper iodide (0.005 g, 0.024 mmol) in DMSO (1 mL) and diethylamine (1 mL) was heated in a sealed tube at 100° C. for 3 h. The reaction mixture was cooled to RT, diluted with ethyl acetate (50 mL), washed with water (10 mL), and brine (10 mL), then dried over Na₂SO₄, filtered and concentrated. The residue was chromatographed on a reversed phase column, running 5–95% 0.1% TFA in CH₃CN/0.1% TFA in water to give the title compound as a TFA salt. M.S. (M+1): 437.

¹H NMR (400 MHz, CDCl₃): δ 8.50 (brs, 2H, Pyr), 7.50 (m, 2H, Ar), 7.38 (m, 3H, Ar), 7.28 (t, J=7.9 Hz, 2H, Ar), 7.20 (t, J=7.3 Hz, 1H, Ar), 7.11 (d, J=7.5 Hz, 2H, Ar), 4.66 (d, J=11.7 Hz, 1H, NCH₂), 4.16 (d, J=13.2 Hz, 1H, NCH₂), 3.46 (m, 2H, NHCH₂), 3.10 (m, 1H, NCH₂), 2.64 (t, J=11.9 Hz, 1H, NCH₂), 2.47 (brs, 1H, ArCH), 1.97 (m, 1H, CHCO), 1.93 (m, 1H, CH₂CHCH₂), 1.81 (d, J=11.5 Hz, 2H, CHCH₂CH₂), 1.65 (brs, 1H, CHCH₂CH), 1.28 (m, 1H, CHCH₂CH), 1.25 (m, 2H, CHCH₂CH₂).

Example 160 to Example 180

The following examples were prepared by coupling the appropriate amine (EXAMPLE 143, STEP 1, EXAMPLE 145, STEP 1, or piperidin-4-ylmethyl-pyrimidin-2-yl-amine which was prepared in a manner similar to that described for EXAMPLE 143, STEP 1, replacing 2-chloro-5-methylpyrimidine with 2-chloropyrimidine in STEP 1) with the appropriately substituted trans phenylcyclopropanecarboxylic acid (prepared in a similar manner to that described in (EXAMPLE 136).

| EX. | Structure | Name | M.S. (M + 1) |
|---|---|---|---|
| 160 | 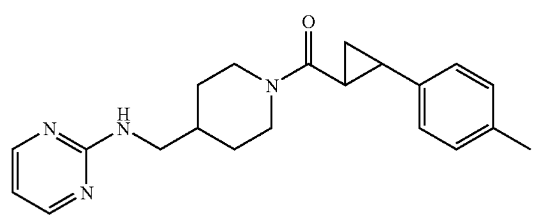 | [4-(Pyrimidin-2-ylaminomethyl)-piperidin-1-yl]-(2-p-tolyl-cyclopropyl)-methanone | 351.2 |
| 161 | 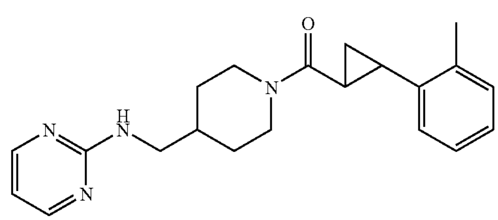 | [4-(Pyrimidin-2-ylaminomethyl)-piperidin-1-yl]-(2-o-tolyl-cyclopropyl)-methanone | 351.4 |
| 162 | 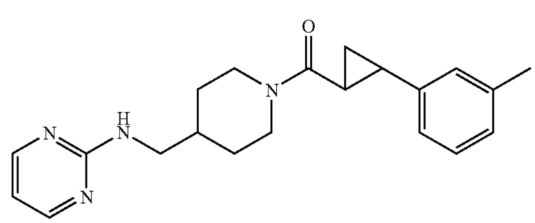 | [4-(Pyrimidin-2-ylaminomethyl)-piperidin-1-yl]-(2-m-tolyl-cyclopropyl)-methanone | 351.4 |

| EX. | Structure | Name | M.S. (M + 1) |
|---|---|---|---|
| 163 | 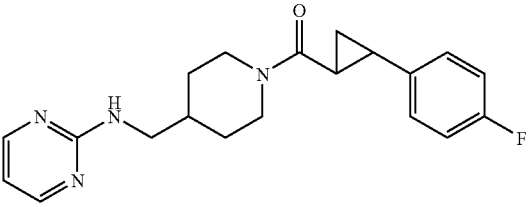 | [2-(4-Fluoro-phenyl)-cyclopropyl]-[4-(pyrimidin-2-ylaminomethyl)-piperidin-1-yl]-methanone | 355.2 |
| 164 | 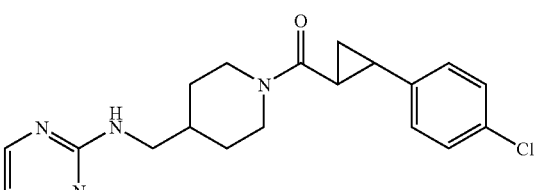 | [2-(4-Chloro-phenyl)-cyclopropyl]-[4-(pyrimidin-2-ylaminomethyl)-piperidin-1-yl]-methanone | 371.1 |
| 165 | 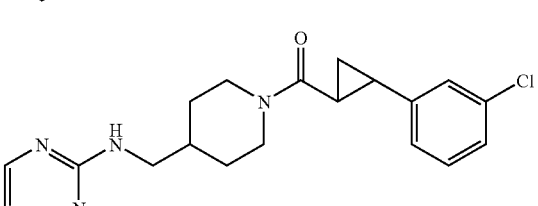 | [2-(3-Chloro-phenyl)-cyclopropyl]-[4-(pyrimidin-2-ylaminomethyl)-piperidin-1-yl]-methanone | 371.3 |
| 166 | 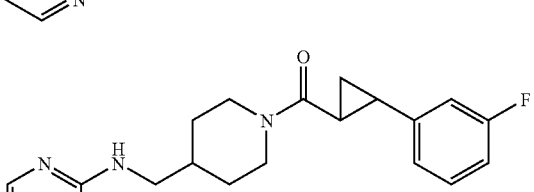 | [2-(3-Fluoro-phenyl)-cyclopropyl]-[4-(pyrimidin-2-ylaminomethyl)-piperidin-1-yl]-methanone | 355.3 |
| 167 | 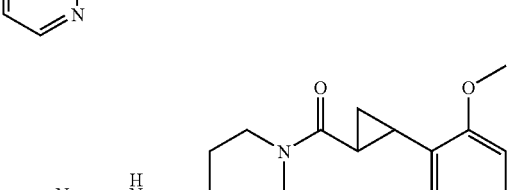 | [2-(2-Methoxy-phenyl)-cyclopropyl]-[4-(pyrimidin-2-ylaminomethyl)-piperidin-1-yl]-methanone | 367.3 |
| 168 | 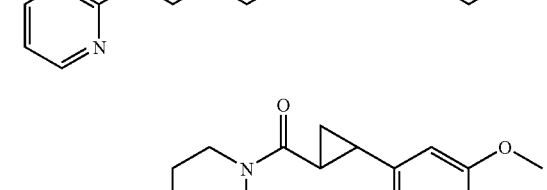 | [2-(3-Methoxy-phenyl)-cyclopropyl]-[4-(pyrimidin-2-ylaminomethyl)-piperidin-1-yl]-methanone | 367.3 |
| 169 | 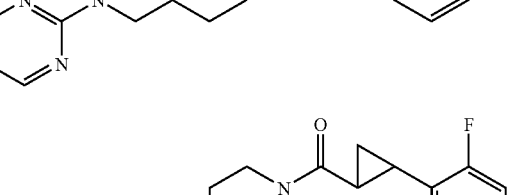 | [2-(2,6-Difluoro-phenyl)-cyclopropyl]-[4-(pyrimidin-2-ylaminomethyl)-piperidin-1-yl]-methanone | 373.3 |

-continued

| EX. | Structure | Name | M.S. (M + 1) |
|---|---|---|---|
| 170 | 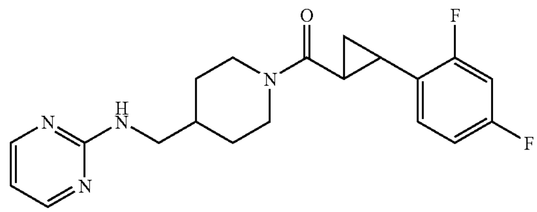 | [2-(2,4-Difluoro-phenyl)-cyclopropyl]-[4-(pyrimidin-2-ylaminomethyl)-piperidin-1-yl]-methanone | 373.4 |
| 171 | 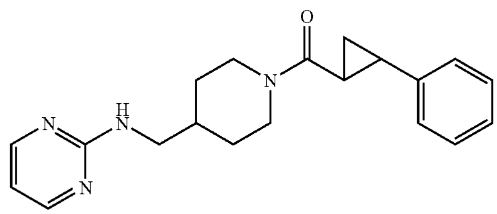 | (2-Phenyl-cyclopropyl)-[4-(pyrimidin-2-ylaminomethyl)-piperidin-1-yl]-methanone | 337.2 |
| 172 | 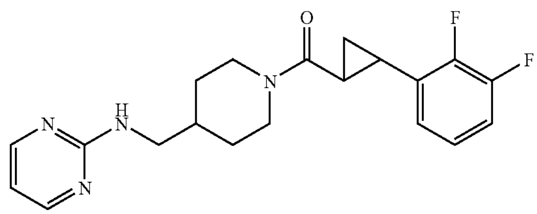 | [2-(2,3-Difluoro-phenyl)-cyclopropyl]-[4-(pyrimidin-2-ylaminomethyl)-piperidin-1-yl]-methanone | 373.3 |
| 173 | 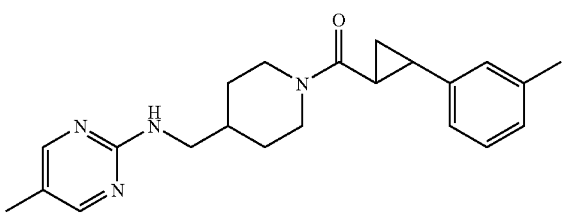 | {4-[(5-Methyl-pyrimidin-2-ylamino)-methyl]-piperidin-1-yl}-(2-m-tolyl-cyclopropyl)-methanone | 365.4 |
| 174 | 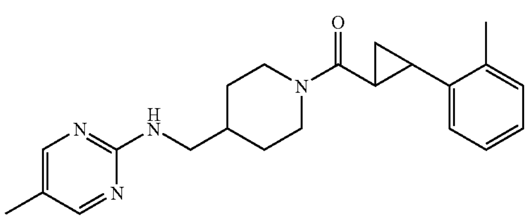 | {4-[(5-Methyl-pyrimidin-2-ylamino)-methyl]-piperidin-1-yl }-(2-o-tolyl-cyclopropyl)-methanone | 365.3 |
| 175 | 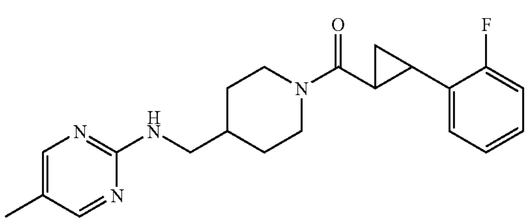 | [2-(2-Fluoro-phenyl)-cyclopropyl]-{4-[(5-methyl-pyrimidin-2-ylamino)-methyl]-piperidin-1-yl}-methanone | 369.3 |
| 176 | 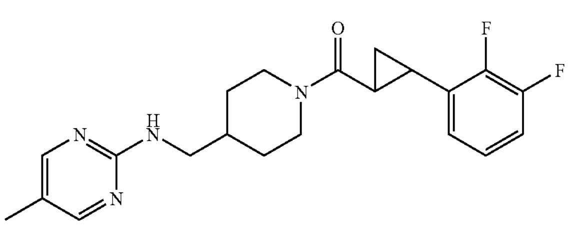 | [2-(2,3-Difluoro-phenyl)-cyclopropyl]-{4-[(5-methyl-pyrimidin-2-ylamino)-methyl]-piperidin-1-yl}-methanone | 387.3 |

| EX. | Structure | Name | M.S. (M + 1) |
|---|---|---|---|
| 177 | 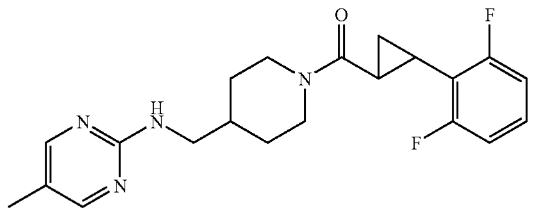 | [2-(2,6-Difluoro-phenyl)-cyclopropyl]-{4-[(5-methyl-pyrimidin-2-ylamino)-methyl]-piperidin-1-yl}-methanone | 387.3 |
| 178 | 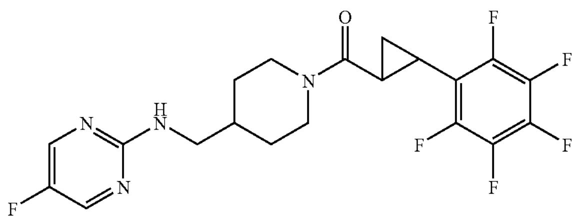 | {4-[(5-Fluoro-pyrimidin-2-ylamino)-methyl]-piperidin-1-yl}-(2-pentafluorophenyl-cyclopropyl)-methanone | 445.3 |
| 179 | 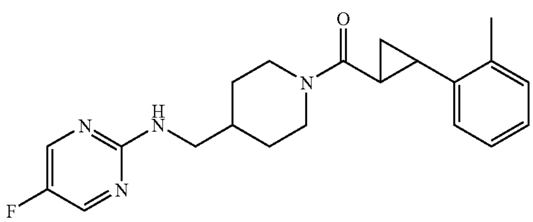 | {4-[(5-Fluoro-pyrimidin-2-ylamino)-methyl]-piperidin-1-yl}-(2-o-tolyl-cyclopropyl)-methanone | 369.3 |
| 180 | 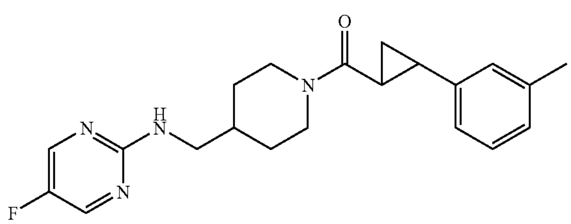 | {4-[(5-Fluoro-pyrimidin-2-ylamino)-methyl]-piperidin-1-yl}-(2-m-tolyl-cyclopropyl)-methanone | 369.4 |

Example 181

4-[(3-Fluoro-pyridin-2-ylamino)-methyl]-piperidine-1-carboxylic acid benzyl ester

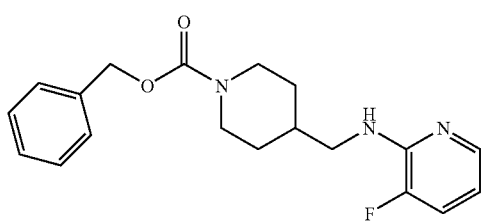

A solution of 2-chloro-3-fluoropyridine (prepared in a manner similar to that described by W. J. Link, R. F. Borne and F. L. Setliff, *J. Heterocyclic Chem.* 4, 641–3, 1967) (131 mg 1 mmol), benzyl 4-(aminomethyl)-piperidine-1-carboxylate (EXAMPLE 13, STEP 1) (248 mg, 1 mol) and diisopropylethylamine (129 mg, 1 mmol) were heated to reflux in 2-methoxyethanol for 2 days under nitrogen. The reaction mixture was concentrated, partitioned between ethyl acetate and water, the organic layer washed with brine, dried over anhydrous sodium sulfate and solvent evaporated to give the crude product purified by chromatography on silica. M.S. (M+1): 344.3

Example 182

{[(3-Fluoro-pyridin-2-ylamino)-methyl]-piperidin-1-yl}-(2-phenyl-cyclopropyl)-methanone

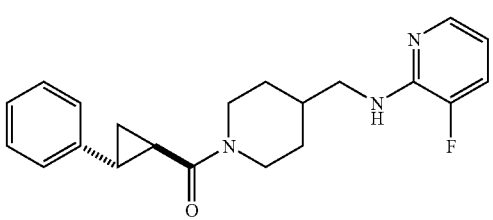

The title compound was prepared from 4-[(3-fluoro-pyridin-2-ylamino)-methyl]-piperidine-1-carboxylic acid benzyl ester (EXAMPLE 181) In a similar manner to that described in EXAMPLE 145). M.S. (M+1): 354.3

Example 183

4-[(3-Fluoro-pyridin-2-ylamino)-methyl]-piperidine-1-carboxylic acid benzyl ester

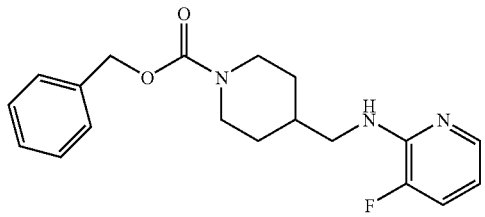

Step 1:

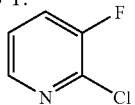

2-Chloro-3-fluoropyridine

Prepared in a manner similar to that described by W. J. Link, R. F. Borne and F. L. Setliff, *J. Heterocyclic Chem.* 4, 641–3, (1967).

Step 2:

A mixture of 2 mmol of 4-aminomethyl-piperidine-1-carboxylic acid benzyl ester, 1 mmol of 2-chloro-3-fluoropyridine, and 1 mmol of tributylamine were heated to reflux in 2 mL of cyclohexanol for 3 days (or 2-methoxyethanol for 14 days) under nitrogen. Preparative TLC eluting with 75:25 ether:hexane gave 4-[(3-fluoro-pyridin-2-ylamino)-methyl]-piperidine-1-carboxylic acid benzyl ester:

$^1$H NMR (CDCl$_3$) δ7.85 (1H, d,), 7.4–7.35 (5H, m), 7.1 (1H, dd), 6.5 (1H, m), 5.15 (2H, s), 4.65 (1H, br m), 4.2 (2H, br s), 3.4 (2H, br m), 2.8 (2H, br m), 1.8 (3H, m), 1.2 (2H, m). Mass spec.: 344.32 (M+1).

A lower band gave 4-[(2-chloro-pyridin-3-ylamino)-methyl]-piperidine-1-carboxylic acid benzyl ester:

$^1$H NMR (CDCl$_3$) δ7.7 (1H, d,), 7.4–7.35 (5H, m), 7.1 (1H, dd), 6.82 (1H, d), 5.15 (2H, s), 4.4 (1H, br m), 4.2 (2H, br s), 3.05 (2H, m), 2.8 (2H, br m), 1.8 (3H, m), 1.2 (2H, m). Mass spec.: 360.29 (M+1).

Alternatively, the use of 2,3-difluorpyridine [Finger, G. C.; Starr, L. D.; Roe, A.; Link, W. J., J. Organic Chem. 27, 3965–68, 1962.] in place of 2-chloro3-fluoropyridine in refluxing 2-butanol gave higher yields of product without the 4-[(2-chloro-pyridin-3-ylamino)-methyl]-piperidine-1-carboxylic acid benzyl ester by-product.

Example 184

[R,R]{4-[(3-Fluoro-pyridin-2-ylamino)-methyl]-piperidin-1-yl}-(2-phenyl-cyclopropyl)-methanone

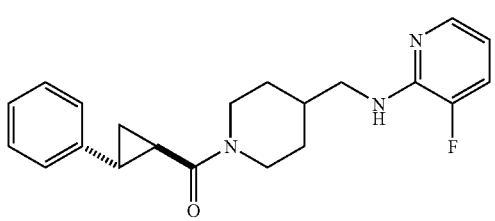

Prepared from 4-[(3-fluoro-pyridin-2-ylamino)-methyl]-piperidine-1-carboxylic acid benzyl ester by hydrogenolysis of the benzyloxycarbonyl group followed by EDC, HOBt coupling with [R,R] trans-2-phenyl-1-cyclopropanecarboxylic acid in DMF in the usual manner such as described previously in EXAMPLE 143 above:

$^1$H NMR (CDCl$_3$) δ7.85 (1H, d,), 7.35 (2H, m), 7.2 (1H, dd), 7.1 (3H, m), 6.5 (1H, m), 4.65 (2H, br m), 4.18 (1H, br d), 3.4 (2H, br m), 3.1 (1H, complex m), 2.6 (1H, m), 2.45 (1H, m), 2.0–1.8 (4H, m), 1.62 (1H, m), 1.2 (3H, m). Mass spec.: 354.35 (M+1).

Example 185

4-[(4-Methyl-pyrimidin-2-ylamino)-methyl]-piperidine-1-carboxylic acid benzyl ester

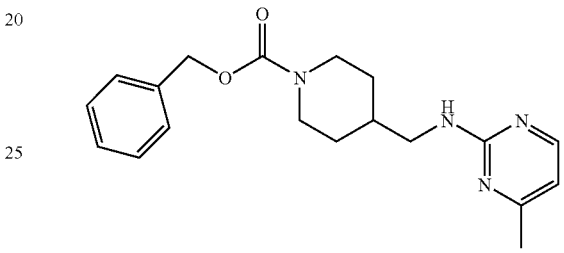

A mixture of 1.6 mmol of 4-aminomethyl-piperidine-1-carboxylic acid benzyl ester, 2.4 mmol of 2-methanesulfonyl-4-methylpyrimidine, and 3 mmol of N,N,-diethylethylamine were heated to reflux in either 5 mL of 2-butanol for 24 h under nitrogen. Preparative TLC eluting with ethyl acetate gave 460 mg of 4-[(3-fluoro-pyridin-2-ylamino)-methyl]-piperidine-1-carboxylic acid benzyl ester:

$^1$H NMR (CDCl$_3$) δ 8.1 (1H, d,), 7.4–7.35 (5H, m), 6.4 (1H, d), 5.15 (2H, s), 4.2 (2H, br s), 3.35 (2H, m), 2.8 (2H, br m), 2.3 (3H, s), 1.8 (4H, m), 1.2 (2H, m). Mass spec.: 341.4 (M+1).

Example 186

[R,R]{4-[(4-Methyl-pyrimidin-2-ylamino)-methyl]-piperidin-1-yl}-(2-phenyl-cyclopropyl)-methanone

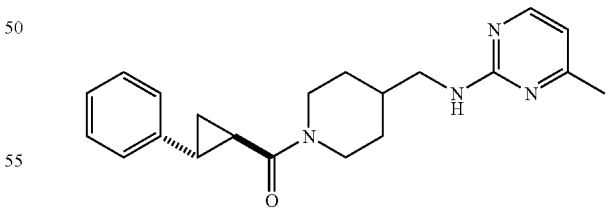

Prepared from 4-[(4-methyl-pyrimidin-2-ylamino)-methyl]-piperidine-1-carboxylic acid benzyl ester by hydrogenolysis of the benzyloxycarbonyl group followed by EDC, HOBt coupling with [R,R] trans-2-phenyl-1-cyclopropanecarboxylic acid in DMF as described above in EXAMPLE 143. Preparative TLC using 90:10 ethyl acetate: methanol gave the product:

$^1$H NMR (CDCl$_3$) δ 8.1 (1H, d,), 7.35 (2H, m), 7.2 (1H, dd), 7.1 (2H, m), 6.4 (1H, d), 5.3 (1H, br m), 4.6 (1H, br d), 4.15 (1H, br d), 3.35 (2H, m), 3.05 (1H, dd), 2.6 (1H, t), 2.45 (1H, m), 2.3 (3H, s), 2.0 (1H, m), 1.8 (4H, m), 1.6 (1H, s), 1.2 (4H, m). Mass spec.: 351.4 (M+1).

Example 187

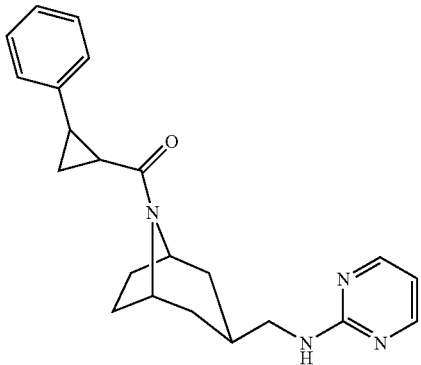

(+−)-N-({8-[(trans-2-phenylcyclopropyl)carbonyl]-8-aza-bicyclo[3.2.1]oct-3-exo-yl}methyl)pyrimidin-2-amine was prepared similarly as described previously above.

$^1$H NMR (CDCl$_3$) δ8.25 (2H, m), 7.28 (2H, m), 7.19 (1H, m), 7.11 (2H, m), 6.52 (1H, m), 5.13 (1H, m), 4.71 (1H, br s), 4.39 (1H, br s), 3.32 (2H, m), 2.51 (1H, m), 2.23 (1H, m), 2.05–1.88 (3H, m), 1.80–1.32 (7H, m), 1.25 (1H, m).

Mass spec.: 363.4 (M+1).

What is claimed is:

1. A compound having the formula (I):

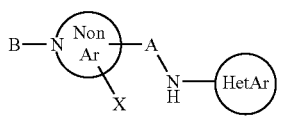

or pharmaceutically acceptable salts thereof, wherein
NonAr is an 8-azabicyclo[3.2.1]octane ring;
HetAr is a 5 or 6 membered heteroaromatic ring containing 1–3 nitrogen ring atoms, or isoxazolyl, thiazolyl, thiadiazolyl, quinolinyl, quinazolinyl, purinyl, pteridinyl, benzimidazolyl, pyrrolopyrimidinyl, or imidazopyridinyl;
HetAr is optionally substituted with 1 or 2 substituents, each substituent independently is C$_{1-4}$alkyl, C$_{1-4}$alkoxy, C$_{2-4}$alkynyl, trifluoromethyl, hydroxy, hydroxyC$_{1-4}$alkyl, fluoro, chloro, bromo, iodo, cyano, methylsulfanyl, cyclopropylethynyl-, phenylethynyl-, heteroarylethynyl-, —N(C$_{0-4}$alkyl)(C$_{0-4}$alkyl), nitro, (C$_{1-2}$alkyl)(C$_{1-2}$alkyl)NCH$_2$—, (C$_{1-2}$alkyl)HNCH$_2$—, Si(CH$_3$)$_3$—C—, or NH$_2$C(O)—;

A is CH$_2$—;
B is aryl(CH$_2$)$_{0-3}$—O—C(O)—, heteroaryl(CH$_2$)$_{1-3}$—O—C(O)—, indenyl(CH$_2$)$_{0-3}$—O—C(O)—, aryl(CH$_2$)$_{1-3}$—C(O)—, aryl-cyclopropyl-C(O)—, heteroaryl-cyclopropyl-C(O)—, heteroaryl(CH$_2$)$_{1-3}$—C(O)—, aryl(CH$_2$)$_{1-3}$—, heteroaryl(CH$_2$)$_{1-3}$—, aryl(CH$_2$)$_{1-3}$—NH—C(O)—, aryl(CH$_2$)$_{1-3}$—NH—C(NCN)—, aryl(CH$_2$)$_{1-3}$—SO$_2$—, heteroaryl(CH$_2$)$_{1-3}$—SO$_2$—, wherein any of the aryl or heteroaryl is optionally substituted by 1–5 substitutents, each substituent independently is C$_{1-4}$alkyl, C$_{3-6}$cycloalkyl, C$_{1-4}$alkoxy, trifluoromethyl, bromo, fluoro, or chloro; and
X is H, OH, F, C$_{1-4}$alkyl, C$_{1-4}$alkoxy, NH$_2$, or X taken with an adjacent bond is =O.

2. The compound according to claim 1, or pharmaceutically acceptable salts thereof, wherein
NonAr is an 8-azabicyclo[3.2.1]octane ring; and
B is aryl(CH$_2$)$_{0-3}$—O—C(O)—, wherein the aryl is optionally substituted by 1–5 substitutents, each substituent independently is C$_{1-4}$alkyl, C$_{3-6}$-cycloalkyl, C$_{1-4}$alkoxy, trifluoromethyl, bromo, fluoro, or chloro.

3. The compound according to claim 2, or pharmaceutically acceptable salts thereof, wherein
HetAr is a 6 membered heteroaromatic ring containing 1 nitrogen ring atom; and
HetAr is optionally substituted with 1 or 2 substituents, each substituent independently is C$_{1-4}$alkyl, C$_{1-4}$alkoxy, C$_{2-4}$alkynyl, trifluoromethyl, hydroxy, hydroxyC$_{1-4}$alkyl, fluoro, chloro, bromo, iodo, cyano, methylsulfanyl, cyclopropylethynyl-, phenylethynyl-, heteroarylethynyl-, —N(C$_{0-4}$alkyl)(C$_{0-4}$alkyl), nitro, (C$_{1-2}$alkyl)(C$_{1-2}$alkyl)NCH$_2$—, (C$_{1-2}$alkyl)HNCH$_2$—, Si(CH$_3$)$_3$—C—, or NH$_2$C(O)—.

4. The compound according to claim 2, or pharmaceutically acceptable salts thereof, wherein
HetAr is purinyl optionally substituted with 1 or 2 substituents, each substituent independently is C$_{1-4}$alkyl, C$_{1-4}$alkoxy, C$_{2-4}$alkynyl, trifluoromethyl, hydroxy, hydroxyC$_{1-4}$alkyl, fluoro, chloro, bromo, iodo, cyano, methylsulfanyl, cyclopropylethynyl-, phenylethynyl-, heteroarylethynyl-, —N(C$_{0-4}$alkyl)(C$_{0-4}$alkyl), nitro, (C$_{1-2}$alkyl)(C$_{1-2}$alkyl)NCH$_2$—, (C$_{1-2}$alkyl)HNCH$_2$—, Si(CH$_3$)$_3$—C—, or NH$_2$C(O)—.

5. The compound according to claim 2, or pharmaceutically acceptable salts thereof, wherein
HetAr is a 6 membered heteroaromatic ring containing 2 nitrogen ring atom; and
HetAr is optionally substituted with 1 or 2 substituents, each substituent independently is C$_{1-4}$alkyl, C$_{1-4}$alkoxy, C$_{2-4}$alkynyl, trifluoromethyl, hydroxy, hydroxyC$_{1-4}$alkyl, fluoro, chloro, bromo, iodo, cyano, methylsulfanyl, cyclopropylethynyl-, phenylethynyl-, heteroarylethynyl-, —N(C$_{0-4}$alkyl)(C$_{0-4}$alkyl), nitro, (C$_{1-2}$alkyl)(C$_{1-2}$alkyl)NCH$_2$—, (C$_{1-2}$alkyl)HNCH$_2$—, Si(CH$_3$)$_3$—C—, or NH$_2$C(O)—.

6. The compound according to claim 1, or pharmaceutically acceptable salts thereof, wherein
NonAr is an 8-azabicyclo[3.2.1]octane ring; and
B is aryl(CH$_2$)$_{1-3}$—SO$_2$—, wherein the aryl is optionally substituted by 1–5 substitutents, each substituent independently is C$_{1-4}$alkyl, C$_{3-6}$-cycloalkyl, C$_{1-4}$alkoxy, trifluoromethyl, bromo, fluoro, or chloro.

7. The compound according to claim 1, wherein said compound is
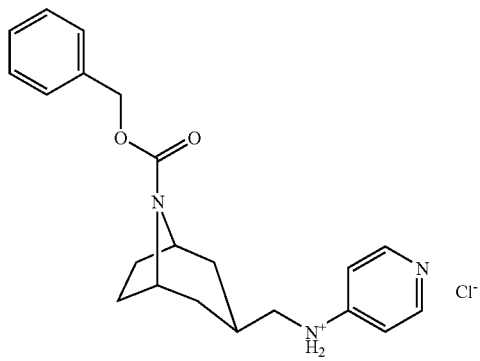
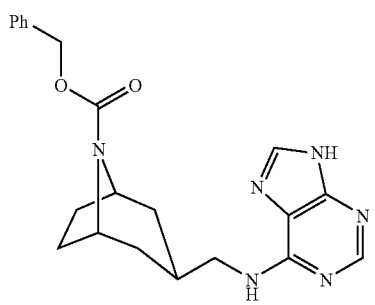
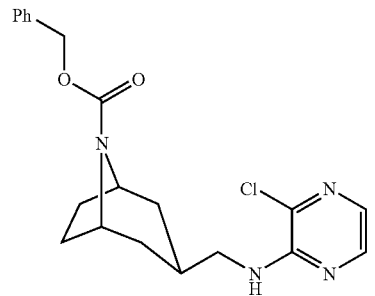
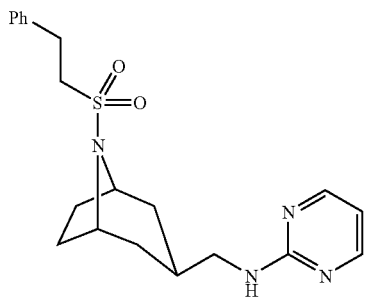
or a pharmaceutically acceptable salt thereof.
8. The compound according to claim 1, wherein said compound is
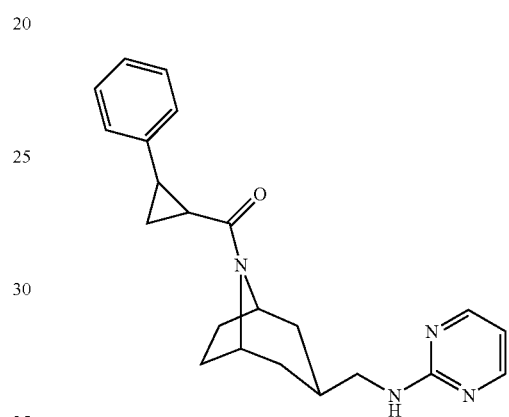
or a pharmaceutically acceptable salt thereof.
9. A pharmaceutical composition comprising an inert carrier and an effective amount of a compound according to claim 1.
* * * * *